(12) United States Patent
Sabin et al.

(10) Patent No.: US 9,599,590 B2
(45) Date of Patent: Mar. 21, 2017

(54) SIDE-ELUTING MOLECULAR FRACTIONATOR

(71) Applicant: Sage Science, Inc., Beverly, MA (US)

(72) Inventors: Douglas Grosvenor Sabin, Marblehead, MA (US); Joshua Gomes, Dartmouth, MA (US); Todd J. Barbera, Marblehead, MA (US); Charles Sidoti, Plymouth, MA (US); Simranjit Singh, Burlington, MA (US); T. Christian Boles, Bedford, MA (US)

(73) Assignee: Sage Science, Inc., Beverly, MA (US)

( * ) Notice: Subject to any disclaimer, the term of this patent is extended or adjusted under 35 U.S.C. 154(b) by 712 days.

(21) Appl. No.: 14/051,300

(22) Filed: Oct. 10, 2013

(65) Prior Publication Data

US 2015/0101932 A1    Apr. 16, 2015

Related U.S. Application Data

(60) Provisional application No. 61/713,156, filed on Oct. 12, 2012, provisional application No. 61/713,916, filed on Oct. 15, 2012, provisional application No. 61/766,910, filed on Feb. 20, 2013.

(51) Int. Cl.
  *G01N 27/447* (2006.01)
  *G01N 27/453* (2006.01)
(52) U.S. Cl.
  CPC . *G01N 27/44704* (2013.01); *G01N 27/44739* (2013.01)

(58) Field of Classification Search
  CPC .............................................. G01N 27/44743
  See application file for complete search history.

(56) References Cited

U.S. PATENT DOCUMENTS

| | | | |
|---|---|---|---|
| 4,834,862 A | 5/1989 | Breiner et al. | |
| 4,835,263 A | 5/1989 | Nguyen et al. | |
| 5,242,568 A * | 9/1993 | Ehr | G01N 27/44756 204/607 |
| 5,801,115 A | 9/1998 | Albers et al. | |
| 2011/0114487 A1 | 5/2011 | Schmidt et al. | |

FOREIGN PATENT DOCUMENTS

| | | |
|---|---|---|
| JP | 2002-310992 A | 10/2002 |
| JP | 2004-510170 A | 4/2004 |
| WO | WO-9604000 A1 | 2/1996 |
| WO | WO 02/28516 A1 | 4/2002 |
| WO | 2010/042766 A1 | 4/2010 |
| WO | WO 2012/171329 A1 * | 12/2012 ............. C12N 15/10 |

OTHER PUBLICATIONS

Full English language translation of Quan Du WO 2012/171329 A1, patent published Jun. 12, 2012.*

(Continued)

*Primary Examiner* — Alexander Noguerola
(74) *Attorney, Agent, or Firm* — Cooley LLP

(57) ABSTRACT

The disclosure provides cassettes, electrophoresis systems, methods for making the device, and methods of fractionating a sample using the cassettes and electrophoresis systems described herein.

19 Claims, 55 Drawing Sheets

(56) References Cited

OTHER PUBLICATIONS

Kumar et al. "Pyrrolidine Nucleic Acids: DNA/PNA Oligomers with 2-Hydroxy/Aminomethyl-4(thymin-1-yl)pyrrolidine-$N$-acetic acid." *Org. Lett.* 3.9(2001):1269-1272.

Lagriffoul et al. "The Synthesis, Co-Oligomerization and Hybridization of a Thymine-Thymine Heterodimer Containing PNA." *Bioorg. Med. Chem. Lett.* 4.8(1994):1081-1082.

Li et al. "Design, Simulation, and Optimization of a Miniaturized Device for Size-Fractioned DNA Extraction." *Electrophoresis.* 28(2007):4661-4667.

Petersen et al. "Synthesis and Oligomerization of $N^\delta$-Boc-$N^\alpha$-(thymin-1-ylacetyl)ornithine." *Bioorg. Med. Chem. Lett.* 6.7(1996):793-796.

Lin R. et al., "Selective Extraction of Size-Fractioned DNA Samples in Microfabricated Electrophoresis Devices," Journal of Chromatography, Elsevier Science Publishers B.V., NL, Aug. 29, 2003, pp. 255-268, vol. 1010, No. 2.

Gang Li et al., "Design of a PMMA Chip for Selective Extraction of Size-Fractioned DNA," Nano/Micro Engineered and Molecular Systems, Jan. 1, 2006, pp. 105-109.

Zheyu Li et al., "On-Chip Fraction Collection for Multiple Selected ssDNA Fragments Using Isolated Extraction Channels," Journal of Chromatograpy, Elsevier Science Publishers B.V., NL, Dec. 19, 2010, pp. 997-1003, vol. 1218, No. 7.

Zheyu Li et al., "A Simultaneous Space Sampling Method for DNA Fraction Collection Using a Comb Structure in Microfluidic Devices," Electrophoresis, Dec. 10, 2011, pps. 3392-3398, vol. 32, No. 23.

International Search Report and the Written Opinion for International Application No. PCT/US2013/064403, filed Oct. 10, 2013; mailed Jan. 24, 2014.

Australian Patent Examination Report No. 1 corresponding to Australian Application No. 2013329110, issued on Jul. 28, 2016.

Rongsheng, Lin et al., Selective extraction of size-fractioned DNA samples in microfabricated electrophoresis devices, Journal of Chromatography A, 2003, vol. 1010, pp. 255-268.

* cited by examiner

Exemplary Reservoir Volumes

| Reservoir | Dimensions |
|---|---|
| First or Upper Buffer Reservoir | 12360 µL |
| Second or Lower Buffer Reservoir | 12360 µL |
| Negative Elution Reservoir | 289 µL |
| Positive Elution Reservoir | 289µL |

Exemplary Separation Channel Dimensions
Fig. 3A
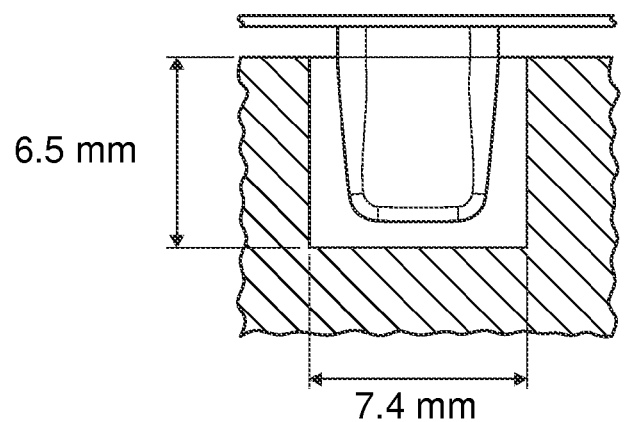
6.5 mm
7.4 mm
Cross sectional area of
separation channel: 48.1 mm²
Total Volume of
separation channel: 4985.6 µL
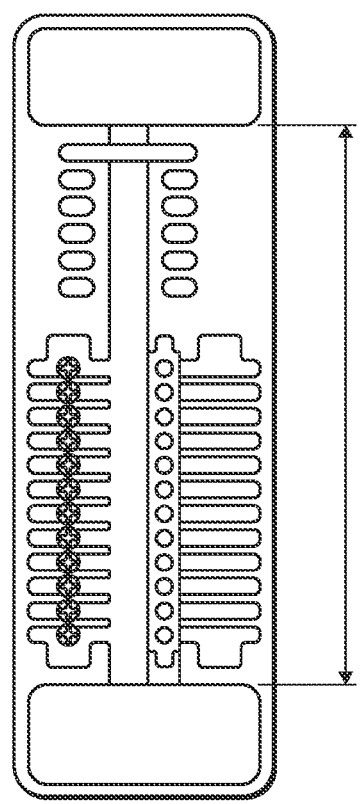
Fig. 3B Example of injection molded side-eluting cassette with upside down filling.

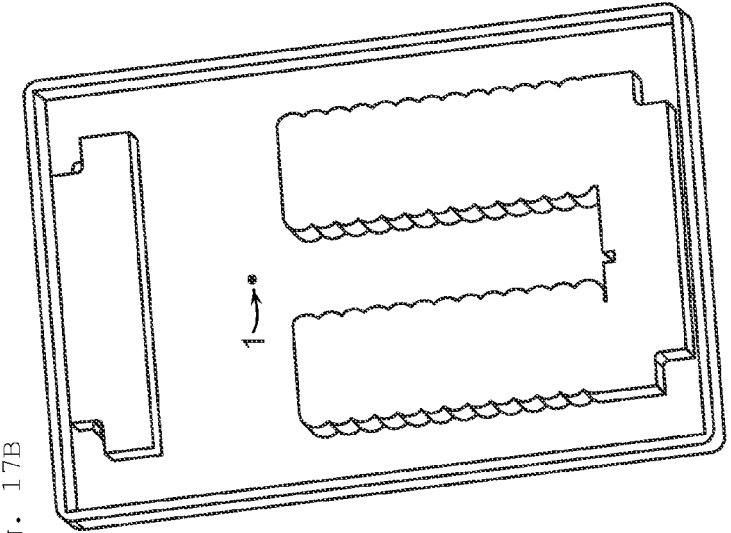

Top view of assembled cassette
Fig. 17A

Bottom view of assembled cassette
Fig. 17B

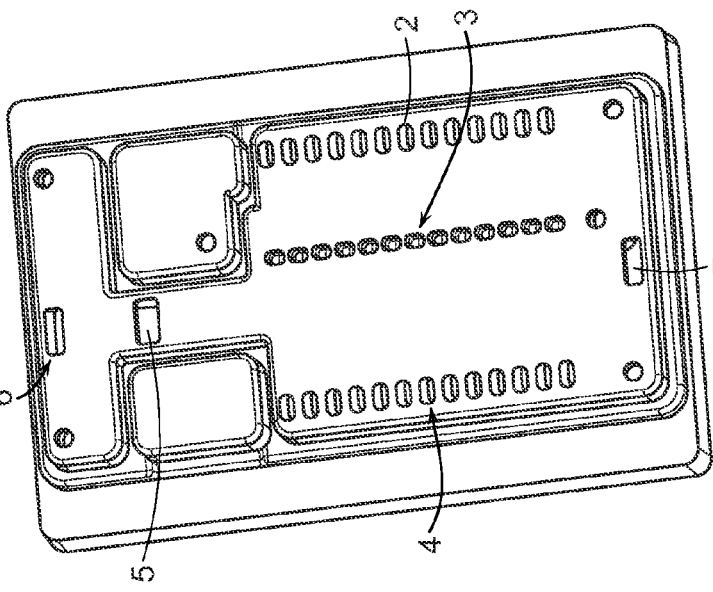

1. Port for filling gel into separation channel.
2. (+) elution electrode port (one of 13 total).
3. Elution module port (one of 13 total).
4. (−) elution electrode port (one of 13 total).
5. Sample input well.
6. (−) separation electrode port.
7. (+) separation electrode port Example of injection molded side-eluting cassette with upside down filling.

View of top (interior) surface of cassette base

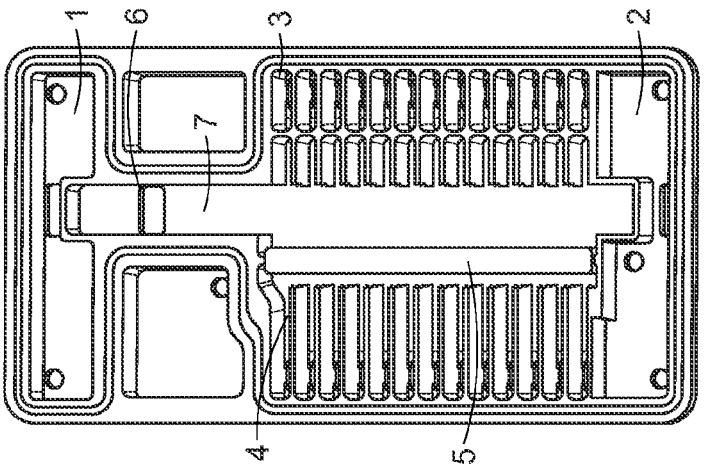

Fig. 18A

View of bottom (interior) surface of cassette top)

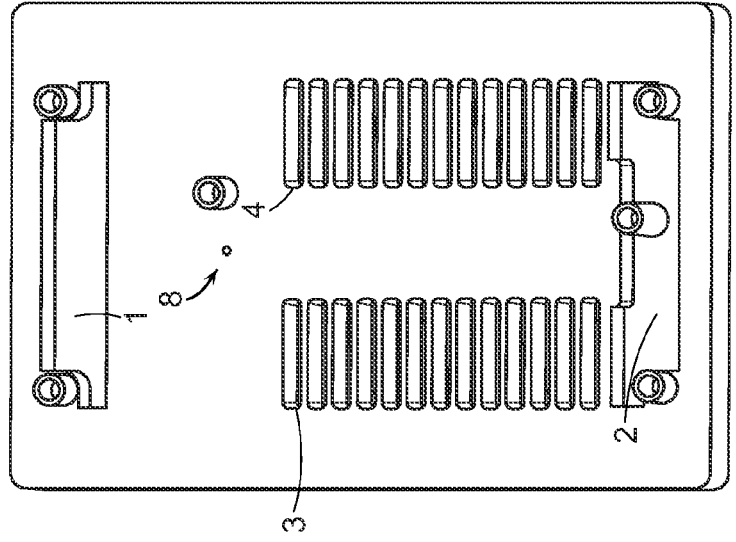

Fig. 18B 1. (−) buffer reservoir cavity for separation channel.
2. (+) buffer reservoir cavity for separation channel.
3. (−) buffer reservoir cavity for elution channel.
4. (+) buffer reservoir cavity for elution channel.
5. Elution module strip.
6. Sample well port.
7. Separation gel channel.
8. Port for filling separation gel channel.

Example of injection molded side-eluting cassette with upside down filling.

Alternative view of interior surfaces of base and top, showing elution module strip (5) and its position adjacent to separation channel (7).

Example of injection molded side-eluting cassette with upside down filling (cross-section through separation channel).

Example of injection molded side-eluting cassette with upside down filling Section through elution channel.

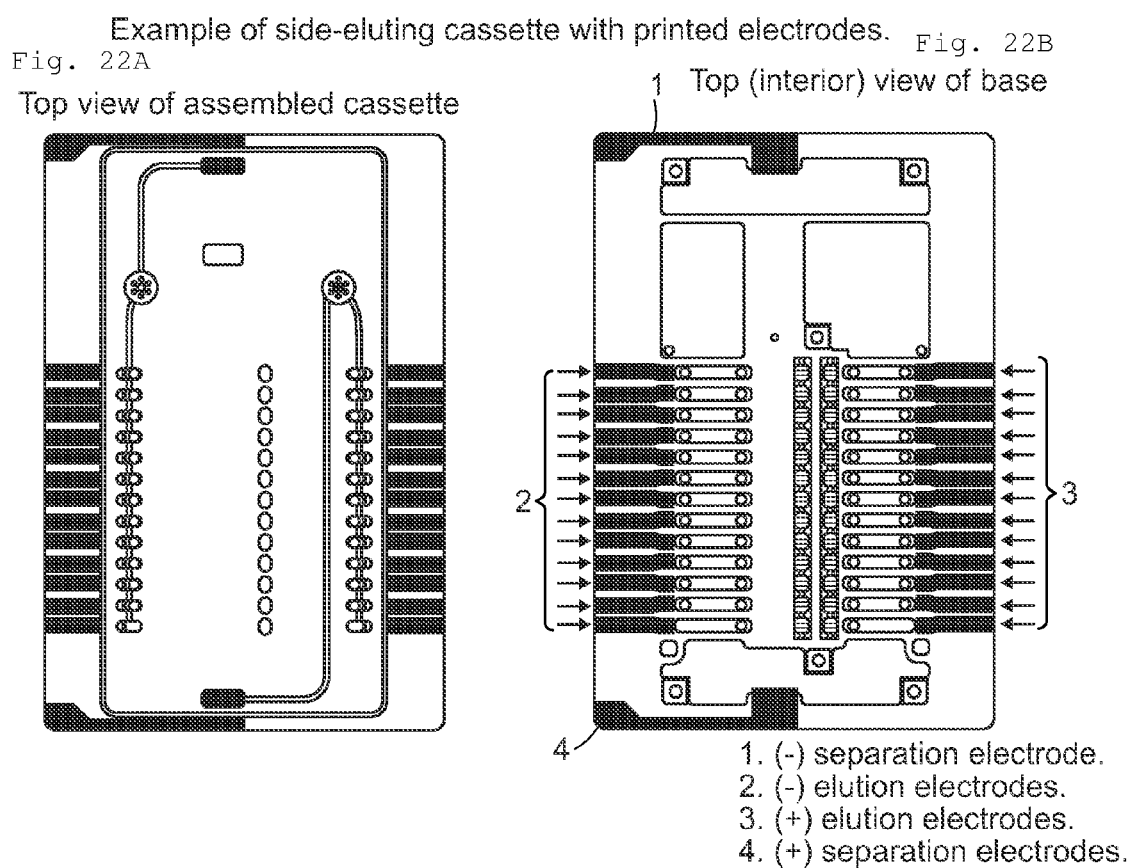
Example of side-eluting cassette with printed electrodes.
Fig. 22A Top view of assembled cassette
Fig. 22B Top (interior) view of base
1. (−) separation electrode.
2. (−) elution electrodes.
3. (+) elution electrodes.
4. (+) separation electrodes.

Example of an instrument electrode contact suitable for use with cassettes having printed electrodes Section through elution channel showing instrument contact with printed elution channel electrode.

Example of instrument-based electrode array for side-eluting cassette.
Each electrode is formed by winding conductive wire around post that will
insert into the appropriate electrode port in cassettes.

Illustration of fit between an instrument electrode array of Figure 25 and exemplary cassette designed to accept such array.

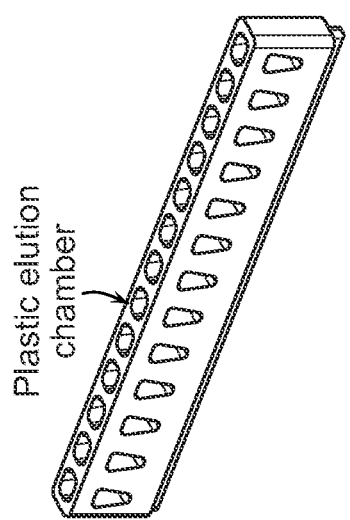
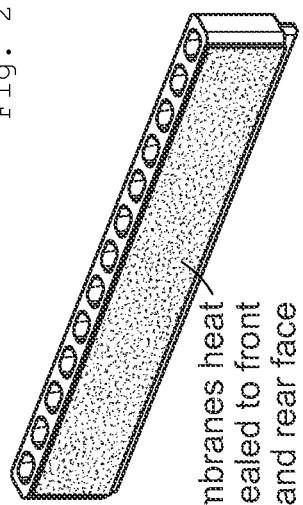
Fig. 27A — Example of elution module strip formed by heat staking; Plastic elution chamber
Fig. 27B — Membranes heat sealed to front and rear face

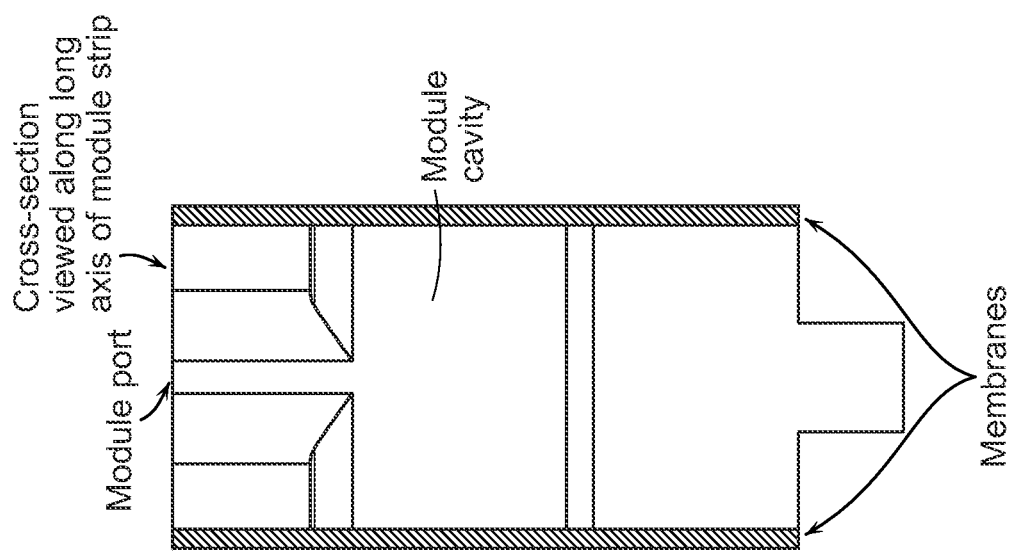

Cross section through elution channel showing heat staked elution module.

Illustration of flexible-gasket-style elution module: membranes and gasket

Cross-section of assembled flexible-gasket-style elution module strip.

Example of 2-cassette instrument for side-eluting cassette, showing window for imaging separation channel.

Window for CCD imaging of separation channel

Example of 2-cassette instrument for side-eluting cassette, showing window for imaging separation channel.

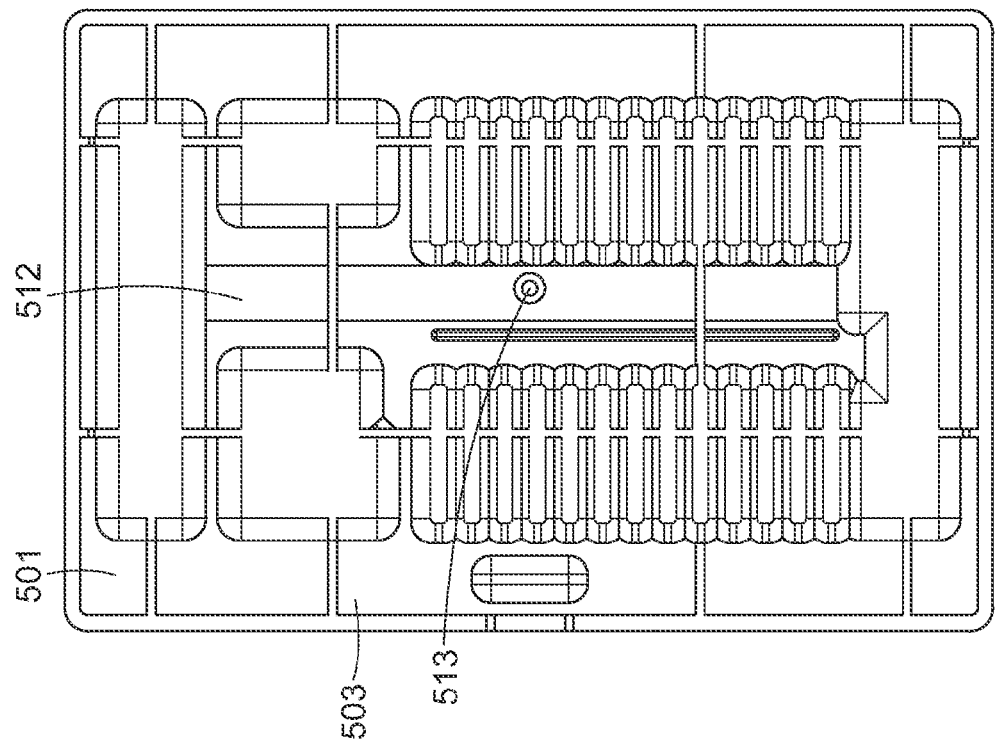
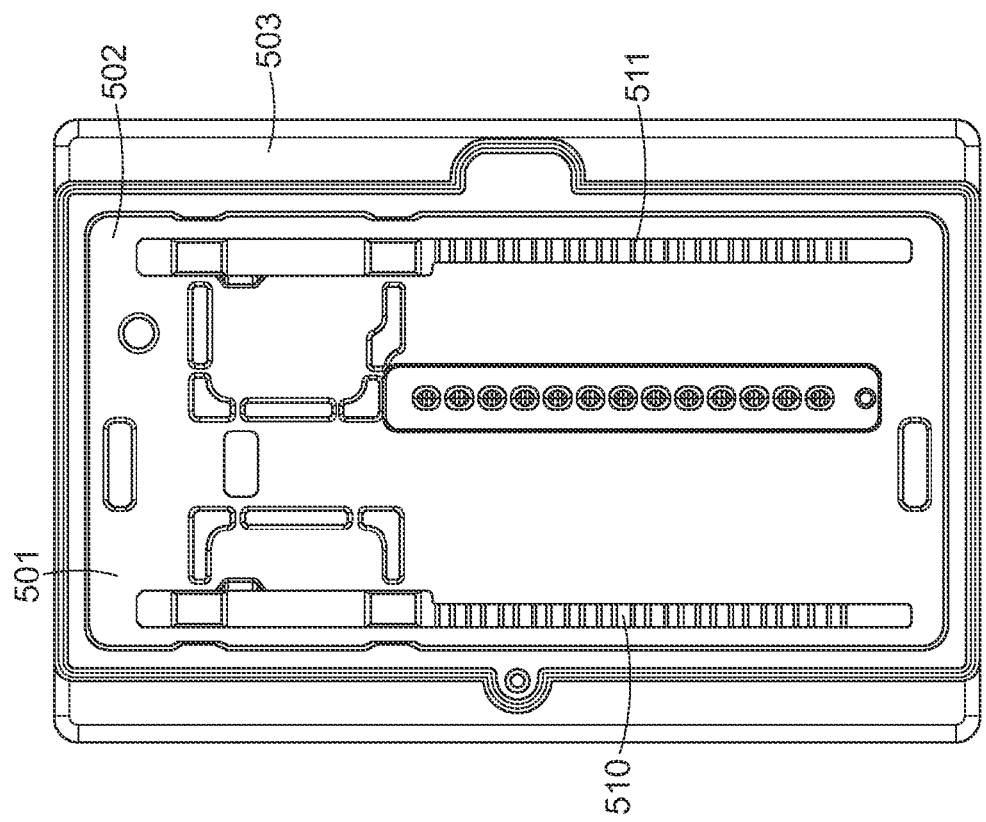

 = Buffer
 = Agaros
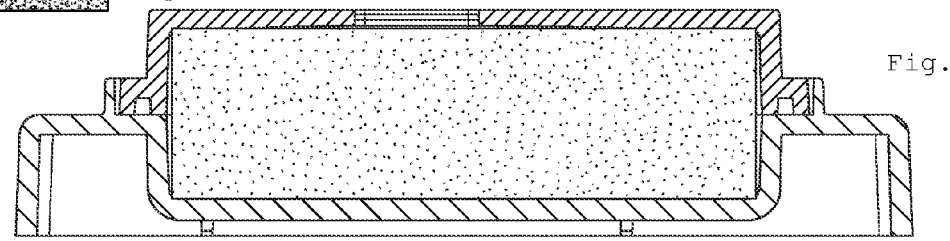
Fig. 41A
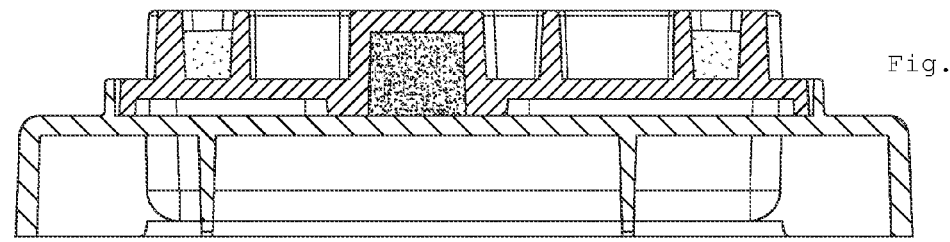
Fig. 41B
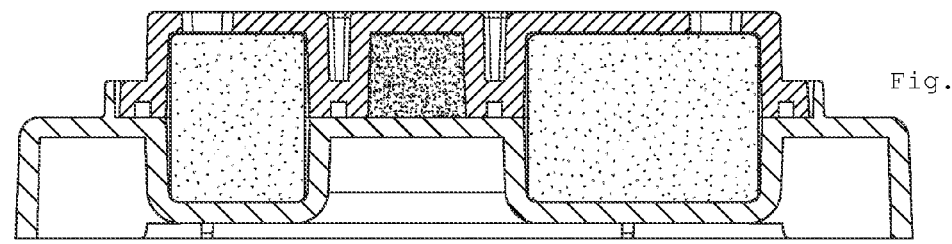
Fig. 41C
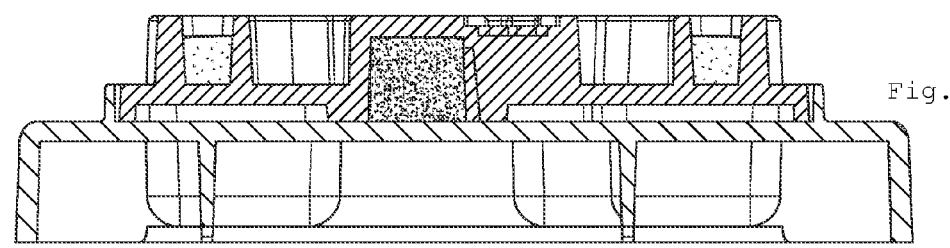
Fig. 41D
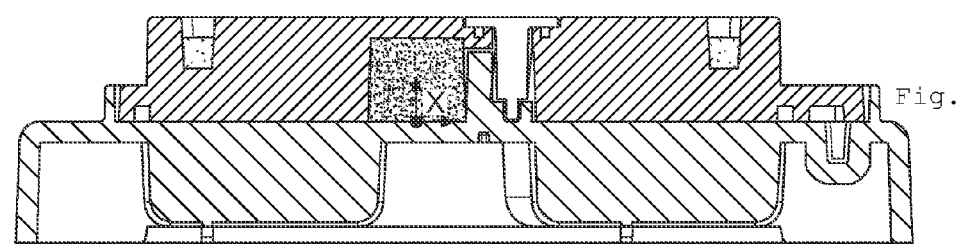
Fig. 41E
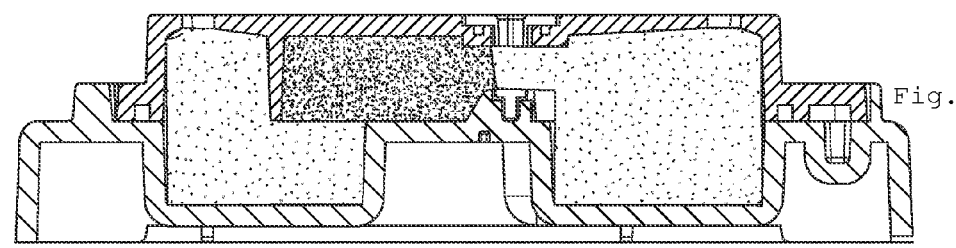
Fig. 41F

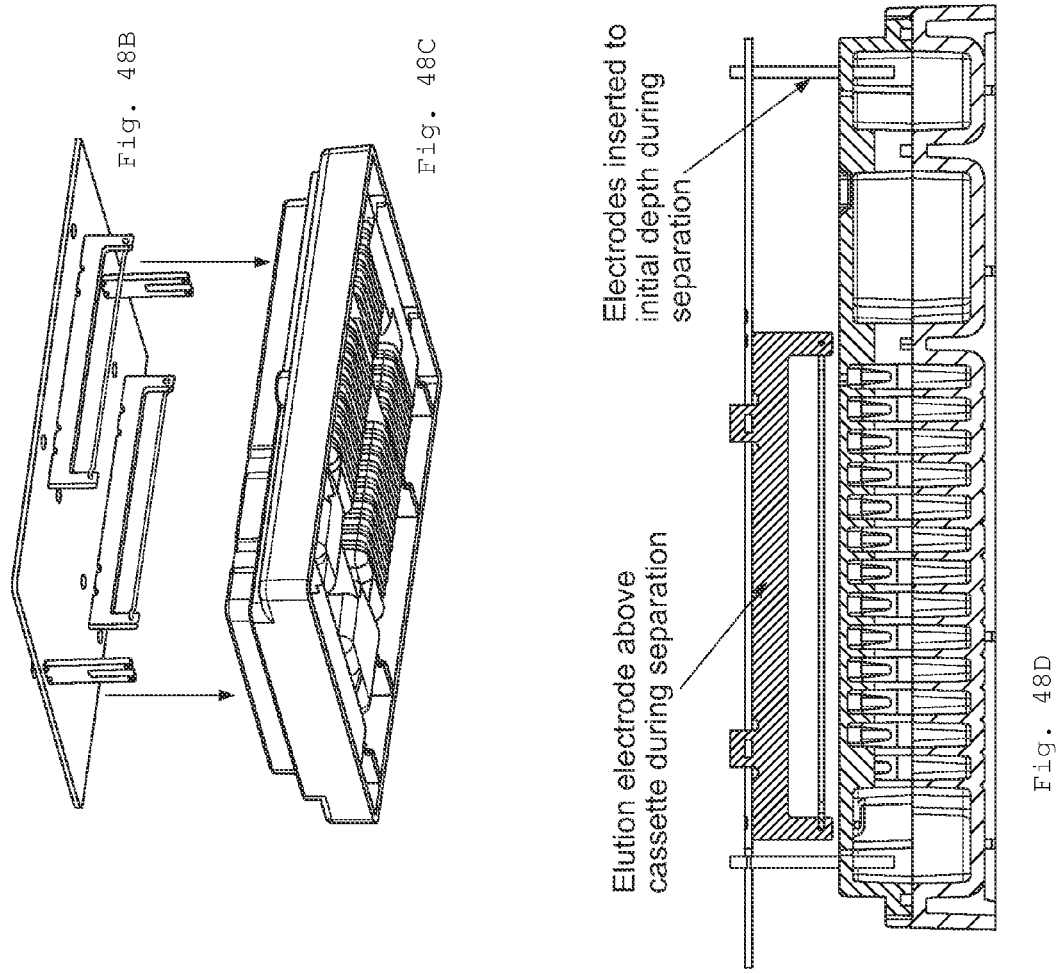
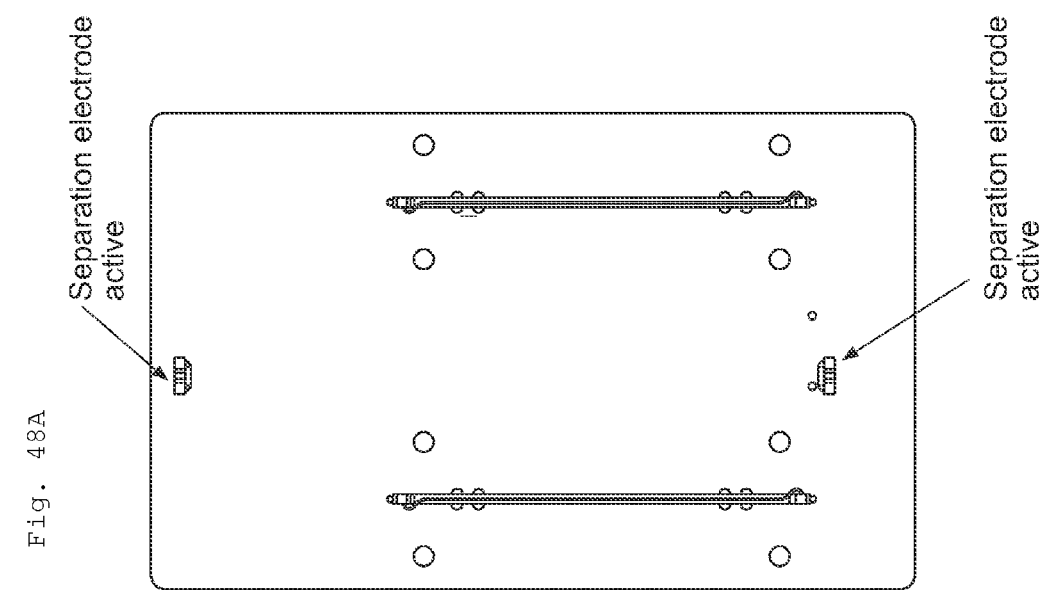

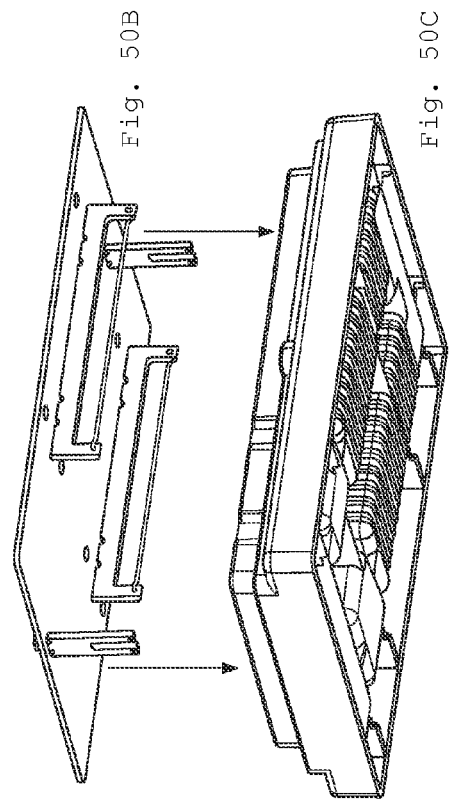
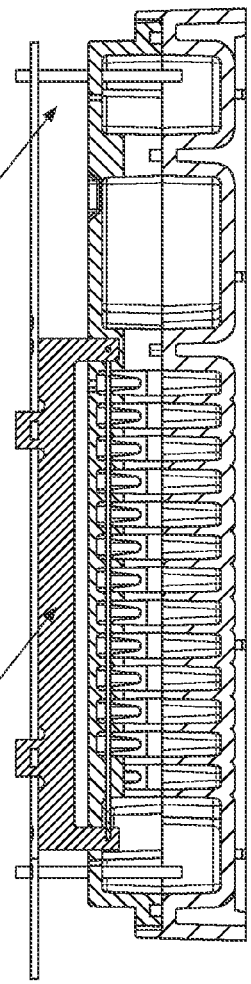
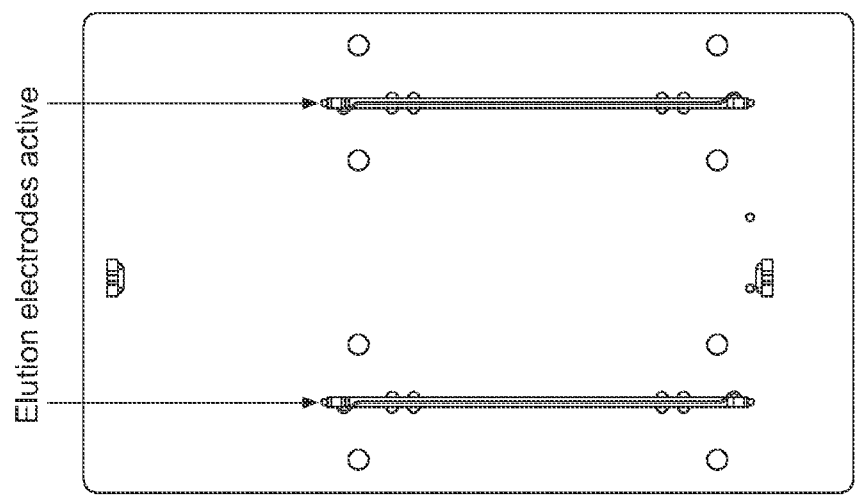

SIDE-ELUTING MOLECULAR FRACTIONATOR

RELATED APPLICATIONS

This application is related to provisional application U.S. Ser. No. 61/713,156, filed Oct. 12, 2012, provisional application U.S. Ser. No. 61/713,916, filed Oct. 15, 2012, and provisional application U.S. Ser. No. 61/766,910, filed Feb. 20, 2013, the contents of which are each herein incorporated by reference in their entirety.

FIELD OF THE DISCLOSURE

This disclosure relates generally to the field of molecular biology. Systems and methods of the disclosure are used to prepare and analyze DNA, RNA, and proteins from biological samples.

BACKGROUND

Electrophoretic separation of DNA fragments is used for a number of purposes in molecular and clinical biology and medicine, including next generation DNA sequencing, medical diagnostics, forensic science and DNA computing. Despite a demonstrated need and the efforts of skilled artisans, there remains a need in the art for a device and method of separating a single sample into fractions of multiple sizes in a single preparative electrophoresis process.

SUMMARY

This disclosure provides devices (cassettes and components thereof), systems (instruments and components thereof), and methods for separating a single sample into multiple fractions of various sizes in a single preparative electrophoresis process.

The cassettes, instruments, systems, and method of the disclosure describe multiple embodiments of devices and methods for performing preparative electrophoresis using a side-eluting technique.

In certain embodiments, the disclosure provides an electrophoresis cassette comprising a top plate comprising at least one macrofluidic separation channel, at least one of an opening, a cavity, or a recess corresponding to a portion or an entirety of a positive elution channel, at least one of an opening, a cavity, or a recess corresponding to a portion or an entirety of a negative elution channel, and at least one elution module, and a bottom plate, wherein the top plate and bottom plate are contacted or adhered to one another.

In certain embodiments, the disclosure provides an electrophoresis cassette comprising a top plate comprising at least one macrofluidic separation channel, at least one of an opening, a cavity, or a recess corresponding to a portion of a positive elution channel, at least one of an opening, a cavity, or a recess corresponding to a portion of a negative elution channel, and at least one elution module, and a bottom plate comprising at least one of an opening, a cavity, or a recess corresponding to a portion of a positive elution channel, at least one of an opening, cavity, or a recess corresponding to a portion of a negative elution channel, and at least one of an opening, cavity, or a recess corresponding to the elution module, wherein the top plate and bottom plate are contacted or adhered to one another, and wherein the contacting or adhesion of the top plate and the bottom plate forms at least one positive elution channel and at least one negative elution channel Exemplary cassettes of the disclosure having these features include, but are not limited to, the cassettes depicted in FIGS. 34 through 52.

In certain embodiments of the cassettes of the disclosure, including, but not limited to the cassettes depicted in FIGS. 34 through 52, an elution module comprises a four-sided structure having a solid bottom surface, a top surface comprising an elution port, and two side surfaces each having at least one of an opening, cavity, or a recess corresponding to at least one positive elution channel or at least one negative elution channel, and an analyte-impermeable membrane in contact with at least one side of the structure. Optionally, two side surfaces of the elution module taper from a wider configuration near the top surface to a narrower configuration near the bottom surface. An analyte-impermeable membrane may contact or adhere to a side of the structure adjacent to at least one positive elution channel. In certain embodiments of the elution module of the disclosure, an elution module comprises an analyte-permeable membrane. An analyte-permeable membrane may contact or adhere to a side of the structure adjacent to at least one negative elution channel Exemplary elution modules of the disclosure include, but are not limited to those elution modules depicted in FIGS. 27 through 31.

In certain embodiments of the cassettes of the disclosure, including, but not limited to the cassettes depicted in FIGS. 34 through 52, an elution module contacts or adheres to the top plate in a reversible manner.

In certain embodiments of the cassettes of the disclosure, including, but not limited to the cassettes depicted in FIGS. 34 through 52, the bottom plate comprises at least one notch corresponding to the at least one elution module In certain aspects of the at least one notch, an exemplary notch comprises a three-sided structure having one bottom surface and two side surfaces. In certain aspects of the at least one notch, the surfaces (bottom and/or either side) of the notch do not cover or obscure any opening, cavity, or recess of the elution module channel. In certain embodiments of the cassettes of the disclosure, including, but not limited to the cassettes depicted in FIGS. 34 through 52, the contacting or adhesion of the top plate and the bottom plate inserts at least one elution module of the top plate into at least one corresponding notch of the bottom plate. In certain embodiments of the cassettes of the disclosure, including, but not limited to the cassettes depicted in FIGS. 34 through 52, the bottom plate may comprise or further comprise at least one divider comprising a series of windows corresponding to at least one of an opening, cavity, or recess of the elution module channel, wherein each window aligns with at least one positive elution channel and at least one of a negative elution channel.

In certain embodiments of the cassettes of the disclosure, including, but not limited to the cassettes depicted in FIGS. 34 through 52, the elution module comprises at least one elution chamber and at least one elution port. For example, the at least one elution chamber may be bounded on at least one side by a surface of the elution module. Alternatively, or in addition, the at least one elution chamber may be bounded on at least one side by either an analyte-permeable or an analyte-impermeable membrane. Optionally, the at least one elution chamber may be bounded on a bottom surface and two side surfaces by a surface of the elution module. The at least one elution chamber may be bounded on two additional sides by a divider surface of the elution module (i.e. internal to the elution module) or by a divider contacted to or adhered to the bottom plate (i.e. external to the elution module). Exemplary elution module ports may be positioned on a top surface of the elution module and may align with an elution chamber, or may each align with an elution chamber if more than one elution chamber is present in the elution module. The top surface of the elution module may align with the outer surface of the top plate. The top surface of the elution module may be integral or a part of the outer surface of the top plate. Alternatively, the top surface of the elution module may be integral or a part of the elution module. Moreover, the top surface of the elution module may be separate from either the outer surface of the top plate or the elution module, and, in this embodiment, may be contacted or adhered directly or indirectly to either the top plate (e.g. inner or outer surface of the top plate) or the elution module.

In certain embodiments of the cassettes of the disclosure, including, but not limited to the cassettes depicted in FIGS. 34 through 52, an analyte-permeable barrier comprises a hydrophilic membrane or filter. The analyte-permeable barrier may comprise a least one pore having a diameter range of between 0.4 tim to 50 tim. The analyte-permeable barrier may comprise a least one pore having a diameter range of between 0.4 tim to 1 tim.

In certain embodiments of the cassettes of the disclosure, including, but not limited to the cassettes depicted in FIGS. 34 through 52, an analyte-impermeable barrier is a membrane, filter, film, or any combination thereof. The analyte-impermeable barrier may be an ultrafiltration membrane or a conductive film. Ultrafiltration membranes may comprise a least one pore having a diameter range of between 0.001 tim to 0.1 tim. Ultrafiltration membrane may have a molecular weight cutoff of between 1,000 to 30,000 daltons. Ultrafiltration membrane may have a molecular weight cutoff of between 3,000 to 10,000 daltons. The analyte-impermeable barrier may comprise a conductive film having the same charge as the analyte. The analyte-impermeable barrier may comprise a conductive film contacted with negatively-charged sulfate groups.

In certain embodiments of the cassettes of the disclosure, including, but not limited to the cassettes depicted in FIGS. 34 through 52, the top plate further comprises at least one positive elution electrode channel and at least one negative elution electrode channel. An exemplary positive elution electrode channel and negative elution electrode channel of the cassettes of the disclosure are depicted as features 511 and 510 of FIG. 34, respectively. The at least one positive elution electrode channel may occupy a volume of at least one position elution channel and the at least one negative elution electrode channel may occupy a volume of at least one negative elution channel. Furthermore, the at least one positive elution electrode channel and the at least one negative elution electrode channel may each occupy a volume of a first buffer reservoir and a volume of a second buffer reservoir. Moreover, the at least one positive elution electrode channel and the at least one negative elution electrode channel each occupy a volume of a first extra buffer reservoir and/or a volume of a second extra buffer reservoir. In certain aspects of the cassettes of the disclosure, the at least one positive elution electrode channel may occupy a volume of at least one position elution channel and the at least one negative elution electrode channel may occupy a volume of at least one negative elution channel and the at least one positive elution electrode channel and the at least one negative elution electrode channel may each occupy a volume of a first buffer reservoir and a second buffer reservoir, thereby facilitating fluid communication between each compartment of the cassette that may be filled with a buffer composition. In certain aspects of the cassettes of the disclosure, the at least one positive elution electrode channel may occupy a volume of at least one position elution channel and the at least one negative elution electrode channel may occupy a volume of at least one negative elution channel and the at least one positive elution electrode channel, the at least one negative elution electrode channel may each occupy a volume of a first buffer reservoir and a volume of a second buffer reservoir, and the at least one positive elution electrode channel and the at least one negative elution electrode channel each occupy a volume of a first extra buffer reservoir and/or a volume of a second extra buffer reservoir, thereby facilitating fluid communication between each compartment of the cassette that may be filled with a buffer composition. Fluid communication between compartments of the cassettes of the disclosure is useful for preventing the accumulation or depletion of a buffer composition in any individual compartment (e.g. reservoir or channel) of the cassette.

In certain embodiments of the cassettes of the disclosure, including, but not limited to the cassettes depicted in FIGS. 34 through 52, the top plate comprises or further comprises at least one of an opening, a cavity, or a recess corresponding to a portion of a first buffer reservoir and at least one of an opening, a cavity, or a recess corresponding to a portion of a second buffer reservoir. In certain embodiments of the cassettes of the disclosure, including, but not limited to the cassettes depicted in FIGS. 34 through 52, the bottom plate further comprises at least one of an opening, a cavity, or a recess corresponding to a portion of a first buffer reservoir and at least one of an opening, a cavity, or a recess corresponding to a portion of a second buffer reservoir. The contacting or adhesion of the top plate and the bottom plate may form a first buffer reservoir and a second buffer reservoir. In certain embodiments of the cassettes of the disclosure, including, but not limited to the cassettes depicted in FIGS. 34 through 52, the first buffer reservoir is provided at a first end of the macrofluidic separation channel and the second buffer reservoir is provided at a second end of the macrofluidic separation channel. As used to describe buffer reservoirs and separation channels of the cassettes of the disclosure, the term "first" is meant to describe a reservoir or end of a separation in proximity to a sample well, a sample well cavity or a negative separation electrode. As used to describe buffer reservoirs and separation channels of the cassettes of the disclosure, the term "second" is meant to describe a reservoir or end of a separation in proximity to a positive separation electrode.

In certain embodiments of the cassettes of the disclosure, including, but not limited to the cassettes depicted in FIGS. 34 through 52, the top plate further comprises at least one of an opening, a cavity, or a recess corresponding to a portion of a first extra buffer reservoir. In certain embodiments of the cassettes of the disclosure, including, but not limited to the cassettes depicted in FIGS. 34 through 52, the bottom plate further comprises at least one of an opening, a cavity, or a recess corresponding to a portion of a first extra buffer reservoir. The contacting or adhesion of the top plate and the bottom plate forms a first extra buffer reservoir.

In certain embodiments of the cassettes of the disclosure, including, but not limited to the cassettes depicted in FIGS. 34 through 52, the top plate further comprises at least one of an opening, a cavity, or a recess corresponding to a portion of a second extra buffer reservoir. In certain embodiments of the cassettes of the disclosure, including, but not limited to the cassettes depicted in FIGS. 34 through 52, the bottom plate further comprises at least one of an opening, a cavity, or a recess corresponding to a portion of a second extra buffer reservoir. The contacting or adhesion of the top plate and the bottom plate forms a second extra buffer reservoir.

In certain embodiments of the cassettes of the disclosure, including, but not limited to the cassettes depicted in FIGS. 34 through 52, the bottom plate further comprises a frame inside of which the top plate resides. The frame may be used to align and maintain alignment of the top and bottom plates. The frame may be used to contact and maintain contact of the top and bottom plates. The frame may be used to adhere and maintain adhesion of the top and bottom plates. Furthermore, when one or more compartments (e.g. reservoirs or channels) of the cassette are in fluid communication, the frame may be used as a boundary to confine a buffer composition within the cassette.

In certain embodiments of the cassettes of the disclosure, including, but not limited to the cassettes depicted in FIGS. 34 through 52, at least one separation channel comprises at least one sample well cavity. In certain aspects of the cassettes of the disclosure, a sample well insert may occupy a volume of the at least one sample well cavity. Upon pouring and solidifying a gel matrix composition within the at least one sample well cavity, in which a sample well insert occupies a volume thereof, removal of the sample well insert generates a sample well. In certain embodiments of the cassettes of the disclosure, including, but not limited to the cassettes depicted in FIGS. 34 through 52, a sample well insert and/or sample well cavity may align with at least one of an opening, a cavity, or a recess in an outer surface of the top plate corresponding to a sample port, through which a sample may be loaded or introduced into a gel matrix composition occupying a sample well cavity and/or separation channel of the cassette.

In certain embodiments of the cassettes of the disclosure, including, but not limited to the cassettes depicted in FIGS. 34 through 52, an outer surface of the top plate comprises at least one of an opening, a protrusion and a recess corresponding with at least one separation electrode port, one elution electrode channel, and one sample port. In certain embodiments of the cassettes of the disclosure, including, but not limited to the cassettes depicted in FIGS. 34 through 52, an outer surface of the top plate comprises or further comprises an opening, a protrusion and a recess corresponding with at least one elution module port.

In certain embodiments of the cassettes of the disclosure, including, but not limited to the cassettes depicted in FIGS. 34 through 52, an outer surface of the bottom plate comprises at least one of an opening, a protrusion and a recess corresponding with at least one port. The port may facilitate introduction of a gel matrix composition to at least one separation channel. In certain embodiments of the cassettes of the disclosure, including, but not limited to the cassettes depicted in FIGS. 34 through 52, a liquid gel matrix solution is introduced into a port on the outer surface of the bottom plate. Preferably, a liquid gel matrix solution is introduced into a port on the outer surface of the bottom plate when the outer surface is oriented such that the outer surface faces upwards. Moreover, it is preferable that a liquid gel matrix solution is introduced into a port on the outer surface of the bottom plate when the top plate and bottom plate are contacted or adhered together, and maintained in this contacted or adhered configuration until at least the liquid gel matrix composition solidifies. In certain embodiments of the cassettes of the disclosure, including, but not limited to the cassettes depicted in FIGS. 34 through 52, a port in an outer surface of the bottom plate aligns with at least one separation channel of the top plate when the top plate and bottom plate are contacted or adhered together.

In certain embodiments of the cassettes of the disclosure, including, but not limited to the cassettes depicted in FIGS. 34 through 52, the cassette is disposable.

In certain embodiments of the cassettes of the disclosure, including, but not limited to the cassettes depicted in FIGS. 34 through 52, the cassette comprises or further comprises at least one of a gel matrix composition, a liquid buffer composition, a solid buffer composition.

In certain embodiments of the cassettes of the disclosure, including, but not limited to the cassettes depicted in FIGS. 34 through 52, the macrofluidic separation channel includes at least one of a gel matrix composition, a liquid buffer composition, a solid buffer composition. The at least one of a gel matrix composition, a liquid buffer composition, a solid buffer composition may comprise at least one of a fluorophore or a chromophore. In certain embodiments of the cassettes of the disclosure, including, but not limited to the cassettes depicted in FIGS. 34 through 52, the at least one macrofluidic separation channel comprises a gel matrix composition. The gel matrix composition may fill a volume of the macrofluidic separation channel. When the gel matrix composition may fill a volume of the macrofluidic separation channel, the gel matrix composition defines at least one sample well within at least one sample well cavity.

In certain embodiments of the cassettes of the disclosure, including, but not limited to the cassettes depicted in FIGS. 34 through 52, the cassette comprises a buffer composition. The buffer composition may fill a volume of at least one buffer reservoir, at least one sample well, at least one elution channel, and at least one elution module. In certain embodiments of the cassettes of the disclosure, including, but not limited to the cassettes depicted in FIGS. 34 through 52, the buffer composition may fill a volume of at least one extra buffer reservoir.

In certain embodiments of the cassettes of the disclosure, including, but not limited to the cassettes depicted in FIGS. 34 through 52, the elution module comprises an elution buffer composition. The elution buffer composition may fill a volume of at least one elution chamber.

In certain embodiments of the cassettes of the disclosure, including, but not limited to the cassettes depicted in FIGS. 34 through 52, the cassette further comprises a removable seal. The seal may enclose at least one of an opening, a protrusion and a recess of an outer surface of the top plate or an outer surface of the bottom plate.

In certain embodiments of the cassettes of the disclosure, including, but not limited to the cassettes depicted in FIGS. 34 through 52, at least one macrofluidic separation channel is optically-transparent. The separation channel may be optically-transparent on at least one side. The separation channel may be optically-transparent on only one side.

In certain embodiments, the disclosure provides an electrophoresis system comprising:
a cassette of the disclosure, including, but not limited to the cassettes depicted in FIGS. 34 through 52; an electrode array comprising at least one of a negative separation electrode and a positive separation electrode, wherein the negative separation electrode aligns with a port in the outer surface of the top plate corresponding to a first buffer reservoir at a first end of the separation channel, wherein the positive separation electrode aligns with a port in the outer surface of the top plate corresponding to a second buffer reservoir at a second end of the separation channel, and wherein the first end of the separation channel is proximal to at least one sample well; and at least one of a negative elution electrode and a positive elution electrode, wherein the negative elution electrode aligns with an elution electrode channel in the outer surface of the top plate occupying a volume of at least one negative elution channel, wherein the positive elution electrode aligns with an elution electrode channel in the outer surface of the top plate occupying a volume of at least one positive elution channel; and a processor configured to activate power to at least one pair of positive and negative separation electrodes during a separation electrophoresis, deactivate power to the at least one pair of positive and negative separation electrodes and activate power to at least one pair of positive and negative elution electrodes during an elution electrophoresis; and a power module comprising at least one of a power supply and a relay to provide power to at least one of the processor and at least one pair of positive and negative separation electrodes or at least one pair of positive and negative elution electrodes.

In certain embodiments of the instruments and/or systems of the disclosure, including, but not limited to the instruments, systems or components thereof depicted in FIGS. 47 through 52, an instrument or system comprises at least one lid. An electrode or an electrode array may be contacted or adhered to the lid. An electrode or an electrode array may be contacted or adhered to the lid in a rigid manner such that movement of the electrode or electrode array is minimized or prevented.

In certain embodiments of the instruments and/or systems of the disclosure, including, but not limited to the instruments, systems or components thereof depicted in FIGS. 47 through 52, an instrument or system comprises at least one cassette nest contacted or adhered to at least one nest platform. The cassette nest may contact or adhere to a cassette of the disclosure, including, but not limited to the cassettes depicted in FIGS. 34 through 52. The nest platform may be configured to move towards the lid, thereby, aligning the cassette with the electrode array. Alignment of the cassette with the electrode array facilitates entry of at least one electrode of the array though at least one of an opening, a cavity, or a recess in the top plate. The at least one of an opening, a cavity, or a recess in the top plate may correspond to a reservoir or channel Optionally, the reservoir or channel is filled with a buffer composition.

In certain embodiments of the instruments and/or systems of the disclosure, including, but not limited to the instruments, systems or components thereof depicted in FIGS. 47 through 52, at least one pair of positive and negative separation electrodes extends further away from a lid of the instrument or system than at least one pair of positive and negative elution electrodes extends away from the lid. In certain aspects of these embodiments, the cassette may reside at a first position, contacting only the at least one pair of positive and negative separation electrodes during a separation electrophoresis. Moreover, the cassette may reside at a second position, contacting at least one pair of positive and negative separation electrodes and at least one pair of positive and negative elution electrodes during an elution electrophoresis. The at least one pair of positive and negative separation electrodes may be deactivated during an elution electrophoresis.

In certain embodiments, the disclosure provides a method of fractionating analytes within a sample, comprising: providing a cassette of claim a cassette of the disclosure, including, but not limited to the cassettes depicted in FIGS. 34 through 52, wherein the cassette further comprises at least one of a buffer reservoir insert that occupies a volume of at least one buffer reservoir, a sample well insert that occupies a volume of the separation channel aligned with at least one of a sample port, and an injection port, wherein the injection port comprises an opening in an outer surface of the bottom plate; inserting a gel matrix composition through the injection port; solidifying the gel matrix composition, wherein the gel matrix composition transforms from a liquid to a solid; removing the buffer reservoir insert and sample well insert, wherein a sample well is generated; filling at least one buffer reservoir and at least one pair of positive and negative elution channels with a buffer composition; and inserting the electrophoresis cassette into a system of the disclosure, including, but not limited to the systems or components thereof depicted in FIGS. 47 through 52; programming the processor of the system to selectively activate the at least one pair of positive and negative separation electrodes during a separation electrophoresis; programming the processor of the system to selectively deactivate the at least one pair of positive and negative separation electrodes and to selectively activate the at least one pair of positive and negative elution electrodes during an elution electrophoresis; applying the sample to the sample well; applying a voltage across the electrophoresis cassette during a separation electrophoresis; applying a voltage across the electrophoresis cassette during an elution electrophoresis; and collecting analytes of the sample having a desired electrophoretic mobility in the at least one elution module, thereby fractionating analytes within a sample.

In certain embodiments of the methods of the disclosure, the sample comprises at detectable compound. The sample may comprise at least one of a complex of an analyte and a fluorescent compound. Furthermore, the fluorescent compound is a fluorophore. The sample may comprise at least one of a complex of an analyte and a light-absorbing compound. Furthermore, the light-absorbing compound is a chromophore.

In certain embodiments of the methods of the disclosure, at least one of a gel matrix composition, a buffer composition, or an elution buffer composition comprises at least one of a fluorophore that complexes to at least one of an analyte. In certain embodiments of the methods of the disclosure, at least one of a gel matrix composition, a buffer composition, or an elution buffer composition comprises at least one of a chromophore that complexes to at least one of an analyte.

In certain embodiments of the methods of the disclosure, the sample comprises a molecular weight marker.

In certain embodiments of the methods of the disclosure, an analyte is a polynucleic acid or a polypeptide. The polynucleic acid may comprise deoxyribonucleic acid (DNA) or ribonucleic acid (RNA). The polynucleic acid may be double or single stranded. The polypeptide may be native or denatured.

In certain embodiments, the disclosure provides an electrophoresis cassette comprising: a plate comprising at least one macrofluidic separation channel, at least one positive elution channel, at least one negative elution channel, and at least one of an opening, a cavity, or a recess corresponding to an elution module, and at least one elution module.

In certain embodiments of the cassettes of the disclosure, an elution module comprises a four-sided structure having a solid bottom surface, a top surface comprising an elution port, and two side surfaces each having at least one of an opening, cavity, or a recess corresponding to at least one positive elution channel or at least one negative elution channel, and an analyte-impermeable membrane in contact with at least one side of the structure. The analyte-impermeable membrane may contacts or adhere to the side of the structure adjacent to at least one positive elution channel. In certain embodiments of the cassettes of the disclosure, an elution module may comprise or further comprise an analyte-permeable membrane. An analyte-permeable membrane may contact or adhere to the side of the structure adjacent to at least one negative elution channel.

In certain embodiments of the cassettes of the disclosure, an elution module contacts or adheres to the plate in a reversible manner. The elution module may contact or adhere to the at least one of an opening, a cavity, or a recess corresponding to an elution module in a reversible manner.

In certain embodiments of the cassettes of the disclosure, the cassette comprises a first buffer reservoir. The first buffer reservoir may be positioned at a first end of the separation channel. In certain embodiments of the cassettes of the disclosure, the cassette comprises a second buffer reservoir. The second buffer reservoir is positioned at a second end of the separation channel.

Using the cassettes, instruments, and methods of the disclosure, a separation electrophoresis process may be performed first. The duration of separation electrophoresis may be manipulated or optimized to selectively process input samples that include, for instance, analytes or fractions of different size ranges or different ranges of electrophoretic mobility.

The side-eluting cassettes of the disclosure elute and fractionate the contents of the separation channel in a parallel, rather than serial, manner Parallel elution is accomplished by an elution step, wherein the contents of the separation channel move in a direction that is orthogonal or perpendicular to the direction in which the analytes move during a prior separation step.

The disclosure provides a cassette containing a plate. An exemplary plate of the disclosure may include, for example, a single unit, as depicted in FIGS. 5A and 5B. Alternatively, a plate of the disclosure may include multiple units. In certain embodiments, a plate of the disclosure having multiple units may comprise a central unit. Alternatively, in certain embodiments, a plate of the disclosure having multiple units may consist essentially of a central unit. In certain embodiments, a plate of the disclosure having multiple units may comprise a central unit and a base unit. Alternatively, in certain embodiments, a plate of the disclosure having multiple units may consist essentially of a central unit and a base unit. In certain embodiments, a plate of the disclosure having multiple units may include a cover unit, a central unit and a base unit. Alternatively, in certain embodiments, a plate of the disclosure having multiple units may consist essentially of a cover unit, a central unit and a base unit. In certain embodiments (FIGS. 17-22, for example), the cassette may include a top unit, which may contain features of an exemplary cover unit and an exemplary central unit. In other embodiments (FIG. 26, for example), a cassette may include a cover unit, central unit and a base unit, wherein the cover unit comprises an electrode array. The cover unit comprising an electrode array may be provided as either a component of a cassette or as a component of an instrument that contains the cassette (FIG. 33, for example).

When a plate of the disclosure includes multiple units (a multiunit plate), a cover unit may be the same or distinct from a cover of a plate having a single unit. In one aspect, a cover unit of a plate having multiple units corresponds to the configuration of the top surface of a central unit. The cover unit may include at least one of an opening, a protrusion and a recess that align with at least one of at least one of a first buffer reservoir, a negative elution reservoir, a positive elution reservoir, and a second buffer reservoir. Alternatively, or in addition, the cover unit includes at least one of an opening, a protrusion and a recess that align with at least one of a separation channel, a first buffer reservoir, a negative elution reservoir, a positive elution reservoir, a second buffer reservoir, a sample well cavity, and sample removal port. The cover includes at least one of an opening, a protrusion and a recess that align with at least one of a separation channel, a sample well cavity, and a sample removal port. The cover may further include at least one port corresponding to at least one of an electrode, a vent, a sample well and an injection port.

When a plate of the disclosure includes multiple units, a central unit may include one or more features of a single-unit plate of the disclosure. A central unit may include a form that, at its top surface, is open-faced (see, for example, the top surface of the single-unit cassette of FIGS. 5A and B). A central unit may include a form that, at its bottom surface, is open-faced. The top and bottom surfaces of the central unit may be identical (i.e. may correspond to the same geometry of channels, reservoirs, protrusions or cavities in the central unit).

The depth of the central unit may be equal to or greater than the depth of at least one of a separation channel, a negative elution reservoir, a positive elution reservoir, a first buffer reservoir, and a second buffer reservoir. To increase the depth of any element of the central unit, a corresponding base unit also including a recess or cavity corresponding to that element may be used in combination. For example, to generate a first and a second buffer reservoir having a depth greater than a separation channel, a negative elution reservoir, and a positive reservoir, the central unit of a multiunit plate could be equal in depth to the separation channel, negative elution reservoirs, positive elution reservoirs, first buffer reservoir, and second buffer reservoir, however, this central unit could be combined with a base unit having a recess, cavity, or reservoir corresponding to the first and second buffer reservoirs. Although FIGS. 5A and B depict a single-unit plate, if the previously described example of a central unit and a corresponding base unit were united, the combination would resemble the configuration of the single-unit plate depicted in this figure.

A central unit of a multiunit plate includes an external boundary "wall". In addition, exemplary central units of a multiunit plate may include at least one of an upper surface, a side surface, and a bottom surface of at least one of a separation channel, a negative elution reservoir, and a positive elution reservoir. An exemplary central unit of a multiunit plate may include at least one of an upper surface, a side surface, and a bottom surface of at least one of a separation channel, a negative elution reservoir, a positive elution reservoir, a first buffer reservoir, and a second buffer reservoir.

A central unit may include at least one macrofluidic separation channel. The at least one macrofluidic separation channel contains a first end and a second end. The first end of the at least one macrofluidic separation channel may be adjacent to a first buffer reservoir. The second end of the at least one macrofluidic separation channel may be adjacent to a second buffer reservoir. In certain embodiments, the first end of the at least one macrofluidic separation channel is adjacent to a first buffer reservoir and the second end of the at least one macrofluidic separation channel is adjacent to a second buffer reservoir. The separation channel of a central unit may be in fluid and/or electrical communication with a first buffer reservoir and/or a second buffer reservoir.

A central unit of multi-unit plate may further include at least one negative elution reservoir and at least one positive elution reservoir. The at least one negative elution reservoir and the at least one positive elution reservoir are aligned with one another. Using a separation channel as a central axis of the central unit, the at least one negative elution reservoir and the at least one positive elution reservoir are positioned on opposite sides of the separation channel. In certain embodiments of the central unit, the axis of alignment of the at least one negative elution reservoir and the at least one positive elution reservoir is orthogonal or perpendicular to the major axis of the at least one separation channel. In a further aspect of this embodiment, the axis of alignment of the at least one negative elution reservoir and the at least one positive elution reservoir and the major axis of the at least one separation channel lie within the same plane, which is the central unit of the plate.

The central unit of a multi-unit plate may include one macrofluidic separation channel, at least one negative elution reservoir, and at least one positive elution reservoir. The central unit may include a plurality of negative elution reservoirs and a corresponding plurality of positive elution reservoirs. For example, a central unit may include one separation channel, at least 12 negative elution reservoirs, and at least 12 positive elution reservoirs. In the central unit, the separation channel may be in fluid and/or electrical communication with at least one of a negative elution reservoir and at least one of a positive elution reservoir. In a central unit, the separation channel may be in fluid and/or electrical communication with at least one of a first buffer reservoir, a negative elution reservoir, a positive elution reservoir, and a second buffer reservoir.

The central unit of a multi-unit plate may further include at least one elution module. An elution module of a central unit of a multiunit plate may include any one or more features of an elution module of a single-unit plate. An exemplary elution module is either attached to the plate of the cassette or removable from the plate of the cassette. An elution module of the disclosure may directly contact the central unit, a separation channel, a positive elution reservoir, and/or an elution module cavity positioned within the central unit, a separation channel, or a positive elution reservoir.

In certain embodiments of a side-eluting cassette of the disclosure, the top unit (which may comprise all features of a cover unit and a central unit), comprises at least one separation channel, wherein the entirety of the separation channel lies within the top unit (as seen in FIG. 18 (right panel), FIG. 19 (bottom schematic), FIG. 20, FIG. 21, for example). When contacted to a base unit, the separation channel is enclosed on the top and sides by the top unit and on the bottom, by the top surface of the bottom unit. When a liquid gel matrix composition is inserted into the separation channel filling port of the base unit of this exemplary cassette, by placing the assembled cassette upside down on a work surface (such that the top unit is underneath the bottom unit), the liquid gel matrix composition (which ultimately forms a solid gel matrix composition) is confined to the at least one separation channel without the use of, for example, removable dams or other obstructive devices. In certain embodiments (FIGS. 17-22, for example), an exemplary cassette having a top unit that entirely contains at least one separation channel and a base unit, includes a cover unit and a central unit. Exemplary cover units may comprise an electrode array (as shown, for example, in FIGS. 25 and 26). Exemplary electrode arrays may be composed of a printed circuit board (PCB) with screws protruding through the PCB. Exemplary screws of this embodiment may be comprised of a plastic material. In this example, a conductive wire (such as a platinum wire) may be wound or wrapped around the screws and connected to the circuits on the PCB. When this electrode array is contacted to a cassette of the disclosure or a central unit thereof, the conductive wire (preferably platinum) provides a corrosion-resistant electrical contact between an electrophoresis buffer in at least one buffer reservoir of the cassette and the PCB and/or instrument of the disclosure. A cover unit comprising an electrode array may be provided as either a component of a cassette or as a component of an instrument that contains the cassette (FIG. 33, for example).

When a plate of the disclosure includes multiple units, the plate may comprise a base unit. An exemplary base unit may include any geometry, including, but not limited to a surface, reservoir, channel, cavity or protrusion corresponding to at least one of a surface, reservoir, channel, cavity or protrusion of a corresponding central unit. A base unit have any depth, however, the length and width of a base unit typically correspond to a central unit, and, preferably, correspond to a central unit to which the base unit is connected.

A base unit of a multiunit plate includes an external boundary "wall". In addition, exemplary base units of a multiunit plate may include at least one of an upper surface, a side surface, and a bottom surface of at least one of a separation channel, a negative elution reservoir, and a positive elution reservoir. An exemplary central unit of a multiunit plate may include at least one of an upper surface, a side surface, and a bottom surface of at least one of a separation channel, a negative elution reservoir, a positive elution reservoir, a first buffer reservoir, and a second buffer reservoir.

In certain embodiments of a base unit of a multiunit plate, the base unit includes an external boundary "wall". This "wall" may serve as a frame. The frame may enclose an insertable surface made from any material. The material of an insertable surface may be conductive or non-conductive. Exemplary insertable surfaces include, but are not limited to, a membrane, a filter, a glass, a polymer, a plastic, and a resin. Additionally, one or more electrodes may be connected to the insertable surface. For example, an electrode may be attached or incorporated into the surface. Alternatively, or in addition, an electrode may be printed onto the surface using a conductive ink. In a preferred embodiment, one or more electrodes (composed of a conductive ink) are printed onto a plastic or polymer-based insertable surface, which is subsequently positioned inside of a base unit serving as a frame. Prior to casting a gel matrix composition in a corresponding central unit, the base unit (including the frame, surface, and printed electrodes) is connected to the central unit.

A base unit and a central unit of a multiunit plate are connected, and may be maintained as a connected complex by gravity, a pressure-fit (for example, compression of two interlocking units together), the use of an adhesive, or the use of a sealant. A base unit and a central unit of a multiunit plate may be manufactured separately, but assembled by the manufacturer prior to casting of a gel matrix composition in a cassette and/or shipment of a cassette to a user. Alternatively, a base unit and a central unit of a multiunit plate may be manufactured separately, but assembled by the user prior to casting a gel matrix composition in the multiunit plate.

When a base unit of a multiunit plate is used as a frame for an insertable surface, the base unit and the insertable surface are connected, and may be maintained as a connected complex by gravity, a pressure-fit (for example, compression of two interlocking units together), the use of an adhesive, or the use of a sealant. A base unit and an insertable surface may be manufactured separately, but assembled by the manufacturer prior to connection of a base unit with a central unit. Alternatively, a base unit and an insertable surface may be manufactured separately, but assembled by the user prior to connection of a base unit with a central unit.

A base unit and a central unit of a multiunit plate may be manufactured by cutting through a single unit plate to generate a separate base unit and central unit. In this embodiment, for example, a base unit may be used as a frame to enclose an insertable surface made from any material described herein. The material of an insertable surface may be conductive or non-conductive. Exemplary insertable surfaces include, but are not limited to, a membrane, a filter, a glass, a polymer, a plastic, and a resin. Additionally, one or more electrodes may be connected to the insertable surface. For example, an electrode may be attached or incorporated into the surface. Alternatively, or in addition, an electrode may be printed onto the surface using a conductive ink. In a preferred embodiment, one or more electrodes (composed of a conductive ink) are printed onto a plastic or polymer-based insertable surface, which is subsequently positioned inside of a base unit serving as a frame. Prior to casting a gel matrix composition in a corresponding central unit, the base unit (including the frame, surface, and printed electrodes) is connected to the central unit.

In certain embodiments of an exemplary side-eluting cassette of the disclosure having printed electrodes on either the cassette or a base unit of a cassette, the electrodes may comprise conductive plastics or conductive inks (as shown, for example, in FIGS. 22 and 24). A conductive ink of the disclosure may comprise glue having suspended conductive materials therein (such as carbon black). Conductive materials may, for example, be screen-printed or ink-jet printed onto a cassette or the base unit of a cassette to serve as one or more electrodes. Moreover, any known means of printing, drawing, painting, spreading, applying or operably-linking or fixing a conductive material onto a cassette or a base unit thereof may be used to contact and/or maintain contact of electrodes to cassettes of the disclosure or base units thereof.

The disclosure further provides exemplary instruments for containing one or more side-eluting cassettes of the disclosure that may comprise at least one of an imaging device, an electrode array, a power supply, a processor, or a computer. When the cassettes of the disclosure comprise printed electrodes, exemplary instruments of the disclosure contain devices to connect the printed electrodes of the cassette to the instrument. For example, FIGS. 23 and 24 depict connection devices for contacting at least one printed electrode of the cassette to at least one conductive circuit or power source of the instrument. It is understood that the connection devices shown in the figures of the disclosure are nonlimiting examples, and, furthermore, any conductive device that conforms to the configuration of either a cassette or instrument of the disclosure may be used.

The disclosure provides a cassette containing a plate including at least one macrofluidic separation channel. The at least one macrofluidic separation channel contains a first end and a second end. In certain embodiments of the cassette, the first end of the at least one macrofluidic separation channel is adjacent to a first buffer reservoir. In certain embodiments of the cassette, the second end of the at least one macrofluidic separation channel is adjacent to a second buffer reservoir. In certain embodiments of the cassette, the first end of the at least one macrofluidic separation channel is adjacent to a first buffer reservoir and the second end of the at least one macrofluidic separation channel is adjacent to a second buffer reservoir. The separation channel may be in fluid and/or electrical communication with a first buffer reservoir and/or a second buffer reservoir.

The disclosure provides a cassette containing a plate including at least one macrofluidic separation channel, at least one negative elution reservoir, and at least one positive elution reservoir. The at least one macrofluidic separation channel contains a first end and a second end. In certain embodiments of the cassette, the first end of the at least one macrofluidic separation channel is adjacent to a first buffer reservoir. In certain embodiments of the cassette, the second end of the at least one macrofluidic separation channel is adjacent to a second buffer reservoir. In certain embodiments of the cassette, the first end of the at least one macrofluidic separation channel is adjacent to a first buffer reservoir and the second end of the at least one macrofluidic separation channel is adjacent to a second buffer reservoir. The separation channel may be in fluid and/or electrical communication with a first buffer reservoir and/or a second buffer reservoir. The at least one negative elution reservoir and the at least one positive elution reservoir are aligned with one another. Using the at least one separation channel as a central axis of the plate, the at least one negative elution reservoir and the at least one positive elution reservoir are positioned on opposite sides of the at least one separation channel. In certain embodiments of the cassette, the axis of alignment of the at least one negative elution reservoir and the at least one positive elution reservoir is orthogonal or perpendicular to the major axis of the at least one separation channel. In a further aspect of this embodiment, the axis of alignment of the at least one negative elution reservoir and the at least one positive elution reservoir and the major axis of the at least one separation channel lie within the same plane, which is the plate of the cassette. In certain embodiments of the cassette, the plate includes one macrofluidic separation channel, at least one negative elution reservoir, and at least one positive elution reservoir. In a further aspect of this embodiment, the cassette includes a plurality of negative elution reservoirs and a corresponding plurality of positive elution reservoirs. For example, a cassette may include one separation channel, at least 12 negative elution reservoirs, and at least 12 positive elution reservoirs. The separation channel may be in fluid and/or electrical communication with at least one of a negative elution reservoir and at least one of a positive elution reservoir. Furthermore, the separation channel may be in fluid and/or electrical communication with at least one of a first buffer reservoir, a negative elution reservoir, a positive elution reservoir, and a second buffer reservoir.

The disclosure provides a cassette containing a plate including at least one macrofluidic separation channel, at least one negative elution reservoir, at least one positive elution reservoir, and further includes at least one elution module. An exemplary elution module of the disclosure is attached to the plate of the cassette or removable from the plate of the cassette. An elution module of the disclosure may directly contact the plate, a separation channel, a positive elution reservoir, and/or an elution module cavity positioned within the plate, a separation channel, or a positive elution reservoir.

An elution module of the disclosure may include at least one of an analyte-permeable barrier, a sample collection chamber including a sample removal port, and an analyte-impermeable barrier. In certain embodiments of the elution module, the elution module includes only an analyte-permeable barrier. Alternatively, or in addition, the elution module includes an analyte-permeable barrier and an analyte impermeable barrier. In certain embodiments of the elution module, the elution module includes an analyte-permeable barrier, a sample collection chamber, and an analyte-impermeable barrier. In certain embodiments of the elution module, the elution module includes an analyte-permeable barrier, a sample collection chamber including a sample removal port, and an analyte-impermeable barrier. Exemplary analyte-permeable barriers of the cassettes of the disclosure may comprise a microporous membrane. Exemplary analyte-impermeable barriers of the cassettes of the disclosure may comprise an ultrafiltration membrane.

Prior to electrophoresis, a volume of an elution module of the disclosure may be filled with an elution buffer composition. The elution buffer composition may be the same or distinct from one or more buffer compositions used in the cassette. In certain embodiments of the elution module, a volume of an elution module of the disclosure may be filled with an elution buffer composition that is the same or distinct from all other buffer compositions used in the cassette.

An elution module of the disclosure may be manufactured and/or inserted into a cassette individually or as a plurality of elution modules combined into a single strip. The number of elution modules included in an elution module strip may correspond to the number of positive elution reservoirs within a cassette. However, it is contemplated that multiple strips may be inserted into a cassette. Regardless of the configuration of individual elution modules and those combined within a strip, it is preferred that the number of total elution modules inserted into a cassette equal the number of positive elution reservoirs within the cassette.

Optionally, the elution modules of the disclosure or strips thereof are removable. Optionally, one or more components of an elution module is removable. In certain embodiments, the elution module contains, in the direction of electrophoresis, a first removable side, an analyte-permeable membrane, a sample collection chamber, an analyte-impermeable membrane, and a second removable side. The removable sides are removable portions of the sample collection chamber with at least one of an opening, protrusion, or recession for binding either the analyte-permeable or analyte-impermeable membrane to the sample collection chamber.

An exemplary analyte-permeable barrier of the elution module may include, but is not limited to, a hydrophilic membrane, a microporous membrane, and a filter. In certain embodiments, the analyte-permeable barrier includes a least one pore having a diameter range of between 0.4 tim to 50 tim, and preferably, of between 0.4 tim to 1 tim.

An exemplary analyte-impermeable barrier of the elution module is a membrane, filter, film, or any combination thereof. Preferably, the analyte-impermeable barrier is an ultrafiltration membrane or a conductive film. In certain embodiments, the ultrafiltration membrane contains a least one pore having a diameter range of between 0.001 tim to 0.1 tim. Alternatively, or in addition, the ultrafiltration membrane has a molecular weight cutoff of between 1,000 to 30,000 daltons. Preferably, the ultrafiltration membrane has a molecular weight cutoff of between 3,000 to 10,000 daltons. In other embodiments, the analyte-impermeable barrier includes a conductive film having the same charge as the analyte or a conductive film contacted with negatively-charged sulfate groups.

FIGS. 27 and 28 depict one methods of manufacturing elution module strips of the disclosure. An exemplary elution module strip comprises at least one sample collection chamber (also known as a module cavity) having a sample collection port (also known as a module port), a front side and a rear side. The sample collection port is preferably positioned within a top side of the sample collection chamber. The front and rear sides may be removable. Alternatively, the front and rear sides may be integral to the elution module. Exemplary sample collection chambers may be separated from one another by side barriers, dividers, or walls within the module strip. In the elution module strip of FIGS. 27 and 28, the elution module strip contains multiple sample collection chambers, each having a sample collection port, an integral front side, an integral rear side, and at least one side barrier, divider, or wall separating each sample collection chamber from the other sample collection chambers. The front and rear sides of each sample collection chamber may contain at least one of an opening, protrusion, or recession for binding either the analyte-permeable or analyte-impermeable membrane to the sample collection chamber. In the embodiments depicted in FIGS. 27 and 28, an analyte permeable membrane is sealed to a front side of each sample collection chamber and an analyte-impermeable membrane is sealed to a rear side of each sample collection chamber. By way of orientation, along the direction of electrophoresis, an analyte traverses a front side of an elution module of the disclosure whereas only ions traverse a rear side of the elution module (the analyte-impermeable membrane affixed thereto prevents movement of the analyte across a rear side of a sample collection chamber). The analyte-permeable and analyte-impermeable membranes may be affixed to at least one sample collection chamber by, for example, heat staking or heat sealing. According to this method, application of heat a membrane causes it to deform and, consequently, fill or fit into the at least one of an opening, protrusion, or recession in each of the front and rear sides of a sample collection chamber. The result is the formation of a tight slip or bonded fit between a membrane and at least one of an opening, protrusion, or recession in either the front or rear side of a sample collection chamber.

FIGS. 29, 30, and 31 depict an alternative method of manufacturing an elution module strip of the disclosure. According to this method, the elution module comprises a V-shaped structure (also known as a gasket) having at least a bottom side, a front side, and a rear side. Each of the front and the rear sides has at least one of an opening, a protrusion, or a recession. Preferably, the V-shaped structure comprises at least one of an analyte-permeable barrier or membrane and an analyte-impermeable barrier or membrane. In certain embodiments, the at least one analyte-permeable barrier or membrane contacts the front side of the V-shaped elution module. Preferably, the at least one analyte-permeable barrier or membrane contacts the inside surface of the front side of the V-shaped elution module. In certain embodiments, the at least one analyte-impermeable barrier or membrane contacts the rear side of the V-shaped elution module. Preferably, the at least one analyte-impermeable barrier or membrane contacts the inside surface of the rear side of the V-shaped elution module. In certain embodiments, the at least one analyte-permeable barrier or membrane contacts the front side of the V-shaped elution module and the at least one analyte-impermeable barrier or membrane contacts the rear side of the V-shaped elution module. Preferably, the at least one analyte-permeable barrier or membrane contacts the inside surface of the front side of the V-shaped elution module and the at least one analyte-impermeable barrier or membrane contacts the inside surface of the rear side of the V-shaped elution module. The V-shaped elution module (alone or comprising one or more barriers or membranes), fits into a V-shaped notch on a base unit of a side-eluting cassette of the disclosure. When a V-shaped elution module comprising at least one of an analyte-permeable and an analyte-impermeable membrane is inserted into a V-shaped notch on a base unit of a cassette, a V-shaped protrusion on a central or top unit of a cassette fits inside the elution module when the base and central/top units are assembled or compressed, thereby sealing the at least one of an analyte-permeable and an analyte-impermeable barrier or membrane to the elution module (as shown in FIG. 31, for example). This seal is maintained by, for example, gravity or a pressure-fit. Alternatively, or in addition, the barriers or membranes may be maintained in the V-shaped elution module by use of adhesive glue or solvent bonding. For example, the at least one of an analyte-permeable and an analyte-impermeable barrier or membrane may be adhered to the V-shaped notch on the central/top unit of the cassette and subsequently fit into the V-shaped elution module upon assembly or compression of the central/top unit to the base unit of the cassette (as shown in FIG. 31, for example).

These methods are meant to be nonlimiting examples of contemplated manufacturing methods. All alternative methods capable of producing an elution module strip of the disclosure are also contemplated. Alternative methods of maintaining at least one barrier or membrane to at least a front or rear side of at least one sample collection chamber include, but are not limited to, gluing or solvent bonding.

Exemplary cassettes of the disclosure may be partially or entirely optically-transparent. Exemplary macrofluidic separation channels of the disclosure may be partially or entirely optically-transparent. Exemplary elution reservoirs (negative and positive) may be partially or entirely optically-transparent. Exemplary elution modules or strips thereof may be partially or entirely optically-transparent. Any feature of the cassette may be optically-transparent on at least one side, on only one side, or on only a portion of one side. Any feature of the cassette may be optically-transparent may be partially or entirely optically-transparent on a bottom side, a top side, a vertical or horizontal side or any combination thereof. Preferably, optical transparency is maintained along the entire length of the cassette, separation channel, elution reservoir, or elution module.

Exemplary cassettes may contain at least one dam within at least one separation channel Preferably, a cassette contains two dams within at least one separation channel. The term "dam" is meant to describe a barrier structure that partitions the separation channel. In one embodiment of the disclosure, a dam is positioned in at least one separation channel, between the first buffer reservoir and a sample well cavity or recess (located either within the separation channel or on either side thereof). In another embodiment, a dam is positioned in at least one separation channel between an orthogonal axis formed by at least one negative elution reservoir and at least one positive elution reservoir, and a second buffer reservoir.

In certain embodiments, a dam is formed from a frame onto which is attached to an ion-permeable barrier. The ion-permeable barrier is also preferably permeable to the buffer composition. The frame recapitulates the geometry of the separation channel, i.e. if the channel is rectangular, then the dam frame is rectangular. The ion-permeable barrier is composed of a hydrophilic membrane or filter. In certain embodiments, the hydrophilic membrane or filter includes a least one pore having a diameter range of between 0.001 µm to 1 µm, and preferably, of between 0.45 µm to 1 µm. The analyte permeable or impermeable membranes described herein for use in the elution chamber could also be used as a membrane for a dam. Importantly, the dam structure restrains the flow of unsolidified gel matrix molecules to the separation channel during gel casting, e.g. the portion of the separation channel between the first dam and the second dam. The dam is electrically conductive, and therefore, does not disrupt or distort electric fields or currents present in or around the at least one separation channel Preferably, dam structures are inserted prior to attachment of the cover, and, therefore, in these preferred embodiments, the dam structures are permanent. Alternatively, the dam is removable from at least one separation channel because the cover is not permanently attached onto the base of the electrophoresis cassette. The dam occupies the total cross-sectional area of the separation channel. Accordingly, a dam prevents gel matrix molecules from traversing its membrane, such that upon injection of a gel-matrix composition, the dame effectively partitions the separation channel into at least one buffer composition filled and at least one gel matrix-filled compartment, respectively.

An exemplary cassette includes a cover for the plate. In one aspect, the cover includes a configuration that corresponds to the configuration of the top of the plate. In another aspect, the cover includes at least one of an opening, a protrusion and a recess that align with at least one of a first buffer reservoir, a negative elution reservoir, a positive elution reservoir, and a second buffer reservoir. Alternatively, or in addition, the cover includes at least one of an opening, a protrusion and a recess that align with at least one of a separation channel, a first buffer reservoir, a negative elution reservoir, a positive elution reservoir, a second buffer reservoir, a sample well cavity, and sample removal port. In another embodiment, the cover includes at least one of an opening, a protrusion and a recess that align with at least one of a separation channel, a sample well cavity, and a sample removal port. The cover may further include at least one port corresponding to at least one of an electrode, a vent, and a sample well.

An electrode port of the cassette is either a negative electrode port or a positive electrode port. The at least one negative electrode port may correspond to a separation electrode, and, furthermore, may be positioned within or adjacent to a first buffer reservoir, or, alternatively, between a first buffer reservoir and a sample well (or sample well insert, or sample well cavity). The at least one negative electrode port may correspond to an elution electrode, and, furthermore, may be positioned within or adjacent to a negative elution reservoir. The at least one positive electrode port may correspond to a separation electrode, and, furthermore, may be positioned within or adjacent to a second buffer reservoir, or, alternatively, between an axis corresponding to at least one negative elution reservoir and at least one positive elution reservoir and a second buffer reservoir. The at least one positive electrode port may correspond to an elution electrode, and, furthermore, may be positioned within or adjacent to a positive elution reservoir.

A cassette of the disclosure may contain at least one of a cavity for a first dam, a sample well cavity, and a cavity for a second dam.

A cassette of the disclosure may include at least one of a gel matrix composition, a liquid buffer composition, a solid buffer composition. Moreover, a separation channel of the cassette may include at least one of a gel matrix composition, a liquid buffer composition, a solid buffer composition. In certain aspects, at least one of a gel matrix composition, a liquid buffer composition, a solid buffer composition contains at least one of a fluorophore or a chromophore. The fluorophore is a sample, an analyte, or a fraction or is bound to a sample, an analyte, or a fraction. Similarly, the chromophore is a sample, an analyte, or a fraction or is bound to a sample, an analyte, or a fraction. An exemplary fluorophore is ethidium bromide, which binds to polynucleic acids and allows detection of the polynucleic acid analyte. Moreover, a polypeptide analyte is a chromophore because it can be detected by mere absorption of ultraviolet light.

At least one macrofluidic separation channel of the electrophoresis cassette contains a gel matrix composition. The gel matrix composition fills a volume of the macrofluidic separation channel. The gel matrix composition may also define at least one sample well within at least one sample well cavity.

Sample wells may have multiple geometries. The geometry of the sample well reflects the geometry of the sample well insert used to define the negative space not occupied by the gel matrix composition. In certain aspects of the disclosure, a sample well insert is used in combination with a stripper plate to create a terraced geometry, the negative space of which will form the sample well. Critically, the sample wells of the disclosure have the have a "chimney" shape, forming a "gel chimney," in which the walls of the sample well extend through the sample well insert opening and into the sample well port. The cover plate may be specifically adapted with walls surrounding the sample well insert opening to support the sides of a chimney-shaped sample well. The chimney-shaped sample well prevents entry of the sample into the seam between the upper surface of the gel and the bottom surface of the cassette cover plate. Such entry can occur by capillary flow or by electrophoresis. Sample molecules entering the seam travel at a different rate than that of sample molecules traveling through the gel. For this reason, undesired sample molecules traveling in the seam may be drawn into the elution chamber during elution, thereby contaminating the desired sample components that have been traveling through the gel. The contamination typically travels unpredictably, but often faster than the material traveling through the gel in the separation channel, causing inappropriately large molecules to enter the elution chamber.

At least one macrofluidic separation channel of the cassette contains a buffer composition. The buffer composition fills a volume of at least one of a first buffer reservoir, a second buffer reservoir, a negative elution reservoir, a positive elution reservoir, and a sample well.

Cassettes of the disclosure are compatible with a variety of detection instruments and systems. Contemplated detection systems and instruments may include an array of electrodes (FIG. 33, for example). Alternatively, cassettes of the disclosure may include an electrode array (FIGS. 22, 24, 25, and 26, for example). The integrated electrode array may include at least one of a negative separation electrode, a positive separation electrode, a negative elution electrode, and a positive elution electrode. Within the array, the at least one negative separation electrode is positioned within or adjacent to a first buffer reservoir and the at least one positive separation electrode is positioned within or adjacent to a second buffer reservoir. Within the array, the at least one negative elution electrode is positioned within or adjacent to a negative elution reservoir and the at least one positive elution electrode is positioned within or adjacent to a positive elution reservoir.

A cassette of the disclosure may further include a removable seal. Non-limiting examples of seal materials include polymers, adhesive films, and tapes. For example, the seal encloses at least one of an opening, a protrusion and a recess of a cover. Alternatively, or in addition, the seal encloses the entirety of the cassette. Functionally, the seal prevents spillage and evaporation of at least one buffer or at least one gel matrix composition contained within the cassette during storage. Moreover, the seal prevents the at least one buffer or at least one gel matrix composition contained within the cassette from contacting or corroding an electrode or electrode array of the cassette during storage.

Regardless of which features are present within the electrophoresis cassette, the cassette is disposable.

The disclosure also provides a method of making an electrophoresis cassette, including: providing an electrophoresis cassette of the disclosure, wherein the cassette further contains at least one of a first buffer reservoir insert, a second buffer reservoir insert, a sample well insert, a negative elution reservoir insert, a positive elution reservoir insert, an elution module and a cover, wherein the first buffer reservoir insert or second buffer reservoir insert includes a vent or an injection port, wherein the first buffer reservoir insert traverses an opening in the cover plate aligned with the first buffer reservoir, wherein the second buffer reservoir insert traverses an opening in the cover plate aligned with the second buffer reservoir, wherein the sample well insert traverses an opening in the cover plate aligned with a sample well cavity; inserting a gel matrix composition through the injection port; solidifying the gel matrix composition, wherein the gel matrix composition transforms from a liquid to a solid; removing the at least one of a first buffer reservoir insert, a second buffer reservoir insert, a sample well insert, a negative elution reservoir insert, and a positive elution reservoir insert, wherein a sample well is generated; filling a first buffer reservoir insert, a second buffer reservoir insert, a negative elution reservoir insert, and a positive elution reservoir insert with a buffer composition; filling at least one elution chamber with an elution buffer composition; and sealing the electrophoresis cassette.

In certain embodiments of this method of making an electrophoresis cassette, wherein the sample well insert traverses an opening in the cover plate aligned with the sample well cavity, the method includes the steps of inserting a gel matrix composition through an injection port; solidifying the gel matrix composition, wherein the gel matrix composition transforms from a liquid to a solid; removing the sample well insert, wherein a sample well is generated; filling the first buffer reservoir, second buffer reservoir, negative elution reservoir, and positive elution reservoir with a buffer composition; filling the elution module with an elution buffer composition; and sealing the electrophoresis cassette.

In certain embodiments of this method of making an electrophoresis cassette, the gel is cast in the electrophoresis cassette, without the use of a casting fixture, and the cassette is oriented or placed horizontally during the inserting and solidifying steps. Alternatively, the gel is cast in the electrophoresis cassette by using a casting fixture. For example, the method further includes the steps of: providing a casting fixture, wherein the fixture includes, a front plate that contacts the top of the cassette, wherein the front plate contains at least one opening that aligns with a vent positioned in either of the a buffer reservoir, a first buffer reservoir insert, a second buffer reservoir, or second buffer reservoir insert; a back plate that contacts the bottom of the cassette, wherein the back plate contains at least one opening; attaching the casting fixture to an electrophoresis cassette of the disclosure, wherein the back plate contacts the bottom of the electrophoresis cassette and the front plate contacts the top of the electrophoresis cassette, and wherein the back and front plates are attached to each other. The casting fixture is provided and attached prior to an injection of a liquid gel-matrix composition and the casting fixture is detached from the electrophoresis cassette prior to the removal of an insert following solidification of the gel-matrix composition.

With respect to a method of making an electrophoresis cassette of the disclosure, a first buffer reservoir insert fills a volume of a first buffer reservoir, a second buffer reservoir insert fills a volume of a second buffer reservoir, a negative elution reservoir insert fills a volume of a negative elution reservoir, and a positive elution reservoir insert fills a volume of a positive elution reservoir. Moreover, a sample well insert fills a volume of a sample well cavity.

An electrophoresis cassette or a casting fixture may be either horizontal or vertical during the gel casting procedure.

The disclosure also provides a detection system or instrument for detecting a property of a sample, or an analyte or fraction thereof within a separation channel of a cassette. For example, a cassette including at least one of a negative separation electrode, a positive separation electrode, a negative elution electrode and a positive elution electrode is inserted into an electrophoresis system. An electrophoresis system or instrument includes a detector positioned near the separation channel of the electrophoresis cassette, wherein the detector detects a property of a sample, an analyte, or a fraction; a processor configured to activate or deactivate power to at least one electrode based upon a signal received from the detector; and a power module including at least one of a power supply and a relay to provide power to the processor, at least one negative electrode and at least one positive electrode. The detection system or instrument detects a property of a sample, an analyte, or a fraction, relays the information to the processor, and in response to an instruction from the processor, deactivates at least one negative separation electrode and at least one positive separation electrode, and subsequently, activates at least one negative elution electrode and at least one positive elution electrode. Alternatively, or in addition, the detection system or instrument detects a property of a sample, an analyte, or a fraction or the absence of a signal, relays the information to the processor, and in response to an instruction from the processor, maintains all negative elution electrodes and all positive elution electrodes of the cassette in a deactivated state. The differential activation of separation versus elution electrodes ensures that the conductive path is concentrated in the separation channel.

An exemplary detection system or instrument of the disclosure is depicted in FIGS. 32 and 33. In these embodiments, the instrument of the disclosure contains at least one "nest" or holder for at least one side-eluting cassette of the disclosure. As shown in these figures, the instrument may comprise two nests or holders, each of which may contain a side-eluting cassette of the disclosure. In a preferred embodiment, exemplary instruments of the disclosure comprise at least one window aligned with at least one separation channel of at least one cassette. The window may also be aligned with a detector or an imaging device to detect or visualize a sample, analyte, fraction, or marker within at least one separation channel Preferably, the window is aligned with at least one separation channel in at least one cassette and at least one imaging device positioned within or integral to the instrument. Preferably, the window is aligned with the entirely of at least one separation channel, thereby, allowing the imaging device to visualize the entirety of the at least one separation channel Nonlimiting examples of the imaging device include a CCD imaging device (e.g. a CCD camera) and a light-emitting diodes (LED) imaging device.

In certain embodiments, the detector or imaging device within or integral to the instrument detects or images at least one mobility marker within the at least one separation channel. Exemplary mobility markers include, but are not limited to, detectable dyes or detectable microparticles. In certain embodiments, the detectable dyes or detectable microparticles are colored dyes or colored microparticles. In certain embodiments, the detectable dyes or detectable microparticles are fluorescent microparticles. Uncolored microparticles are also contemplated. Uncolored microparticles appear white to the naked eye and to a CCD or LED imaging device using white-light illumination. In certain embodiments, the detectable dyes or detectable microparticles are negatively or positively charged. Preferably, the detectable dyes or detectable microparticles are negatively charged. For example, negatively-charged microparticles may be used as mobility markers with samples comprising DNA. Preferably, when used as a mobility marker for DNA samples, the negatively-charged microparticles have a diameter in the range of 50-200 nanometers. Moreover, when used as a mobility marker for DNA samples, the negatively-charged microparticles traverse an agarose gel matrix composition, preferably having an agarose concentration in the range of 0.75% to 2% weight by volume.

The use of mobility markers permits the operator of the instrument to correct for variations between electrophoresis experiments by determining the run times of each experiment from the behavior of the mobility markers and equilibrating run times of each individual experiment according to the movement or run times of the mobility markers.

The detected property may be an optical property of an analyte. Exemplary optical properties include, but are not limited to, the emission or absorption of light. Furthermore, the detected property may include magnetism, radiation, temperature, color, energy, or changes in any of the above.

In an exemplary embodiment of the methods of the disclosure, the detector may include a camera that is connected to a processor. The processor may terminate the run upon a detectable agent reaching a desired position in the separation channel. The detectable agent may include, but is not limited to, bromothymal blue (dark blue color) and xylene cyanol (dark red color). In an aspect of this embodiment, the detectable agent traverses the separation channel with the sample, analyte, or fraction. Alternatively, or in addition, the detectable agent traverses the separation channel independently of the sample, analyte, or fraction. For instance, the detectable agent may run ahead or behind of a sample, analyte, or fraction. The detectable agent may be a detectable analyte or fraction of the sample.

Exemplary samples, analytes, or fractions of the disclosure may contain a detectable label, such as a magnetic, a paramagnetic, a radioactive, an enzymatic, an immunological, or an optical label. Non-limiting examples of optical labels are fluorescent and light-absorbing compounds. A sample, analyte, or fraction may contain a fluorescent compound. Optionally, the sample, analyte, or fraction forms a complex with the fluorescent compound. The fluorescent compound or the analyte may be a fluorophore. A sample, analyte, or fraction may contain a light-absorbing compound. Optionally, the sample, analyte, or fraction forms a complex with the light-absorbing compound. Alternatively, the light-absorbing compound or the analyte may be a chromophore.

The disclosure provides a method of fractionating analytes within a sample, including: providing an electrophoresis cassette described herein, wherein the cassette comprises at least one of a first buffer reservoir insert, a second buffer reservoir insert, a sample well insert, a negative elution reservoir insert, a positive elution reservoir insert, an elution module and a cover, wherein the first buffer reservoir insert or second buffer reservoir insert includes a vent or an injection port, wherein the first buffer reservoir insert traverses an opening in the cover plate aligned with the first buffer reservoir, wherein the second buffer reservoir insert traverses an opening in the cover plate aligned with the second buffer reservoir, wherein the sample well insert traverses an opening in the cover plate aligned with a sample well cavity; inserting a gel matrix composition through the injection port; solidifying the gel matrix composition, wherein the gel matrix composition transforms from a liquid to a solid; removing the at least one of a first buffer reservoir insert, a second buffer reservoir insert, a sample well insert, a negative elution reservoir insert, and a positive elution reservoir insert, wherein a sample well is generated; filling a first buffer reservoir insert, a second buffer reservoir insert, a negative elution reservoir insert, and a positive elution reservoir insert with a buffer composition; filling at least one elution chamber with an elution buffer composition; and inserting the electrophoresis cassette into a detection system described herein; programming a processor of the detection system to activate at least one of a negative separation electrode and at least one of a positive separation electrode, and to activate at least one of a negative elution electrode and at least one of a positive elution electrode when the processor determines that a sample, analyte, or fraction traversed the separation channel to a position aligned with an axis through the at least one of a negative elution electrode and the at least one of a positive elution electrode; applying the sample to the sample well; applying a voltage across the electrophoresis cassette; collecting analytes of the sample at least one elution chamber, thereby fractionating analytes within a sample.

In certain embodiments of this method of fractionating analytes within a sample, this method includes providing an electrophoresis cassette described herein, wherein a sample well insert traverses an opening in the cover plate aligned with a sample well cavity, the method includes the steps of inserting a gel matrix composition through an injection port; solidifying the gel matrix composition, wherein the gel matrix composition transforms from a liquid to a solid; removing the sample well insert, wherein a sample well is generated; filling the first buffer reservoir, second buffer reservoir, negative elution reservoir, and positive elution reservoir with a buffer composition; filling the elution module with an elution buffer composition; and inserting the electrophoresis cassette into a detection system of the disclosure.

In certain embodiments of this method of fractionating analytes within a sample, the gel is cast in the electrophoresis cassette, without the use of a casting fixture, and the cassette is oriented or placed horizontally during the inserting and solidifying steps. Alternatively, the gel is cast in the electrophoresis cassette by using a casting fixture. For example, the method further includes the steps of: providing a casting fixture, wherein the fixture includes, a front plate that contacts the top of the cassette, wherein the front plate contains at least one opening that aligns with a vent positioned in either of the a buffer reservoir, a first buffer reservoir insert, a second buffer reservoir insert, or second buffer reservoir insert; a back plate that contacts the bottom of the cassette, wherein the back plate contains at least one opening; attaching the casting fixture to an electrophoresis cassette of the disclosure, wherein the back plate contacts the bottom of the electrophoresis cassette and the front plate contacts the top of the electrophoresis cassette, and wherein the back and front plates are attached to each other. The casting fixture is provided and attached prior to an injection of a liquid gel-matrix composition and the casting fixture is detached from the electrophoresis cassette prior to the removal of an insert following solidification of the gel-matrix composition.

An exemplary sample, analyte, or fraction of the disclosure includes a polynucleic acid or a polypeptide. Moreover, a polynucleic acid may contain deoxyribonucleic acid (DNA) or ribonucleic acid (RNA). Alternatively, or in addition, a polynucleic acid may be double- or single stranded. A polypeptide may be native or denatured.

The sample may contain a detectable compound. Exemplary detectable compounds are magnetically-, paramagnetically-, radioactively-, enzymatically-, immunologically-, or optically-detectable. Optically-detectable compounds are, for example, fluorescent and light-absorbing compounds. A sample may contain at least one of a complex of an analyte and a fluorescent compound. The fluorescent compound may be a fluorophore. The analyte may be a fluorescent compound or fluorophore. Alternatively, or in addition, a sample may contain at least one of a complex of an analyte and a light-absorbing compound. In one embodiment, the light-absorbing compound may be a chromophore. In another embodiment, the analyte is a light-absorbing compound or chromophore.

At least one of a gel matrix composition, a buffer composition, or an elution buffer composition may include at least one of a fluorophore that complexes to at least one of an analyte. At least one of a gel matrix composition, a buffer composition, or an elution buffer composition may comprise at least one of a chromophore that complexes to at least one of an analyte.

BRIEF DESCRIPTION OF THE DRAWINGS

FIGS. 3A-B are schematic diagrams depicting exemplary separation channel dimensions of a cassette of the disclosure. In certain embodiments, the separation channel may be defined as the gel-matrix filled portion of the cassette. Exemplary gel matrix compositions of the disclosure include, but are not limited to, agarose and acrylamide. As shown in this figure, representing an embodiment of a cassette of the disclosure, a length of a separation channel may be about 103.65 mm. As shown in FIG. 3A, representing an embodiment of a cassette of the disclosure, a depth of a separation channel may be about 6.5 mm. As shown in this figure, representing an embodiment of a cassette of the disclosure, a width of a separation channel may be about 7.5 mm. As shown in this figure, representing an embodiment of a cassette of the disclosure, a cross-sectional area of a separation channel may be about 48.1 $mm^2$. As shown in this figure, representing an embodiment of a cassette of the disclosure, a volume or a total volume of a separation channel may be about 4985.6 µL. Depicted in FIG. 3B, is an exemplary sample well insert (e.g. comb). As shown here, the sample well insert is centered in the separation channel to leave space on all sides of the sample well insert. Thus, the sample well insert does not contact any portion of the separation channel itself. As a consequence, the sample loaded into the resultant sample well traverses the separation channel without contacting the sides or bottom of the separation channel.

FIGS. 17A-B are a pair of schematic drawings depicting an exemplary injection-molded side-eluting cassette with upside-down filling capabilities. The top view, FIG. 17A, of the exemplary cassette demonstrates exemplary positions for: one or more positive elution electrode ports (2) (in this particular example the arrow points to one of thirteen ports); one or more elution module ports (3) (in this particular example the arrow points to one of thirteen ports); one or more negative elution electrode ports (4) (in this particular example the arrow points to one of thirteen ports); one or more sample input wells (5) (in this particular example the arrow points to a singular sample well); one or more negative separation electrode ports (6) (in this particular example the arrow points to a singular negative separation electrode port); and one or more positive separation electrode ports (6) (in this particular example the arrow points to a singular positive separation electrode port). The bottom view, FIG. 17B, of the exemplary cassette demonstrates exemplary positions for one or more ports for inserting liquid gel matrix composition (1) (also referred to as inserting the gel into the separation channel or filling the separation channel) (in this particular example the arrow points to a singular port for inserting liquid gel matrix composition or a gel insertion port).

FIGS. 18A-B are a pair of schematic drawings depicting an exemplary injection-molded side-eluting cassette with upside-down filling capabilities. The top/interior view, FIG. 18A, of the top/interior surface of the cassette or cassette base demonstrates exemplary positions for: one or more negative buffer reservoir cavities corresponding to one or more separation channels (1) (in this particular example the arrow points to a singular negative buffer reservoir cavity corresponding to a singular separation channel); one or more positive buffer reservoir cavities corresponding to one or more separation channels (2) (in this particular example the arrow points to a singular positive buffer reservoir cavity corresponding to a singular separation channel); one or more negative buffer reservoir cavities corresponding to one or more negative elution channels (3) (in this particular example the arrow points to one of thirteen negative buffer reservoir cavities corresponding to one of thirteen negative elution channels); one or more positive buffer reservoir cavities corresponding to one or more positive elution channels (4) (in this particular example the arrow points to one of thirteen positive buffer reservoir cavities corresponding to one of thirteen positive elution channels); and one or more ports for inserting liquid gel matrix composition (8) (also referred to as inserting the gel into the separation channel or filling the separation channel) (in this particular example the arrow points to a singular port for inserting liquid gel matrix composition or a gel insertion port). The bottom/interior view, FIG. 18B, of the bottom/interior surface of the cassette or cassette top demonstrates exemplary positions for: one or more negative buffer reservoir cavities corresponding to one or more separation channels (1) (in this particular example the arrow points to a singular negative buffer reservoir cavity corresponding to a singular separation channel); one or more positive buffer reservoir cavities corresponding to one or more separation channels (2) (in this particular example the arrow points to a singular positive buffer reservoir cavity corresponding to a singular separation channel); one or more negative buffer reservoir cavities corresponding to one or more negative elution channels (3) (in this particular example the arrow points to one of thirteen negative buffer reservoir cavities corresponding to one of thirteen negative elution channels); one or more positive buffer reservoir cavities corresponding to one or more positive elution channels (4) (in this particular example the arrow points to one of thirteen positive buffer reservoir cavities corresponding to one of thirteen positive elution channels); one or more elution module strips (5) (in this particular example the arrow points to a singular elution module strip containing thirteen elution modules); one or more sample input wells or ports (6) (in this particular example the arrow points to a singular sample well port); and one or more separation channels (7) (in this particular example the arrow points to a singular separation channel).

FIG. 19 provides an alternative view of the cassette depicted in FIG. 18. The interior surfaces of the cassette base and top are shown in FIG. 19A and FIG. 19B, respectively. Specifically, this figure demonstrates an exemplary position of the elution module strip (5) as adjacent to a separation channel (7) (see bottom schematic).

FIGS. 22A-B are a pair of schematic drawings depicting an exemplary side-eluting cassette with printed electrodes. FIG. 22A depicts the top view of an exemplary assembled cassette. FIG. 22B depicts the top/interior view of an exemplary base unit of the exemplary cassette. The top/interior view of the exemplary base demonstrates exemplary positions for: at least one negative separation electrode (1); at least one negative elution electrode (2) (in this particular example the arrows point to the positions of thirteen negative elution electrodes); at least one positive elution electrode 3) (in this particular example the arrows point to the positions of thirteen positive elution electrodes); at least one positive separation electrode (4).

FIG. 25A is a top view of the exemplary electrode array. FIG. 25B is a view of the underside of the array depicted in FIG. 25A (the cassette-facing surface) of the exemplary electrode array. The combination of FIGS. 25A and 25B demonstrate exemplary positions for: at least one negative separation electrode; at least one positive separation electrode; at least one negative elution electrode (in this particular example the array contains thirteen negative elution electrodes); and at least one positive elution electrode (in this particular example the array contains thirteen positive elution electrodes).

In FIGS. 26A-B, the exemplary electrode array, FIG. 26A, is aligned with an exemplary cassette, FIG. 26B. In FIG. 26C, the exemplary electrode array and exemplary cassette are fit into place, and optionally, maintained in this arrangement by gravity or, alternatively, by a device such as an adhesive, a bonding agent, a clamp (or a pressure fit), a screw, etc.

FIG. 27A-C are a series of schematic drawings depicting an exemplary elution module strip formed by heat staking. FIGS. 27A-B illustrate an exemplary plastic elution chamber of an exemplary elution module strip either alone, FIG. 27A, or with one or more barriers or membranes heat sealed to a front and/or a rear face of one or more elution chambers within the elution module strip, FIG. 28B. FIG. 27C depicts a cross-section of the exemplary elution module chamber of the elution module strip having at least one barrier or membrane heat-sealed to a front and a rear face. FIGS. 27A-B demonstrate exemplary positions for: at least one elution chamber or module port, at least one elution chamber or module cavity, at least one barrier or membrane heat-sealed to a front face of the elution chamber or module, and at least one barrier or membrane heat-sealed to a rear face of the elution chamber or module.

FIG. 28 further illustrates the inclusion of at least one microporous membrane that is analyte-permeable and which faces at least one separation channel (the front face). FIG. 28 also illustrates the inclusion of at least one ultrafiltration membrane that is analyte-impermeable and which faces at least one elution channel reservoir (the rear face). The analyte-impermeable membrane permits the passage of ions, but prohibits the passage of analyte, thereby trapping the analyte within a sample collection chamber (also referred to as an elution cavity) within the elution module.

FIG. 29A, illustrates an exemplary gasket material for the elution module. The bottom panel, FIG. 29B, illustrates the inclusion of one or more membranes applied to the gasket material by an adhesive tape. The use of the adhesive or adhesive tape is simply one embodiment of this elution module. One or more membranes may be added to the exemplary elution module and maintained in position by any means, including, but not limited to gravity, a pressure fit with another element of the elution module or cassette, and heat sealing.

FIG. 35A is a schematic drawing depicting an alternative view of the cassette described in FIG. 34. In this drawing, the top and bottom plate (502 and 503, respectively) of the cassette shown in FIG. 34 are oriented such that the outer surface of the top plate (502) is directly facing the viewer.

FIG. 35B is a schematic drawing depicting an alternative view of the cassette described in FIG. 34. In this drawing, the top and bottom plates (502 and 503, respectively) of the cassette shown in FIG. 34 are oriented such that the outer surface of the bottom plate (502) is directly facing the viewer, and therefore, obscuring the top plate from view. The shaded region (512) shows an exemplary position for the at least one of a separation channel within a cassette of the disclosure. A solid gel matrix composition, optionally, in the form of column, is maintained within at least one of a separation channel that is contained either partially or completely (i.e. entirely) within an top plate of the cassette. As depicted in this figure, a separation channel including a solid gel matrix composition/column is entirely contained within the top plate of the cassette at the position labeled 512. Consequently, when an top plate of a cassette is configured as shown in this figure, a liquid gel matrix composition (for example, a liquid agarose composition) may be introduced (e.g. injected or poured) to the cassette through a port (513) located on the outside surface of the bottom plate, when the bottom plate is oriented on top of the bottom plate (i.e., "upside down"). Once a liquid gel matrix composition has solidified within a separation channel of the cassette, the port (513) may be sealed with, for example, an adhesive tape.

FIG. 41A is a schematic drawing depicting a cross-sectional view through the cassette described in FIG. 34 at the level of line A, as shown in FIG. 39. The shaded area of this cassette represents the area that may be occupied by a buffer composition.

FIG. 41B is a schematic drawing depicting a cross-sectional view through the cassette described in FIG. 34 at the level of line B, as shown in FIG. 39. The light grey shaded area of this cassette represents the portion of the cassette that may be occupied by a buffer composition. The dark grey shaded area of this cassette represents the portion of the cassette that may be occupied by a gel matrix composition (e.g. an agarose gel matrix composition).

FIG. 41C is a schematic drawing depicting a cross-sectional view through the cassette described in FIG. 34 at the level of line C, as shown in FIG. 39. The light grey shaded area of this cassette represents the portion of the cassette that may be occupied by a buffer composition. The dark grey shaded area of this cassette represents the portion of the cassette that may be occupied by a gel matrix composition (e.g. an agarose gel matrix composition).

FIG. 41D is a schematic drawing depicting a cross-sectional view through the cassette described in FIG. 34 at the level of line D, as shown in FIG. 39. The light grey shaded area of this cassette represents the portion of the cassette that may be occupied by a buffer composition. The dark grey shaded area of this cassette represents the portion of the cassette that may be occupied by a gel matrix composition (e.g. an agarose gel matrix composition).

FIG. 41E is a schematic drawing depicting a cross-sectional view through the cassette described in FIG. 34 at the level of line E, as shown in FIG. 39. The light grey shaded area of this cassette represents the portion of the cassette that may be occupied by a buffer composition. The dark grey shaded area of this cassette represents the portion of the cassette that may be occupied by a gel matrix composition (e.g. an agarose gel matrix composition).

FIG. 41F is a schematic drawing depicting a cross-sectional view through the cassette described in FIG. 34 at the level of line F, as shown in FIG. 39. The light grey shaded area of this cassette represents the portion of the cassette that may be occupied by a buffer composition. The dark grey shaded area of this cassette represents the portion of the cassette that may be occupied by a gel matrix composition (e.g. an agarose gel matrix composition).

FIGS. 48A-D are schematic drawings (lid bottom view, FIG. 48A; lid perspective view, FIG. 48B; cassette perspective view, FIG. 48C; assembled side view lid with cassette, FIG. 48D), depicting an exemplary fit of separation electrodes operably-linked to a lid of an exemplary instrument of the disclosure (as shown in, for example, FIGS. 47, 51, and 52) into an exemplary cassette of the disclosure during a separation electrophoresis.

FIGS. 50A-D are schematic drawings (lid bottom view, FIG. 50A; lid perspective view, FIG. 50B; cassette perspective view, FIG. 50C; assembled side view lid with cassette, FIG. 50D), depicting an exemplary fit of elution electrodes operably-linked to a lid of an exemplary instrument of the disclosure (as shown in, for example, FIGS. 49, 51, and 52) into an exemplary cassette of the disclosure during an elution electrophoresis.

FIG. 52B, depicts an initial position of the nest elevator. The middle panel, FIG. 52C, depicts a first elevated position of the nest elevator at which at least one separation electrode enters the cassette through at least one port within the outer surface of the top plate of the cassette. The nest elevator may reside at this first elevated position during separation electrophoresis. The bottom panel, FIG. 52D, depicts a second elevated position of the nest elevator at which at least one separation electrode and at least one elution electrode enters the cassette through at least one port or elution electrode channel within the outer surface of the top plate of the cassette. The nest elevator may reside at this second elevated position during elution electrophoresis.

DETAILED DESCRIPTION

This disclosure provides cassettes and methods for separating a single sample into multiple fractions of various sizes in a single preparative electrophoresis process.

Using the cassettes and methods of the disclosure, a separation electrophoresis process is performed first. The duration of separation electrophoresis may be manipulated or optimized to selectively process input samples that include, for instance, analytes or fractions of different size ranges or different ranges of electrophoretic mobility.

Following the initial separation step, an elution electrophoresis step is performed using a symmetrical array of negative and positive elution channels or reservoirs that reside on either side of the separation channel Elution products are collected in at least one elution module, and preferably a plurality of elution modules, each located within or adjacent to at least one positive elution reservoir, where the size-fractionated analytes migrate during elution electrophoresis.

The side-eluting cassettes of the disclosure elute and fractionate the contents of the separation channel in a parallel, as opposed to a serial, manner Parallel elution is accomplished by an elution step, wherein the contents of the separation channel move in a direction that is orthogonal or perpendicular to the direction in which the analytes move during a prior separation step.

Analytes of the disclosure include charged molecules that can be separated by electrophoresis. For example, DNA and SDS-treated proteins may be electrophoretically separated at least in part on the basis of molecular size. With respect to native proteins applied to a non-denaturing gel matrix composition, electrophoretic separation may be determined by a set of characteristics including, but not limited to, gel matrix composition and density, net charge of the analyte, molecular size of the analyte, and/or analyte shape characteristics. Cassettes and methods of the disclosure may separate samples or analytes on the basis of one or more of the foregoing characteristics.

Electrophoresis separates biomolecules by charge and/or size via mobility through a separating matrix in the presence of an electric field. Elution electrodes are not connected or activated during the separation process. Rather, elution electrodes are connected or activated once the sample or analytes in the separation channel are ready for elution. The timing of the connection or activation of elution electrodes ensures that the conductive path is concentrated down the separation channel during the separation process. For example, if the elution electrodes were connected to each other during the separation run, the elution electrodes would create a conductive path that, in turn, would induce strong field lines along the edge of the separation channel.

Figure 7:
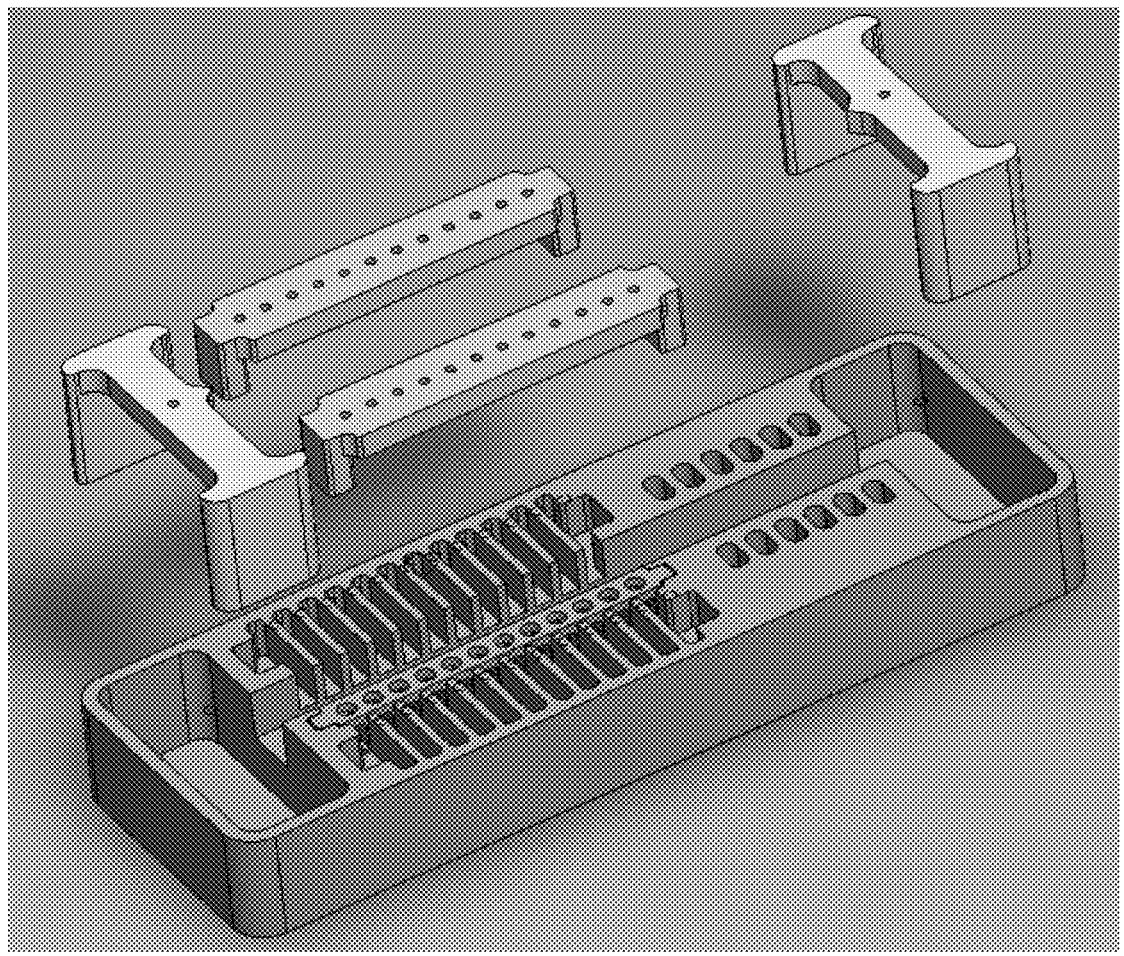
FIG. 7 is a schematic diagram depicting an exploded view of the alignment of at least one fixture for holding an elution electrode in position. The fixtures depicted align, from right to left, with a first buffer reservoir; alternatively, or in combination, at least one negative elution reservoir and at least one positive elution reservoir; and a second buffer reservoir. In certain embodiments, a platinum wire is threaded through the holes depicted in the fixtures and into the corresponding reservoirs below. The fixtures may be maintained in position through the use of an adhesive, such as glue.
Figure 8:
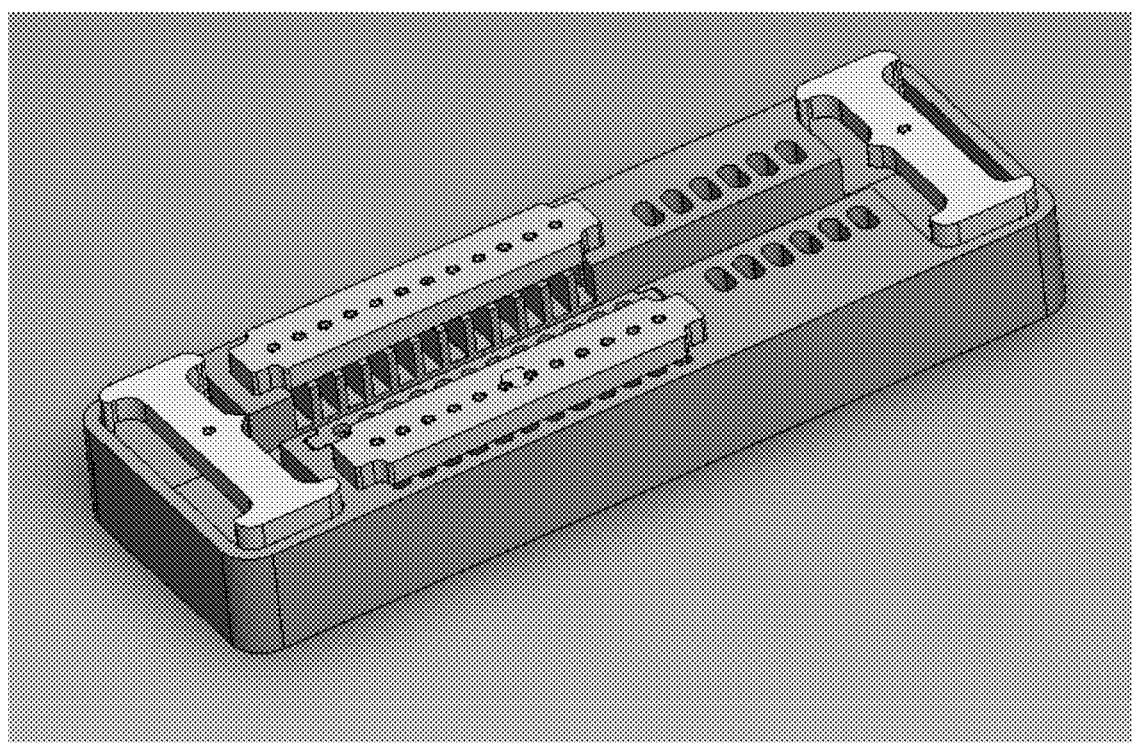
FIG. 8 is a schematic diagram depicting an assembled view of the alignment of at least one fixture for holding an elution electrode in position. The fixtures depicted align, from right to left, with a first buffer reservoir; alternatively, or in combination, at least one negative elution reservoir and at least one positive elution reservoir; and a second buffer reservoir.
Figure 43:
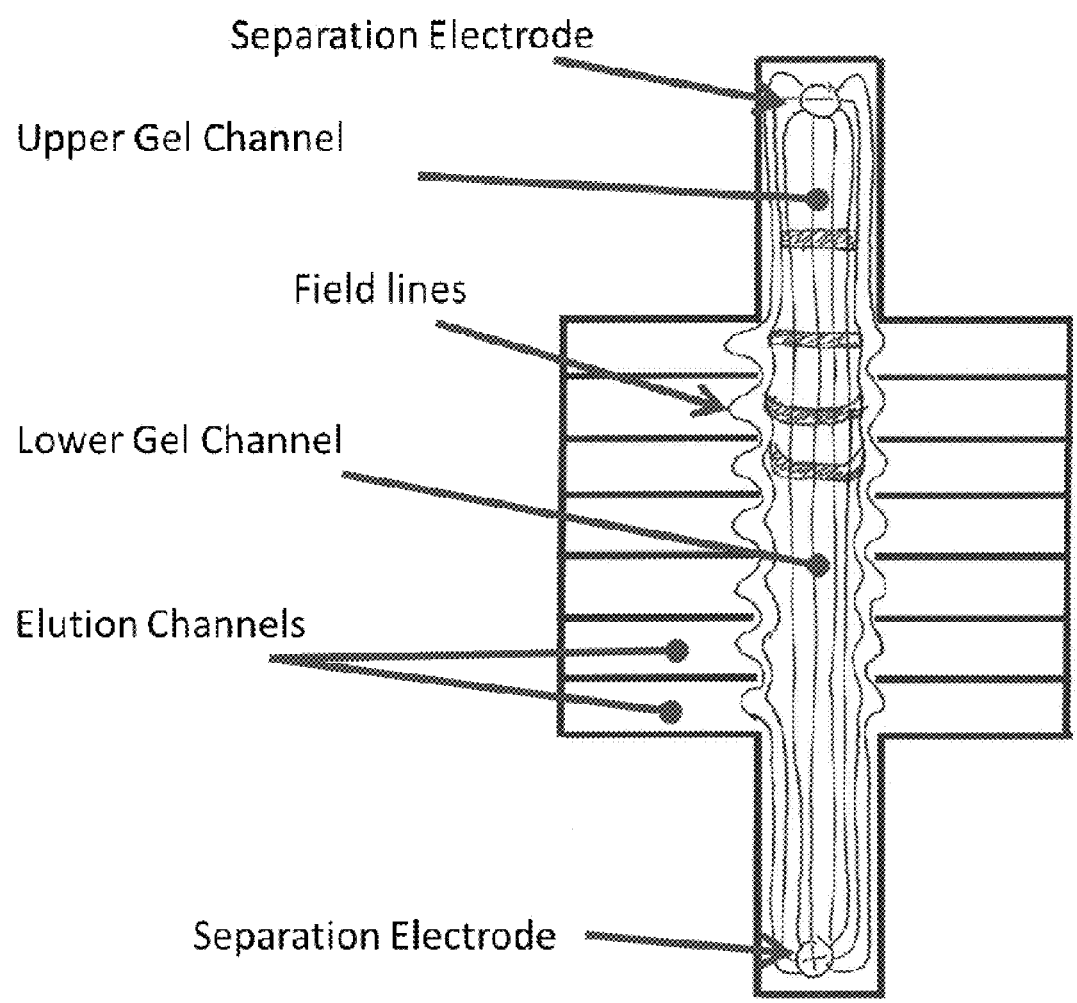
FIG. 43 is a schematic drawing depicting electric field lines in a cassette having a configuration similar to the configuration depicted in, for example, FIGS. 7, 17, and 18.

FIG. 43 illustrates electrophoretic field lines during separation electrophoresis in the exemplary cassette depicted in, for example, FIGS. 7, 17, and 18. As shown in FIG. 43, a sample travels down an upper portion of a separation channel and into a lower portion of the separation channel, where the lower portion of the separation channel intersects at least one elution channel Along the upper portion of a separation channel, the sample travels along field lines, which are perpendicular to lines of iso-potential; however, within the upper portion of a separation channel, the sample also diffuses. Within the upper portion of a separation channel field lines are substantially parallel because this portion of the separation channel is substantially straight with insulating walls. In contrast to the upper portion, the lower portion of a separation channel, the walls of the separation channel are bounded on one side by at least one negative elution channel/reservoir and on the other side, by at least one positive elution channel/reservoir. Optimally, the sample or fractions thereof should progress evenly along the lower portion of the separation channel without deformation. However, as shown in FIG. 43, the field lines on the edges of the lower portion of the separation channel are not substantially straight, but rather, form waves. The wavy field lines create a longer path as well as a weaker gradient at the lateral edges of the separation channel, causing the portion of the sample or fraction thereof that travels along these wavy field lines to traverse the separation channel at a decreased rate when compared to the portion of the sample or fraction thereof that travels along the substantially straight field lines in the center of the separation channel Diffusion of the sample or a fraction thereof may further exacerbate the band deformation effect caused by variable field line forms across the width of the lower portion of the separation channel, causing the sample or fraction hereof to broaden into the wavy, and slower-moving, field lines.

Figure 44:
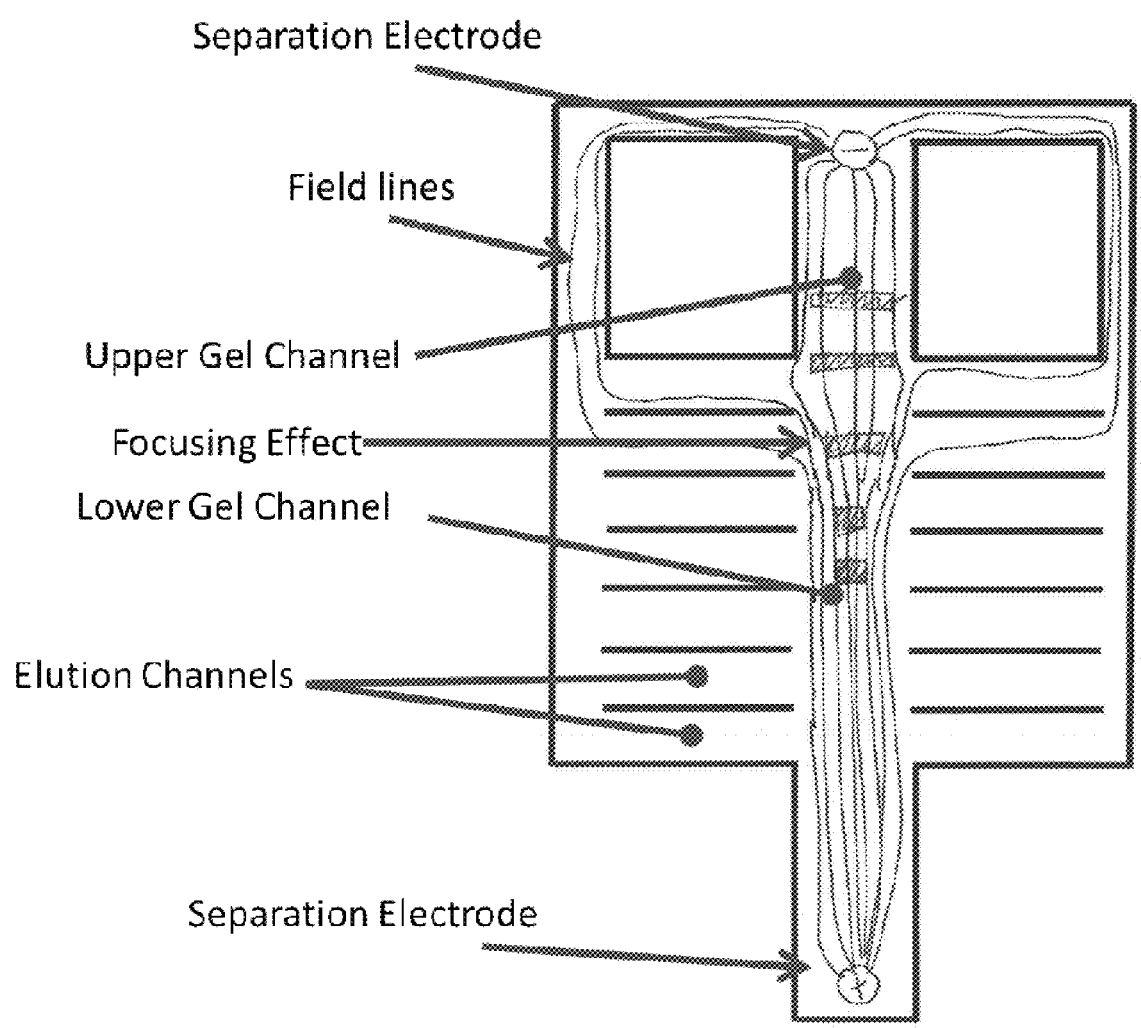
FIG. 44 is a schematic drawing depicting electric field lines in a cassette having a configuration similar to the configuration depicted in any one of FIGS. 34-52.

Cassettes of the disclosure focus the electric field to overcome diffusion of the sample during separation electrophoresis. For example, the embodiments of the cassettes of the disclosure described in FIGS. 34-52 use an electrophoretic focusing mechanism to control band spreading and deformation along a lower portion of a separation channel (as illustrated in FIG. 44). In these embodiments, the elution electrode channels (510 and 511) create an alternate electrical path between the at least one positive and at least one negative separation electrodes. This alternative electric path allows electrophoretic field lines to travel inward from the elution electrode channels through the elution reservoirs and into the separation channel. The inward-traveling field lines focus the sample or fraction thereof and keep the separated bands on the substantially straight field lines that run along the center of the separation channel (see, for example, FIG. 45).

Figure 46:
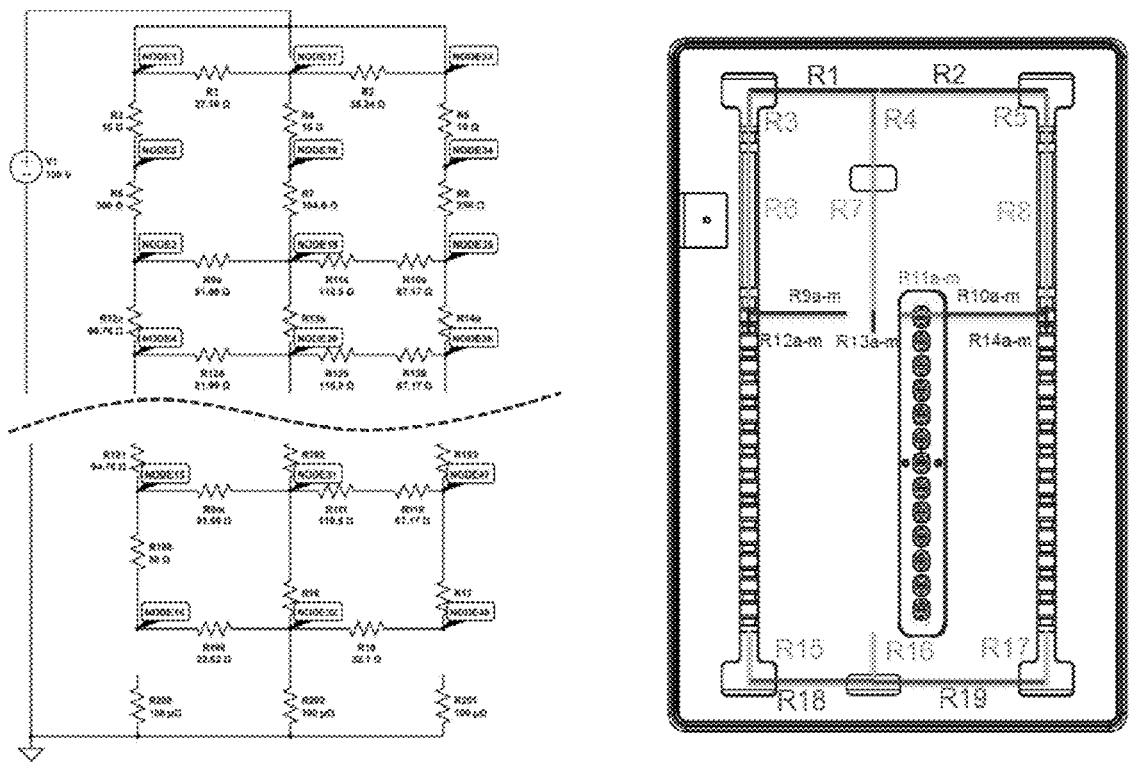
FIGS. 46A-B are schematic drawings depicting a resistive electrical model for designing a cassette of the disclosure, as depicted, for example, in FIGS. 34-52.
Figure 47A:
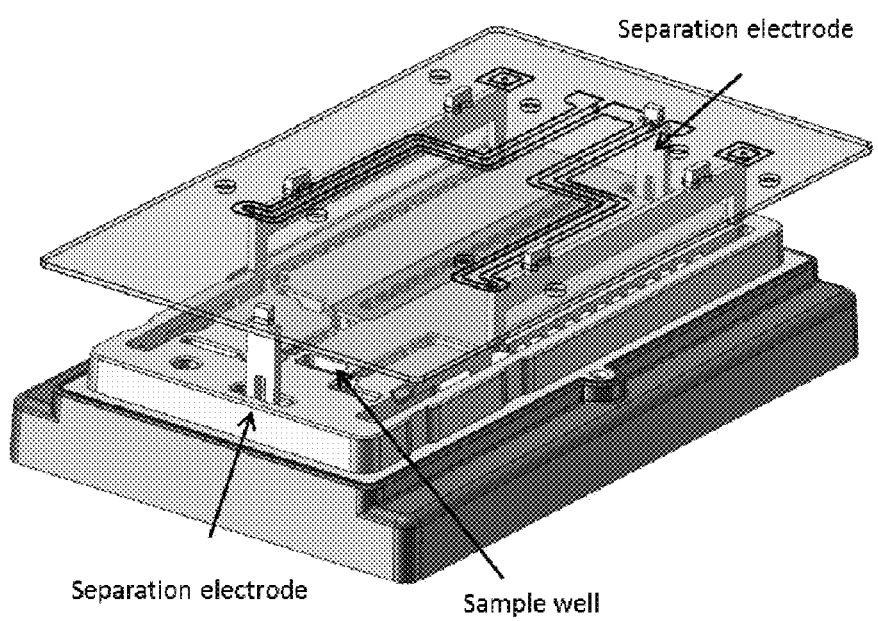
FIG. 47A is a schematic drawing depicting an exemplary configuration of separation electrodes operably-linked to a lid of an exemplary instrument of the disclosure (as shown in, for example, FIGS. 48, 51, and 52) during a separation electrophoresis. During separation electrophoresis, the separation electrodes are powered, generating an electric field aligned with a separation channel of the cassette. The electric current generated during separation electrophoresis drives or pulls the sample or a fraction thereof along the length of the separation channel in preparation for a subsequent elution electrophoresis.
Figure 47B:
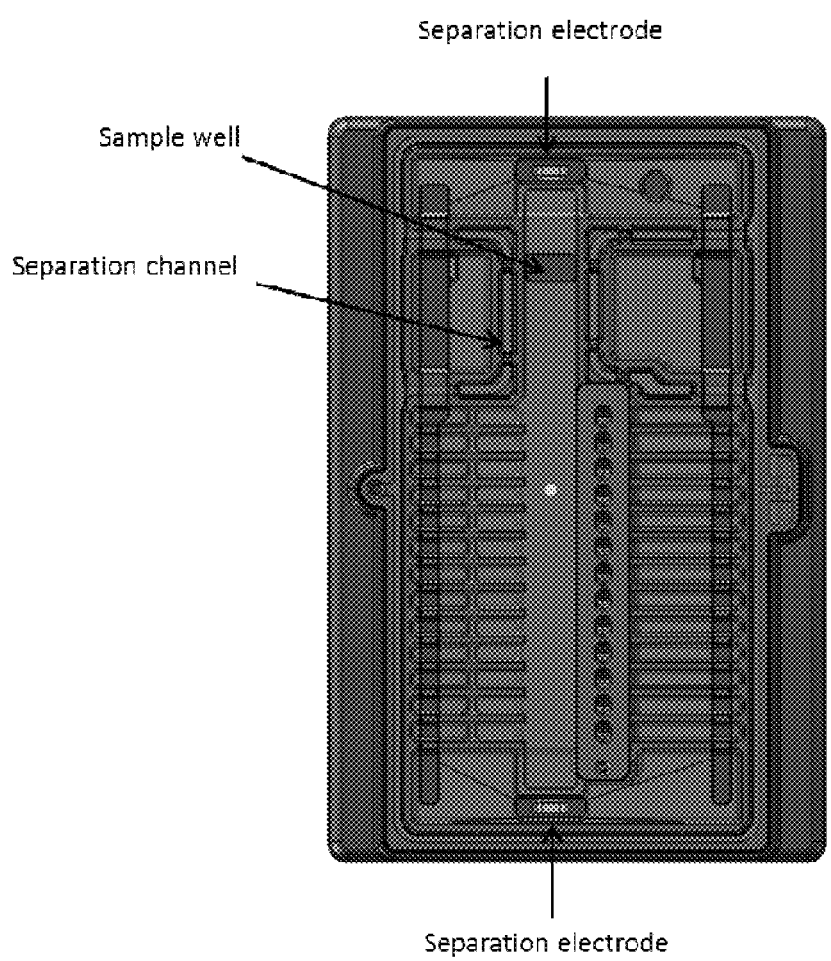
FIG. 47B is a schematic drawing depicting an alternate view of the configuration depicted in FIG. 47A. In this drawing, the cassette is shown from the perspective of a direct view of the outside of the top plate of the cassette.
Figure 49A:
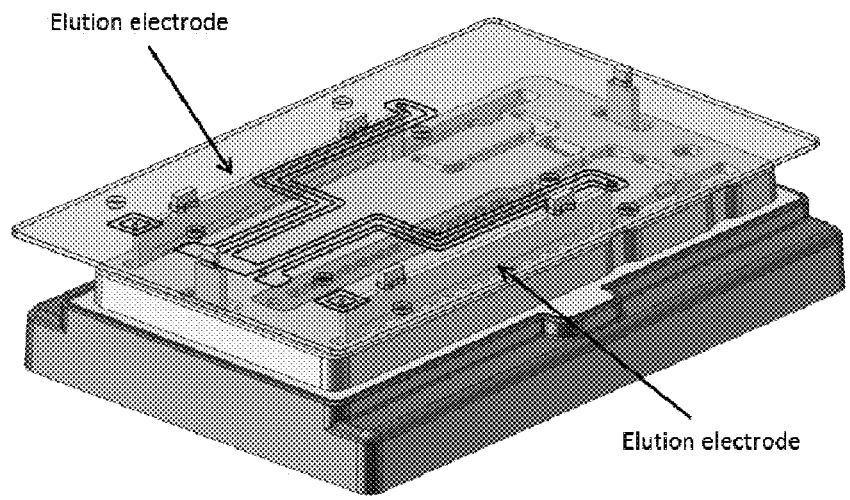
FIG. 49A is a schematic drawing depicting an exemplary configuration of elution electrodes operably-linked to a lid of an exemplary instrument of the disclosure (as shown in, for example, FIGS. 50, 51, and 52) during an elution electrophoresis. During elution electrophoresis, power to the separation electrodes is discontinued, the elution electrodes may be lowered into a cassette (or, alternatively, the cassette may be raised towards the elution electrode until the elution electrode resides within an elution electrode channel of the cassette), and power is provided to the elution electrodes, thereby generating an electric field across the cassette that drives or pulls the sample or a fraction thereof from a separation channel into at least one elution channel/reservoir.
Figure 49B:
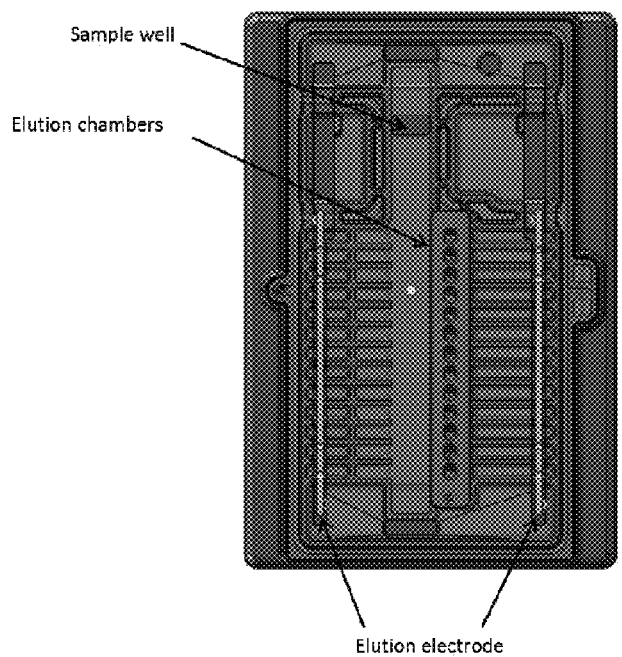
FIG. 49B is a schematic drawing depicting an alternate view of the configuration depicted in FIG. 49A. In this drawing, the cassette is shown from the perspective of a direct view of the outside of the top plate of the cassette.

This focusing effect may be calculated for alternative embodiments of the cassettes depicted in FIGS. 34-52 using resistive modeling. The resistance of a segment of a fluid or gel may be described by the formula:

$$R = \rho \frac{l}{A},$$

where ρ (rho) is the electrical resistivity of the fluid or gel, l is the length of the segment and A is the cross-sectional area of the segment. The network of resistors can be solved using standard network equations, as illustrated in FIG. 46. The network can be tuned until the field lines, represented by current in the simulation, added to the center section via the elution channels, focus the sample to overcome diffusion and/or electrophoretic distortion of field lines.

Finite element techniques may be used to model the resistive network. These methods may be used to simulate the resistive network, or a portion thereof, to alter and/or improve the design of the system. The use of finite element techniques is particularly advantageous when large end effects are present. For example, large end effects may be present in a portion of the network having a significant change in the cross sectional area of that portion.

Figure 45:
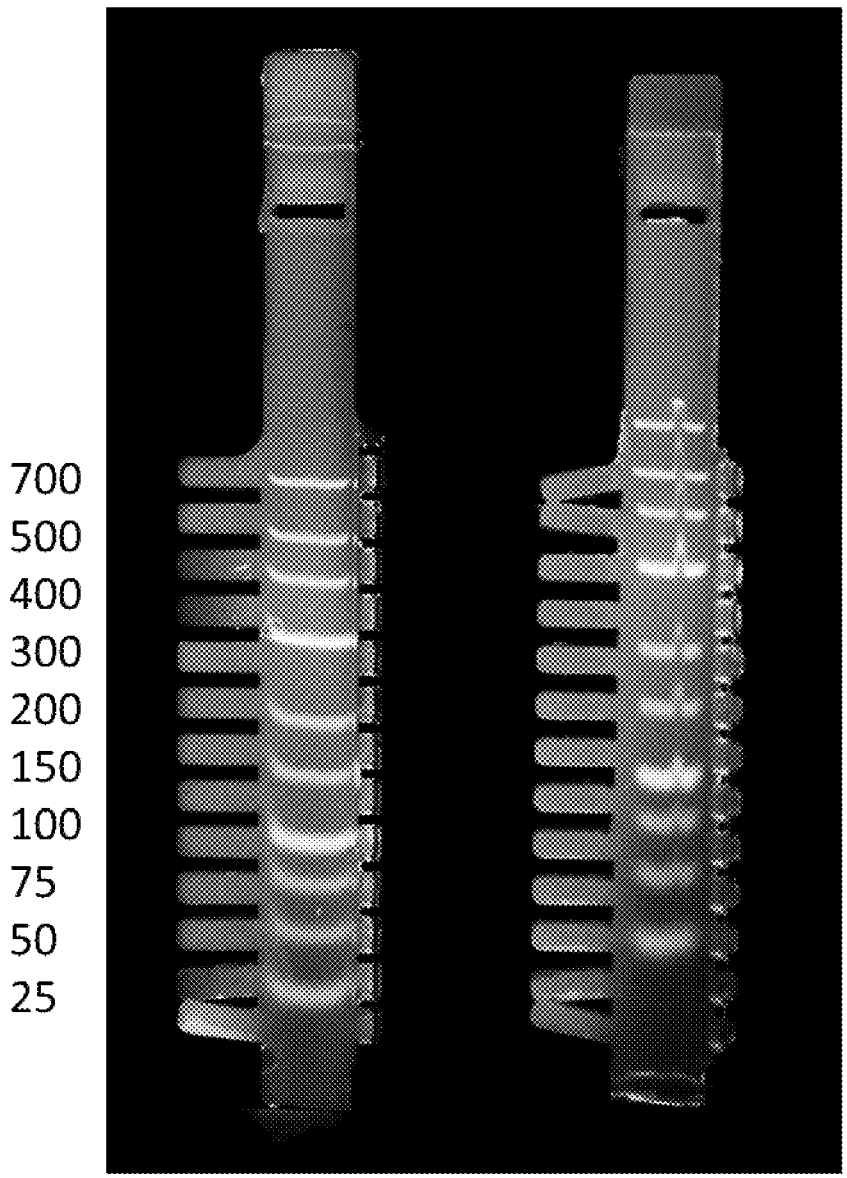
FIG. 45 is a photograph showing two gel matrix compositions isolated from a cassette of the disclosure following separation electrophoresis and staining to highlight the DNA marker contained within each gel. Cassettes of the disclosure use an electrophoretic focusing mechanism to control band spreading and deformation along a lower portion of a separation channel (as illustrated in FIG. 44). The gels provided in this drawing further illustrate this electrophoretic focusing principle. Sample of DNA markers were subjected to separation electrophoresis in cassette embodiments similar to that shown in FIGS. 34-42. The elution electrode channels of the two cassette embodiments had a different cross-sectional area, whereas the separation channels of the cassettes had the same geometry. Following separation electrophoresis, each of the cassettes was disassembled, the separation gel was stained with ethidium bromide, and the separation gel was photographed under UV illumination. The geometry of the elution channel geometry of the cassette shown at the left caused the DNA bands to broaden as they traversed the separation channel. This type of broadening may cause contamination of the elution modules during separation electrophoresis. In contrast, the cassette used for the gel shown on the right has a different elution electrode channel geometry. Consequently, the DNA marker bands on the right narrow as they traversed the separation channel. This narrowing/focusing shown on the right is preferred to the broadening shown on the left of because it narrowing/focusing minimizes elution module contamination during separation electrophoresis.

An example of this electrophoretic focusing principle is shown in FIG. 45, depicting the result of a separation electrophoresis of identical DNA markers, performed using two versions of a cassette. The elution electrode channels of these cassette embodiments have a different cross-sectional area. The separation channel of each cassette has the same cross-sectional areas. Following separation electrophoresis, each of the cassettes was disassembled, the separation gel was stained with ethidium bromide, and the separation gel was photographed under UV illumination. As shown in FIG. 45, the 54 DNA bands of the gel shown on the left broadened as they traversed the separation channel, extending all the way out to the edges of the separation channel. This type of broadening may cause contamination of the elution modules during separation electrophoresis. In contrast, the cassette used for the gel shown on the right has a different elution electrode channel cross-section. Consequently, the DNA marker bands on the right narrow as they traversed the separation channel. This narrowing/focusing shown on the right is preferred to the broadening shown on the left of FIG. 45 because it narrowing/focusing minimizes elution module contamination during separation electrophoresis. However, severe narrowing may adversely affect electrophoretic resolution during separation. FIGS. 39-42 provide cross-sectional views of an exemplary cassette having advantageous separation and elution channel design.

Figure 34:
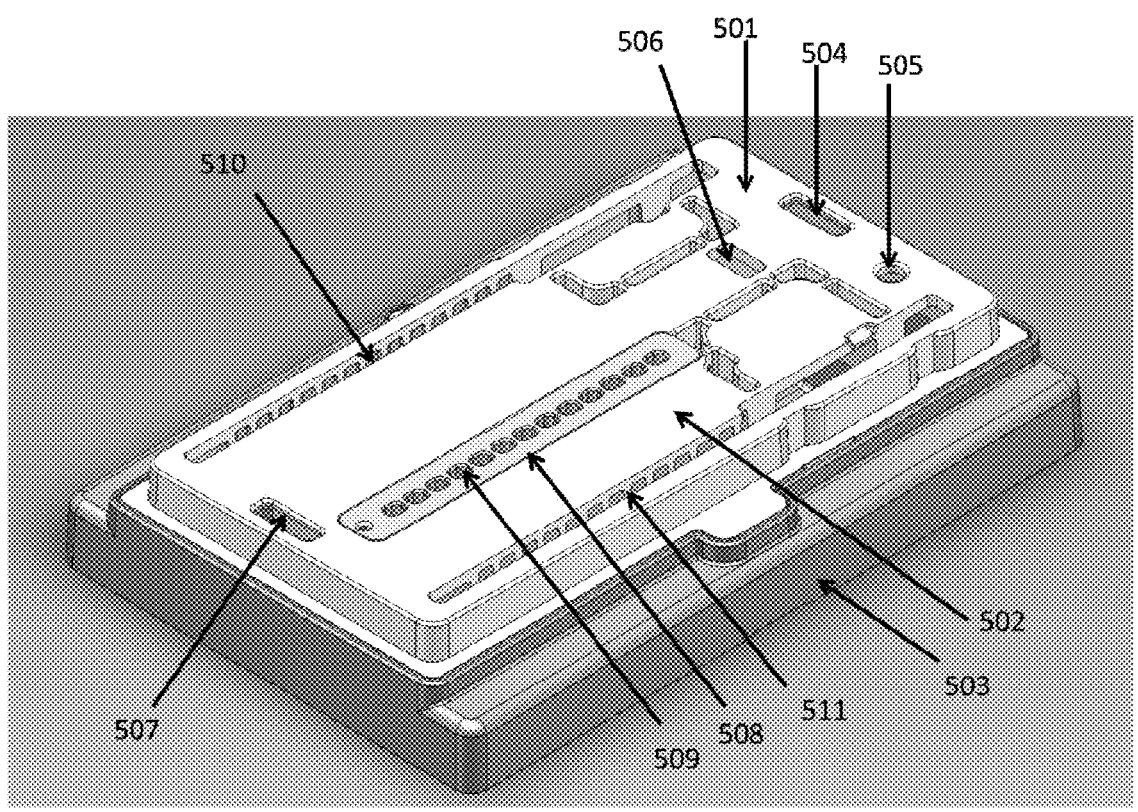
FIG. 34 is a schematic drawing depicting an exemplary electrophoresis cassette (501) having lateral electrode channels (510 and 511). This exemplary cassette (501) includes at least one of a top (502) and a bottom (503) plate, which may be injection-molded (using, for example, a plastic) and, alternatively or in addition, may be combined and adhered to one another (e.g. adhered to one another, for example, by a glue or a UV-curable glue). In alternate embodiments, the top (502) and bottom (503) plates may be assembled by other means, including, but not limited to, ultrasonic welding. Separation electrodes may be introduced into one or more of an upper buffer reservoir (504) and a lower buffer reservoir (507) through at least one of a port located at opposite ends of the cassette. An elution electrode may be introduced into the cassette through one or more buffer channel(s) on, for example, a left and/or a right side of the cassette (left and right directions as viewed from the outside surface of the top plate). Elution electrodes of a cassette of the disclosure may comprise, for example, elongated forms of platinum wire, which are introduced into the cassette through one or more buffer channel(s) on, for example, a left and/or a right side of the cassette (left and right directions as viewed from the outside surface of the top plate). On each side (e.g. left (510) and right (511)), one or more elution electrode channel(s) may connect at least one of an outer edge of each elution channel, an buffer reservoir (upper and/or lower), and/or any additional buffer reservoirs (for example, see features 530 and 531 of FIGS. 37 and 38). When a cassette of the disclosure contains one or more of the electrode channels depicted here (510 and 511), two wire electrodes are sufficient to drive an elution electrophoresis in each and every one of the elution channels (13 elution channels are depicted in this exemplary drawing). Other features of an exemplary cassette of the description that are provided in this drawing include an elution module strip (508), having a number of separate elution chambers the number of which corresponds to the number of elution channels present in the cassette (13 elution modules corresponding to 13 elution channels are depicted in this example). The elution channels may be accessed through at least one elution port (509), the number of which corresponds to the number of elution chambers present in the cassette (13 elution ports corresponding to 13 elution chambers are depicted in this example). A cassette of the disclosure, including this depiction, may contain at least one of a sample port (506) for introducing a sample through the sample port and into at least one of a sample well formed within at least one separation channel Cassettes of the disclosure may be at least partially, and optionally, completely filled with a buffer composition during delivery/shipping. Before use, an amount of buffer composition may be extracted or removed through a port (505) in the top plate, thereby, providing space for any bubbles or foam that may be generated by the one or more electrodes (separation electrodes and/or elution electrodes) to dissipate without, for example, overflowing the electrode-containing ports, reservoirs and/or channels.
Figure 36:
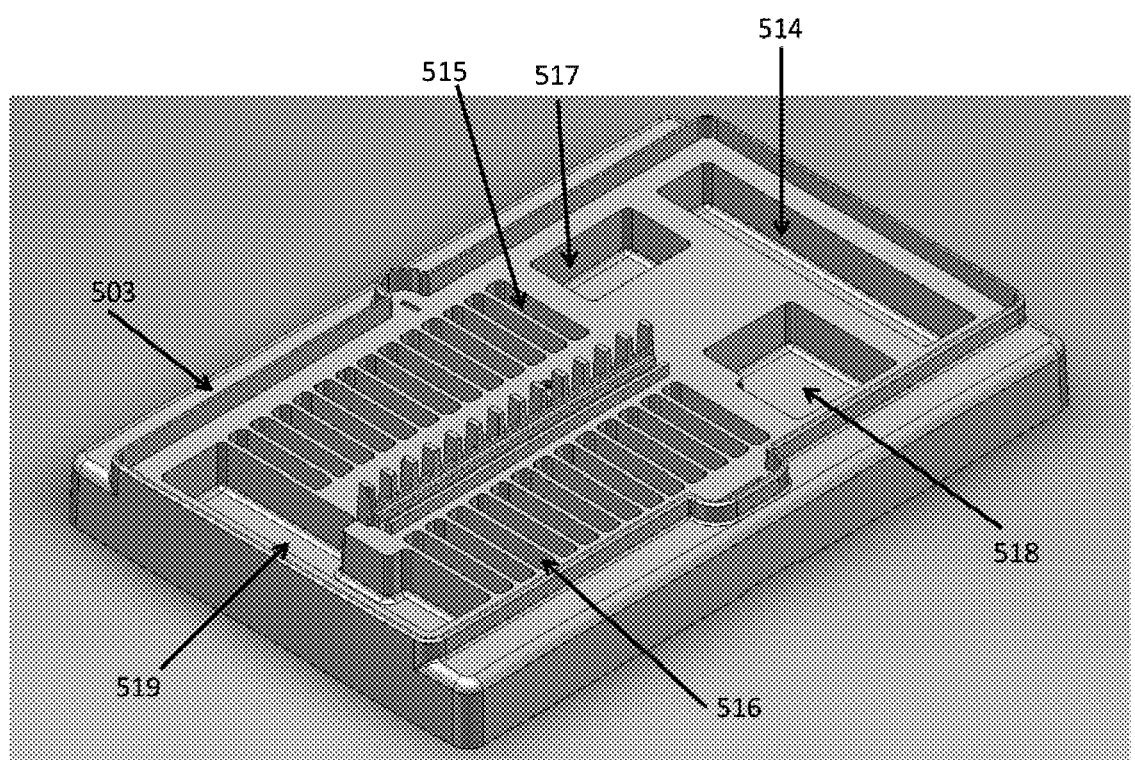
FIG. 36 is a schematic drawing depicting an alternative view of the cassette described in FIG. 34. In this drawing, the inner surface of the bottom plate of the cassette is exposed. In this exemplary embodiment, the bottom plate of the cassette (503) contains one or more cavities or reservoirs for holding a buffer composition (e.g. 514 through 519). Feature 514 comprises a part or an entirety of an upper buffer reservoir. Feature 519 comprises a part or an entirety of a lower buffer reservoir. Feature 515 comprises a part or an entirety of a "left" elution buffer reservoir. Feature 516 comprises a part or an entirety of a "right" elution buffer reservoir. Feature 517 comprises a part or an entirety of a "left" extra buffer reservoir. Feature 518 comprises a part or an entirety of a "right" extra buffer reservoir. As used to describe the drawing of this cassette, the labels left and right are applied to the bottom plate of the electrode from the perspective of directly viewing the inner surface of the bottom plate when feature 514 is upward. "Extra" buffer reservoirs (517 and 518) may be used to trap or collect foam or bubbles generated by one or more electrodes during electrophoresis.
Figure 37:
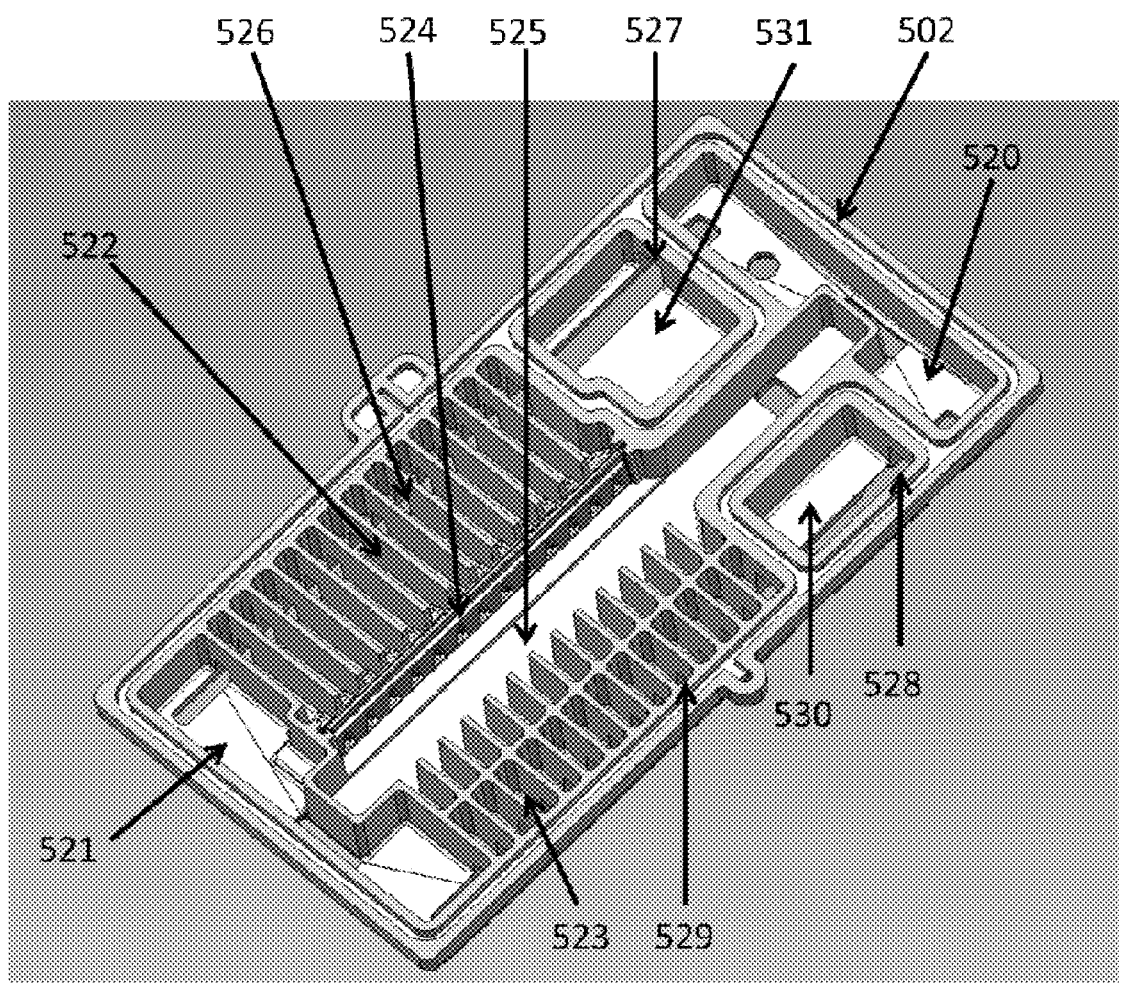
FIG. 37 is a schematic drawing depicting an alternative view of the cassette described in FIG. 34. In this drawing, the inner surface of the top plate of the cassette is exposed. In this exemplary embodiment, the top plate of the cassette (502) contains at least one of a separation channel (525). Separation channels of the cassettes of the disclosure are microfluidic. Separation channels of the cassettes of the disclosure may include either a liquid or solid gel matrix composition (e.g. agarose or acrylamide gel matrices). As shown in this exemplary embodiment, a separation channel may be bounded on the right side by an elution module strip (524) (containing at least one elution module or chamber). Feature 520 comprises a part or an entirety of an upper buffer reservoir. Feature 521 comprises a part or an entirety of a lower buffer reservoir. Feature 523 comprises a part or an entirety of a "left" elution buffer reservoir. Feature 522 comprises a part or an entirety of a "right" elution buffer reservoir. Feature 530 comprises a part or an entirety of a "left" extra buffer reservoir. Feature 531 comprises a part or an entirety of a "right" extra buffer reservoir. As used to describe the drawing of this cassette, the labels left and right are applied to the top plate of the electrode from the perspective of directly viewing the outer surface of the top plate when feature 520 is upward. "Extra" buffer reservoirs (530 and 531) may be used to trap or collect foam or bubbles generated by one or more electrodes during electrophoresis.
Figure 38:
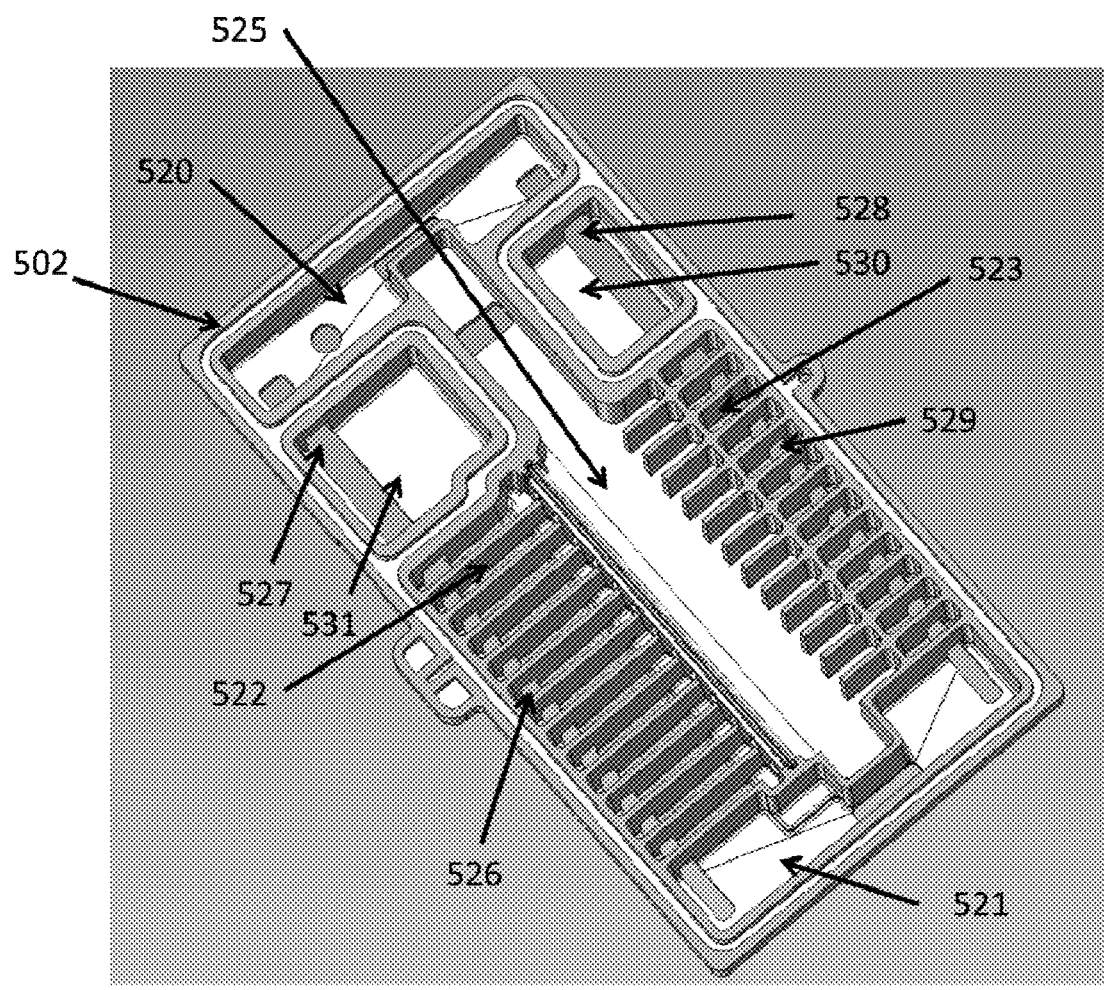
FIG. 38 is a schematic drawing depicting an alternative view of the cassette described in FIG. 34. In this drawing, the inner surface of the top plate of the cassette is exposed.
Figure 39:
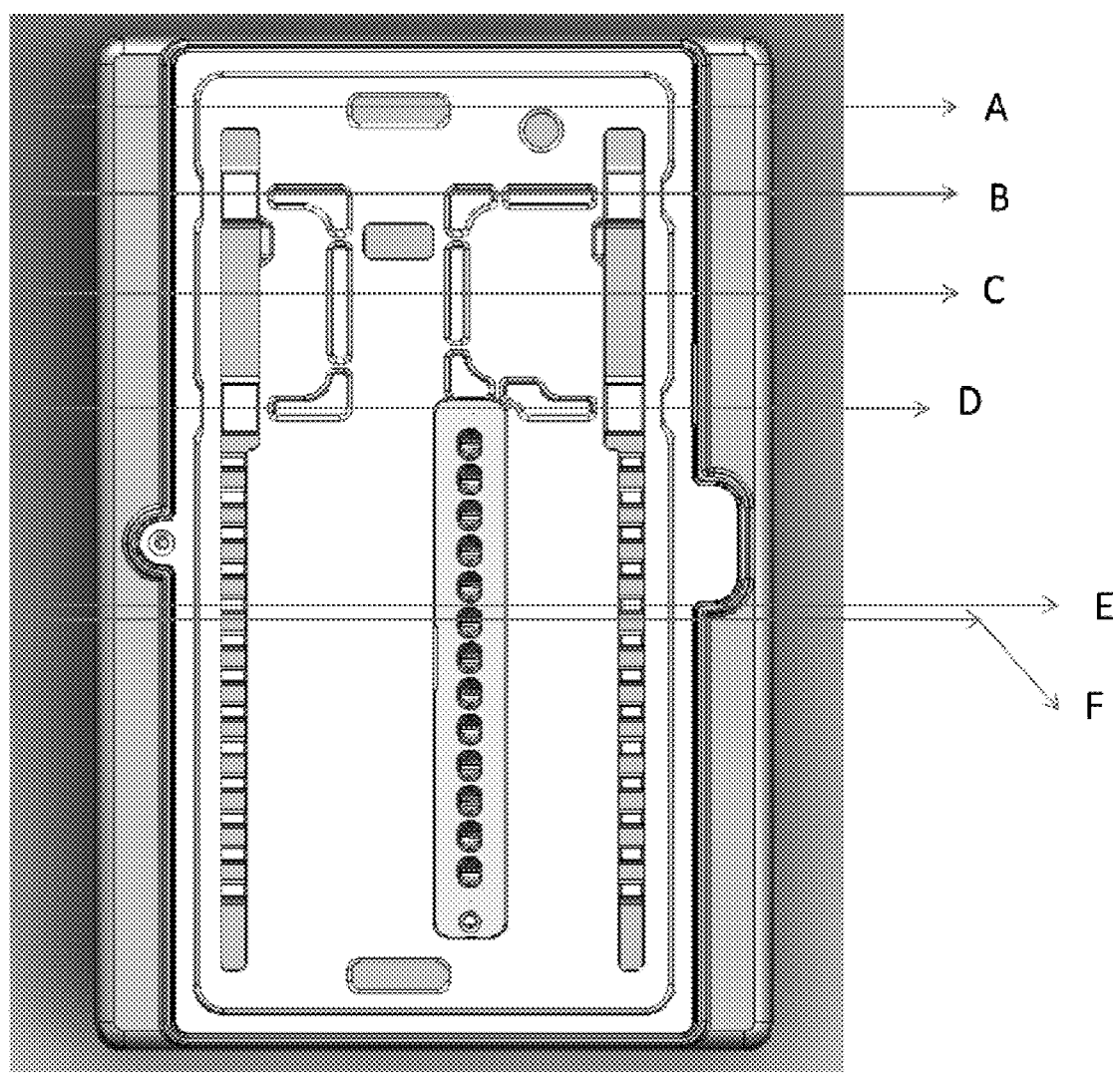
FIG. 39 is a schematic drawing depicting an alternative view of the cassette described in FIG. 34. Superimposed on this image are lines A, B, C, D, E, and F, each of which represents the position of a cross-sectional perspective provided in FIG. 40, panels A-F.
Figure 40A:
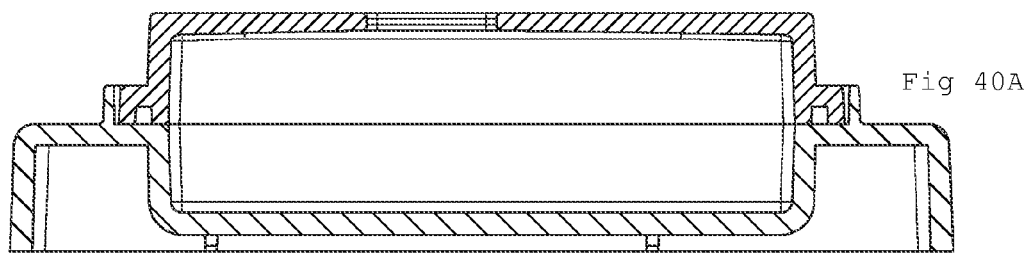
FIG. 40A is a schematic drawing depicting a cross-sectional view through the cassette described in FIG. 34 at the level of line A, as shown in FIG. 39.
Figure 40B:
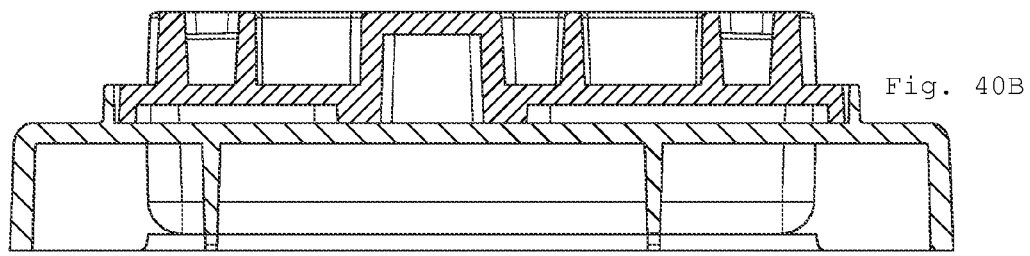
FIG. 40B is a schematic drawing depicting a cross-sectional view through the cassette described in FIG. 34 at the level of line B, as shown in FIG. 39.
Figure 40C:
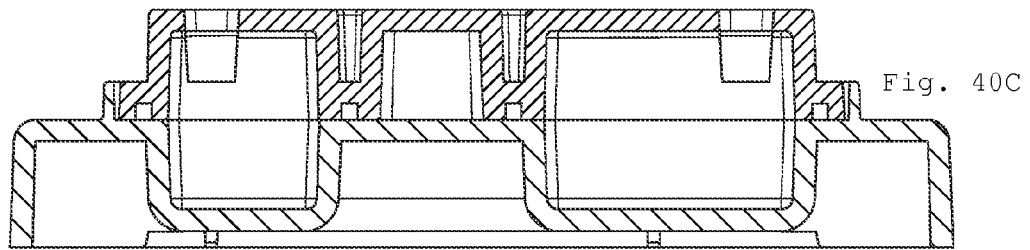
FIG. 40C is a schematic drawing depicting a cross-sectional view through the cassette described in FIG. 34 at the level of line C, as shown in FIG. 39.
Figure 40D:
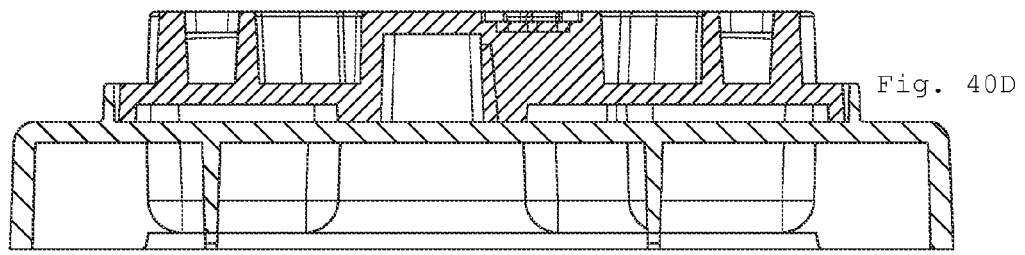
FIG. 40D is a schematic drawing depicting a cross-sectional view through the cassette described in FIG. 34 at the level of line D, as shown in FIG. 39.
Figure 40E:
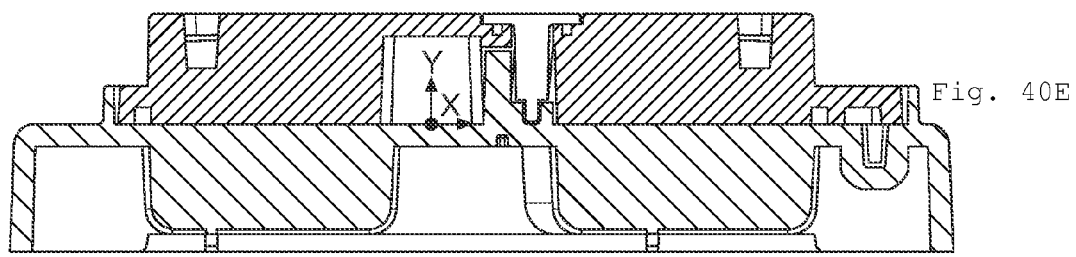
FIG. 40E is a schematic drawing depicting a cross-sectional view through the cassette described in FIG. 34 at the level of line E, as shown in FIG. 39.
Figure 40F:
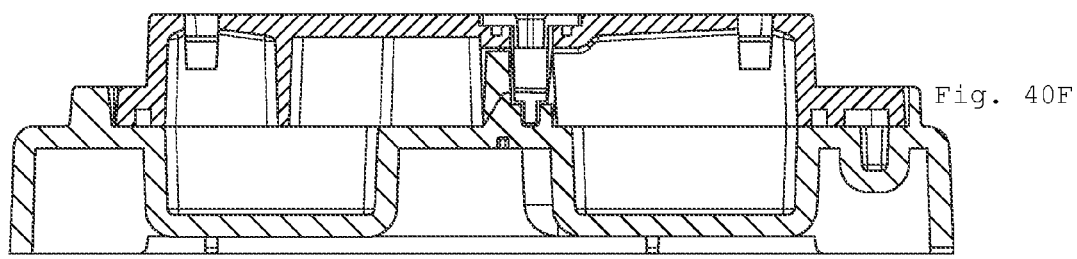
FIG. 40F is a schematic drawing depicting a cross-sectional view through the cassette described in FIG. 34 at the level of line F, as shown in FIG. 39.
Figure 42:
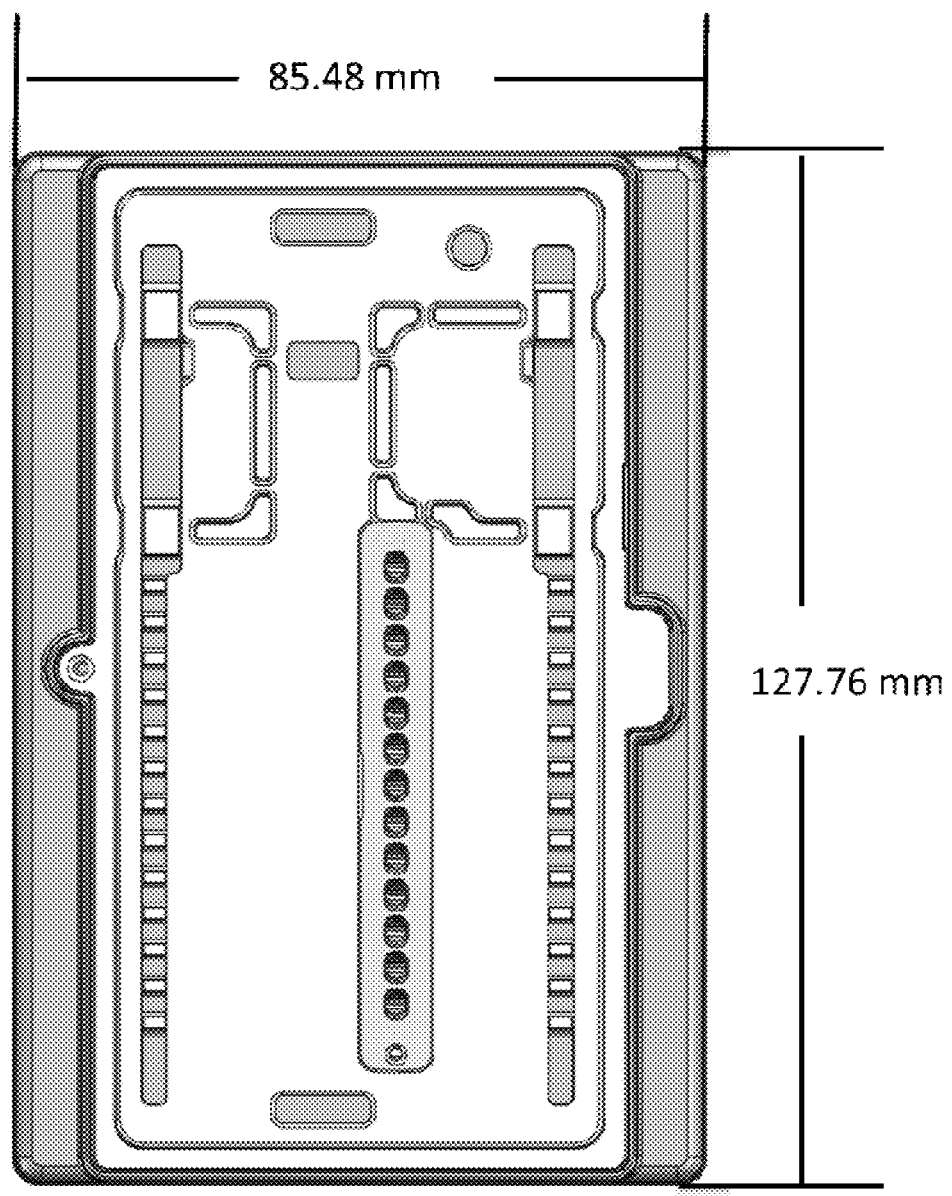
FIG. 42 is a schematic drawing depicting exemplary dimensions of the cassette described in FIG. 34. In certain embodiments, cassettes of the disclosure may have a width of 85.48 mm and a length of 127.76 mm.

When performing separation electrophoresis embodiments of cassettes of the disclosure as depicted in, for example, FIGS. 34-52, an electric field may be by separation electrodes inserted into electrode ports (504 and 507 as shown in FIG. 34) positioned at either end of the cassette. In certain aspects of these cassette embodiments, the separation electrodes may be post-electrodes (see, for example, FIGS. 47 and 48). In certain embodiments, elution electrodes of the cassettes, systems, and methods of the disclosure may not contact the cassette during separation electrophoresis (as shown in, for example, FIG. 48). Furthermore, in certain embodiments of the cassettes, systems, and methods of the disclosure, once separation electrophoresis has been completed, the separation electrodes are turned off, and, subsequently, elution electrodes are introduced into the elution electrode channels (510 and 511 as shown in FIG. 34, as well as in FIGS. 49 and 50). In certain embodiments of the cassettes, systems, and methods of the disclosure, once a pair of elution electrodes has been introduced into elution channels of the cassette, an electric field is applied to the elution electrodes, the strength of which is sufficient to drive separated sample molecules out of the gel matrix composition (e.g. agarose gel matrix composition) positioned in the at least one separation column and into at least one of an elution chamber positioned in, for example, an elution module strip (508 as shown in FIG. 34; 524 as shown in FIG. 37).

When an electric current is passed through a negatively-charged gel matrix (e.g. agarose gel matrix), an electroendoosmotic flow may be created that may transport fluid within the gel matrix or buffer compositions therein toward a negative electrode (e.g. separation or elution electrode). An electroendoosmotic flow may deplete the amount of a buffer composition contained within a reservoir in proximity to a positive electrode (e.g. separation or elution electrode). Sequentially or simultaneously, an electroendoosmotic flow may cause an overflow of buffer composition contained within a reservoir in proximity to a negative electrode (e.g. separation or elution electrode). When an electrophoresis process requires longer durations of time (e.g. when run times exceed an hour because, for example, high molecular weight DNA molecules are separated), an electroendoosmotic flow may exacerbate the depletion of buffer composition contained within a reservoir in proximity to a positive electrode and/or exacerbate an overflow of buffer composition contained within a reservoir in proximity to a negative electrode. Consequently, during long electrophoretic runs, either very large buffer reservoirs are used and/or the levels of buffer within those reservoirs are maintained by alternative means (including manually or mechanically adding and/or removing buffer from reservoirs, as needed).

In certain embodiments of the cassettes of the disclosure, the cassettes are designed to automatically regulate the amount of buffer contained in the reservoirs of the cassette. Particularly in the context of an electroendoosmotic flow, cassettes of the disclosure provides a solution to the long-felt need for a mechanism for maintaining substantially constant buffer levels within each reservoir of the cassette. As depicted, for example, in FIGS. 34-37, exemplary cassettes of the disclosure include electrode channels (510 and 511) that connect the outer edges of the upper and lower buffer reservoirs (514 and 519, respectively, as shown in FIGS. 36; 520 and 521, respectively, as shown in FIG. 37), extra buffer reservoirs (517 and 518, as shown in FIGS. 36; 530 and 531, as shown in FIG. 37) and the elution channels (515 and 516 respectively, as shown in FIGS. 36; 522 and 523 respectively, as shown in FIG. 37). As depicted, for example, in FIGS. 34-37, the electrode channels of exemplary cassettes of the disclosure connect each buffer reservoir of the cassette to every other buffer reservoir of the cassette. Consequently, the electrode channels of these cassettes prevent an overflow (i.e. accumulation) or depletion of buffer composition due to, for example, electroendoosmosis, because buffer accumulation and/or depletion may be dissipated by gravity-mediated flow through the elution electrode channels (510 and/or 511).

In certain embodiments of the cassettes of the disclosure, a pair of individual positive (+) and negative (−) electrodes may reside on opposite sides of each elution channel (see, for example, FIGS. 7, 17, and 18). When the cassette uses at least one pair of individual positive (+) and negative (−) electrodes positioned on opposite sides of at least one elution channel, the elution electrodes are unconnected or disconnected from one another during the separation step of the electrophoresis to avoid generating electrophoretic fields (that may be strong electrophoretic fields) extending away from the separation channel (and matrix composition therein) and into at least one of an elution channel. Electrophoretic fields generated during the separation electrophoresis and which extend away from the separation channel and into at least one of an elution channel may cause the sample analyte (e.g. DNA) to spread laterally into the elution channels. This lateral spread is premature because the methods of the disclosure recite a two-step electrophoresis method in which the sample is first separated along the direction of the separation channel and then eluted along the direction of the elution channels.

As depicted, for example, in FIGS. 34-37, exemplary cassettes of the disclosure include electrode channels (510 and 511) that simplify both form and function, when compared to the embodiments shown in, for example, FIGS. 7, 17, and 18. While both configurations result in fully-functional cassettes of the disclosure, the embodiments depicted in, for example, FIGS. 34-52, allow for simplification of the electrode form and function. Within these embodiments, separation electrodes are introduced into at least one of an upper and a lower buffer reservoir (514 and 519 respectively, as shown in FIGS. 36; 520 and 521 respectively, as shown in FIG. 37) through a port corresponding to each of the upper and lower buffer reservoirs (504 and 507 respectively as shown in FIG. 34), located at opposite ends of the cassette. In these cassettes, at least one elution electrode, comprised of, for example, an elongated form of conductive material (e.g. platinum wire) may be introduced into the cassette through at least one of the elution electrode channels (510 and 511, as shown in, for example, FIG. 34) (see also FIGS. 47-50). Because the elution electrode channels connect the each of the elution channels to every other elution channel, two elution electrodes (one positive and one negative) are sufficient to drive elution electrophoresis within each elution channel (e.g. within each of 13 elution channels, as depicted by the exemplary cassette shown in FIGS. 34-52). The design of the exemplary cassette shown in FIGS. 34-52 is simplified from the design shown in, for example, FIGS. 7, 17, and 18, because the number of elution electrodes has been reduced from 26 (as shown in these figures, one positive and one negative elution electrode for each of the 13 elution channels) to 2 (one positive and one negative elution electrode for the total number of elution channels (the new design may include any number of elution channels while requiring only one positive and one negative elution electrode)).

Figure 51A:
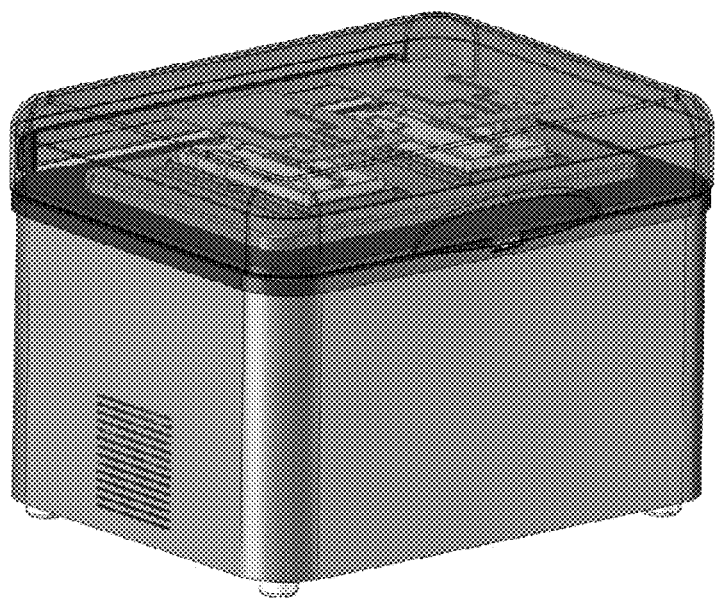
FIGS. 51A-B are schematic drawings depicting exemplary instruments of the disclosure having a lid to which one or more electrode boards or arrays are attached to the lid. Preferably the one or more electrode boards or arrays are attached to the lid in a rigid configuration that prevents or minimizes movement of the one or more electrode boards or arrays along or away from the lid. In certain embodiments of an instrument of the disclosure, the instrument contains one or more cassette nests to which a cassette of the disclosure may be operably linked or into which a cassette of the disclosure may be inserted. Following attachment of a cassette to a cassette nest of an exemplary instrument, and closure of the lid to which one or more electrode boards are attached, the surface/plate to which one or more cassette nests are attached may be raised, thereby causing the separation and/or elution electrodes of the one electrode boards to enter the cassette through at least one port on the outside surface of the top plate of the cassette. For example, a separation electrode may enter a port depicted as, for example, feature 504 or 507 of FIG. 34. Moreover, an elution electrode may enter an elution electrode channel depicted as, for example, feature 510 or 511 of FIG. 34. In certain embodiments, a separation electrode may extend further away from an electrode board than an elution electrode, and, therefore, a corresponding cassette may be raised to a first level to incorporate a separation electrode during separation electrophoresis and subsequently raised to a second and higher level to further incorporate an elution electrode during elution electrophoresis.
Figure 51B:
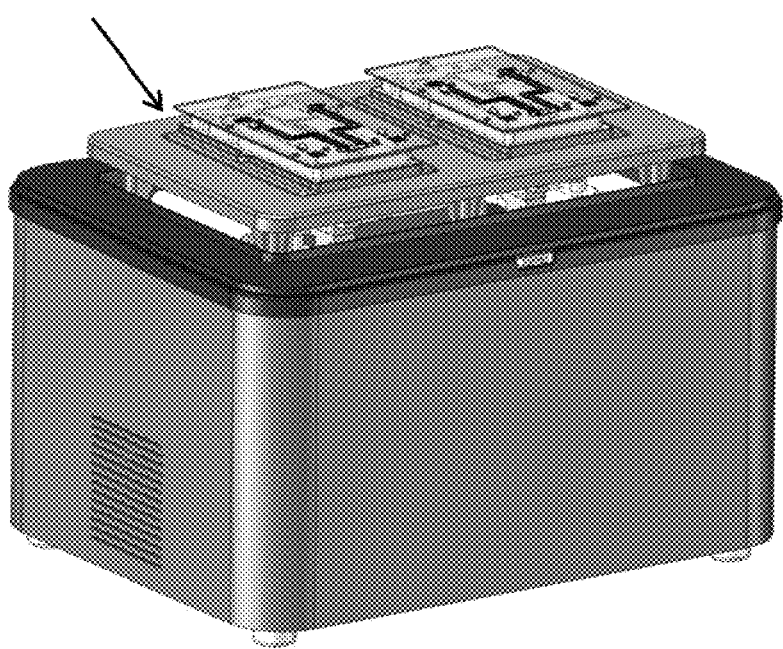
Figure 52A:
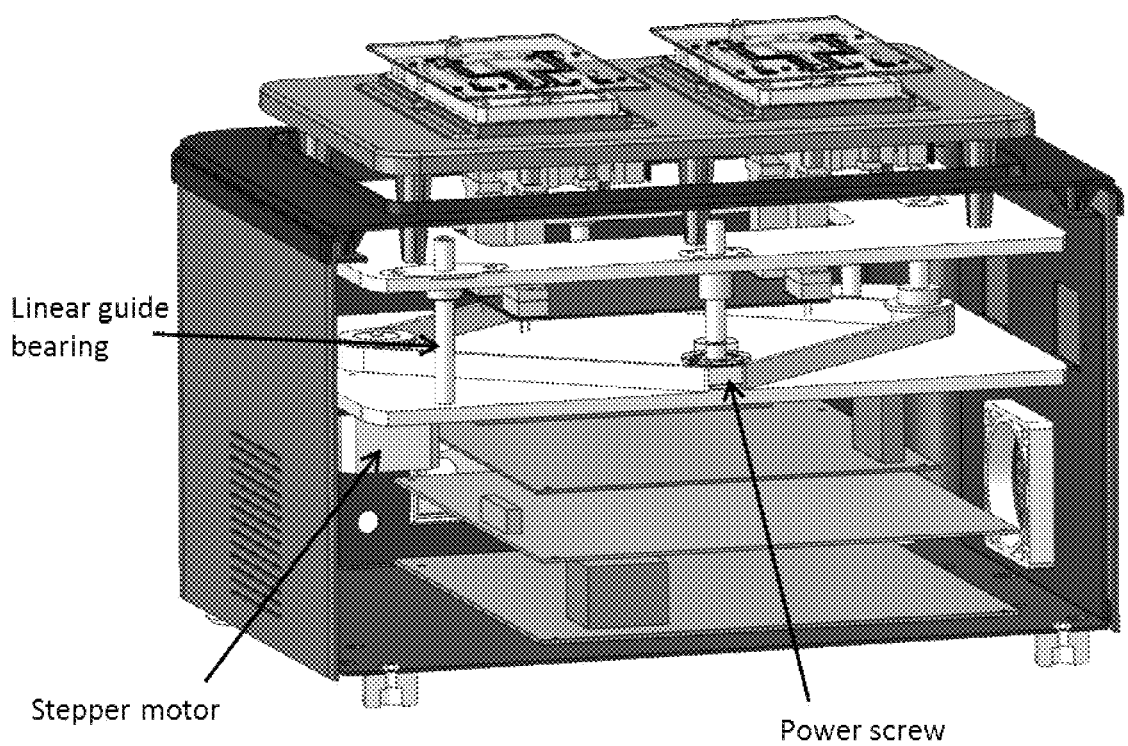
FIG. 52A is a schematic drawing depicting an exemplary instrument of the disclosure, and in particular detail, a nest elevator within the instrument. Exemplary nest elevators of the disclosure include a plate, platform or surface to which are operably-linked or attached at least one cassette nest. In certain embodiments, the nest elevator may be controlled by a stepper motor mounted to the interior of the instrument. In these embodiments, an exemplary motor of the instrument may drive one or more power screws (e.g. 3 power screws are shown) that translate the nest elevator plate, platform or surface up and down. The movement of a nest plate, platform or surface of the disclosure may be guided or constrained by a one or more linear guides (e.g. 2 linear guides are shown) to ensure proper tracking and z-axis alignment during insertion of a separation and/or elution electrode into a cassette of the disclosure.
Figure 52B:
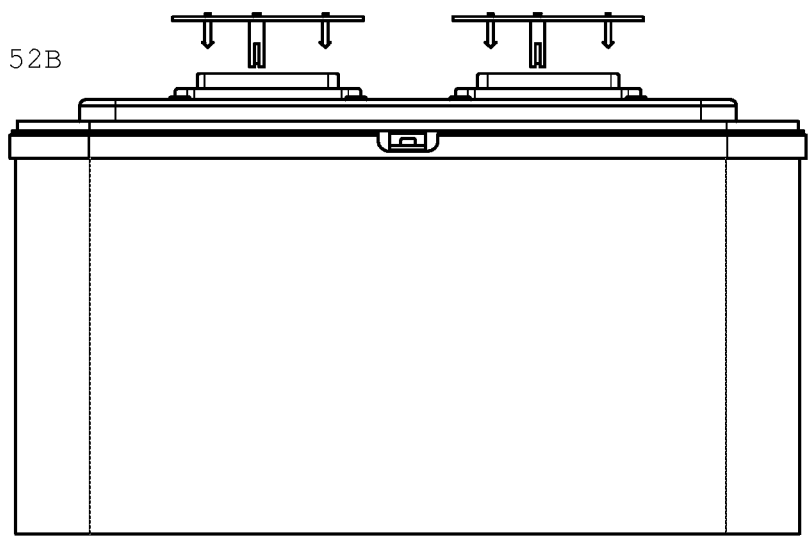
FIGS. 52B-D are schematic drawings depicting an exemplary instrument and nest elevator thereof of the disclosure, as shown in FIG. 52A. The top panel.
Figure 52C:
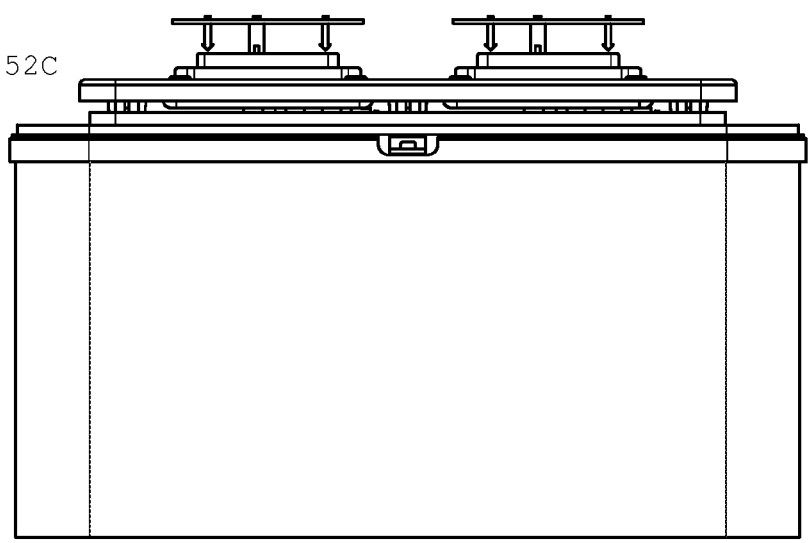
Figure 52D:
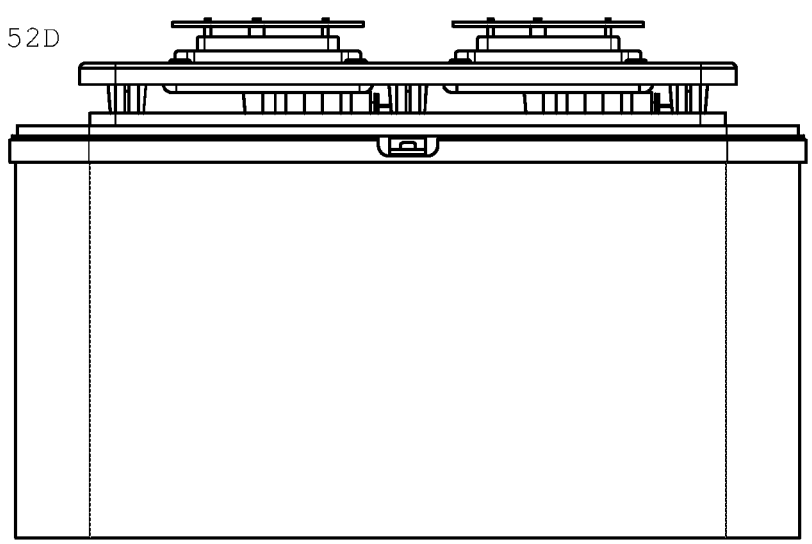

FIGS. 51 and 52 illustrate an embodiment of an exemplary instrument for use with the cassettes of the disclosure, as depicted in, for example, FIGS. 34-42. An instrument lid holds at least one of an electrode assembly. When the instrument power is turned off, the lid may be opened to a vertical position to allow access to at least one cassette nest positioned on the top side of the instrument base. In certain embodiments, the at least one cassette nest facilitates cassette and/or sample loading (and, furthermore, cassette and/or sample unloading). When the lid is closed, the electrode assemblies may be positioned directly over the cassettes in the instrument nests. In certain embodiments of this instrument, when the lid is closed, the electrode assemblies may be positioned directly over the cassettes in the instrument nests and maintained in this position by rigid restraints that prevent or minimize movement of the cassette. In certain embodiments, separation electrodes and elution electrodes may extend different distances from the lid. Upon activation of separation electrophoresis, the instrument cassette nest may be raised (for example, by manual, automatic, or mechanical means) until the separation electrodes contact the buffer in the upper and lower buffer reservoirs. Exemplary mechanical means for raising an cassette nest of an instrument of the disclosure include, but are not limited to, a servo motor mechanism. In certain embodiments of this instrument, the elution electrodes may not extend as far from the lid as the separation electrodes extend from the lid, and, furthermore, may not contact one or more of the elution electrode channels during separation electrophoresis. In accordance with these embodiments, after separation electrophoresis is completed, the cassette nest may be raised further until the elution electrodes contact buffer in the elution channels Upon completion of elution, the nest may lowered to its initial loading position, thereby disengaging the separation and elution electrodes from the cassette. Once the electrodes are disengaged from the cassette, the user may open the lid to access the cassette.

Gel separating matrices are typically prepared from agarose for nucleic acid separation and polyacrylamide for protein separation. In capillary electrophoresis, the matrices may be gels or solutions (e.g., linear polyacrylamide solution).

Gel separating matrices are typically made by pouring a liquid phase material into a mold formed by glass plates or separating matrix casting molds. In slab gel electrophoresis, for example, finger shaped outcroppings in plastic material form "combs" that are embedded in the top of the separating matrix. Sample loading wells are formed when the combs are removed from the solidified separating matrix. Loading these wells in a slab gel electrophoresis is typically a time consuming and technically challenging task. Dense solutions such as glycerol or polyethylene glycol are often added to samples prior to electrophoresis to prevent samples from mixing with electrode buffers and floating out of the wells.

Samples, generally in an aqueous buffer, are applied to the separating matrix and electrodes in electrical contact with the separation matrix are used to apply an electric field. The field induces charged materials, such as nucleic acids and proteins, to migrate toward either anode or cathode positions. Electrophoresis is usually completed in about 30 minutes to several hours.

The migration distances for the separated molecular species depend on their relative mobility through the separating matrix. Mobility of each species depends on hydrodynamic size and molecular charge. Proteins are often electrophoresed under conditions where each protein is complexed with a detergent or other material that imparts a negative charge to proteins in the sample. The detergent causes most or all of the proteins to migrate in the same direction (toward the electrophoresis anode). Samples are stained prior to, during, or after a separation run to visualize the nucleic acids or proteins within the gel. The location of the various components in the gel is determined using ultraviolet light absorbance, autoradiography, fluorescence, chemiluminescence, or any other well-known means of detection. To determine the molecular weight and relative concentration of unknown nucleic acids or proteins, the band positions and intensities are typically compared to known molecular standards.

Electrophoresis cassettes and systems of the disclosure separate, condense, detect, analyze, and collect desired fractions of analytes within a biological sample. As described in the figures provided, and defined in the description, cassettes and systems of the disclosure include distinctive features and corresponding functions.

Exemplary cassettes are molded from a plastic, such as polystyrene and its derivatives, or PMMA. Alternatively, the electrophoresis cassette is molded using any optically clear polymer. Electrophoresis cassettes are either molded as one contiguous piece, or they are assembled from multiple pieces, each molded from plastic or an appropriate optically clear plastic that are connected to form a contiguous piece.

Cassettes of the disclosure include macrofluidic channels, rather than microfluidic channels or nanochannels, to direct and fraction samples. The use of macrofluidic channels is essential to ensure that a sufficient amount of an analyte or sample is prepared or analyzed within a single application of the sample to the cassette such that the collected fraction can be used directly for further manipulation and analysis. For example, an isolated analyte or fraction is subsequently sequenced or inserted into a vector or cell.

Macrofluidic channels of the disclosure have a minimal demonstrated width of one micron (µm) or greater. In certain embodiments the depth of a macrofluidic channel of the cassette is uniform. However, dimensions and volumes of a macrofluidic channel of the cassette vary within preferred ranges. The preferred width of a macrofluidic channel ranges from between 1 µm and 100 mm and the preferred depth of a macrofluidic channel ranges from between 1 µm and 100 mm.

Macrofluidic channels include cavities and reservoirs. The term "cavity" is used to describe a portion of the channel that is reserved for either the attachment of a structure, the insertion of a structure within its volume, of the generation of a structure. A structure is formed, for instance by the placement of the sample well insert into the sample well cavity, the injection and solidification of a gel matrix composition, and the removal of the sample well insert. The term "reservoir" is meant to describe a cavity that is filled with a buffer composition.

Exemplary elution modules may include at least one of an analyte-permeable barrier and an analyte-impermeable barrier. The term "analyte-permeable" is meant to describe any barrier that is permeable to ions, polynucleic acids, and polypeptides, but not to, any other component of the gel matrix composition or buffer composition. The term "analyte-impermeable" is meant to describe any barrier that is permeable to ions, but impermeable to polynucleic acids, polypeptides, any other component of the gel matrix composition, buffer composition, or elution composition. In certain embodiments of an elution module, the module includes an analyte-permeable barrier (e.g. membrane) on a side proximal to a separation channel. Alternatively, or in addition, the module includes an analyte-impermeable barrier (e.g. membrane) on a side distal to a separation channel. In certain embodiments of an elution module, the module includes an analyte-permeable barrier (e.g. membrane) on a side proximal to a separation channel and an analyte-impermeable barrier (e.g. membrane) on a side distal to a separation channel.

Exemplary elution modules may be generated, at least in part, by contacting two membrane-carrier strips at one side to form a V-shaped configuration. This V-shaped membrane carrier may be attached or integral to the plate of either a single unit or multiunit plate. For example, in a multiunit plate, the V-shaped membrane carrier may be attached or integral to a base or central unit. A compressible strip may be attached to either a V-shaped membrane carrier or to an elution module divider strip. An elution module divider strip, corresponding to the size, position, and geometry of a membrane carrier (for example, both may be V-shaped), may be attached or integral to a central or cover unit. At least one of an analyte permeable membrane and an analyte impermeable membrane are contacted to either a compressible strip or an elution module divider strip. When an elution module divider strip is compressed against a membrane holder, individual elution modules having at least one of an analyte permeable membrane and an analyte impermeable membrane are generated. Preferably, the resultant individual elution modules include an analyte permeable membrane and an analyte impermeable membrane. In a preferred configuration, an individual elution module includes an analyte permeable membrane on the side surface in closer proximity to a separation channel and an analyte impermeable membrane on a side surface opposite the side containing the analyte permeable membrane.

One of the superior properties of an electrophoresis cassette of the disclosure is the collection of an analyte, or fraction thereof, in an elution buffer composition. Other preparative electrophoresis systems require the user to extract, for example, a DNA fraction, from a gel or membrane following electrophoresis. This secondary DNA extraction step is time-consuming and significantly decreases the overall yield of DNA obtained from that fraction. In contrast, electrophoresis cassettes and systems of the disclosure integrate the steps of polynucleotide or polypeptide separation and collection by providing an elution module, which simultaneously fractions and extracts the polynucleotide or polypeptide analyte into any desired elution buffer.

Macrofluidic channels contain at least one of a gel matrix composition, a liquid buffer composition, or a solid buffer composition. Gel matrix compositions contain a polymerizing compound, such as agarose or polyacrylamide, for the separation of polynucleic acids and polypeptides, respectively. Polymerizing compounds are provided at percentages ranging from 0.01%-99.9%. Electrophoresis buffer compositions known in art are used herein. Buffer solutions are preferably electrolyte solutions.

Electrophoresis cassettes optionally contain electrodes that are either disposable or reusable. Disposable electrodes may be integrated into the cassettes. Electrodes may be made from epoxy with conductive particles, inks, or rubber. Electrodes may be made of titanium or platinum as well as coated titanium or platinum. Electrodes may be made of graphite or elongated graphite forms (e.g. graphite rods). Electrodes may take one or more forms including, but not limited to, strips or elongated forms of conductive material (such as platinum) (see FIGS. 34-52). Alternatively, electrodes may be comprised of conductive inks. Exemplary conductive inks can be printed onto the disposable cassettes or a component thereof. Conductive inks may be printed onto membranes, screens, plastics, or polymers. For example, a suitable conductive ink includes the screen-printable, electrically conductive ink available from Creative Materials (Part# 122-49; additional information publicly available at server.creativematerials.com/datasheets/DS_122_49.pdf).

Electrodes of the cassette may either be separation electrodes or elution electrodes. Separation electrodes are connected or activated (i.e., provided with sufficient power to turn on) during the at least one separation step. Optionally, these electrodes are disconnected or inactive during the at least one elution step. Separation electrodes are positioned either within or adjacent to a first buffer reservoir or a second buffer reservoir of a cassette. In certain embodiments of the disclosure, a negative separation electrode is positioned within or adjacent to a first buffer reservoir of the cassette. Alternatively, or in addition, a positive separation electrode is positioned within or adjacent to a second buffer reservoir of the cassette. Elution electrodes are connected or activated only during the at least one elution step. Elution electrodes are disconnected or inactivated during the at least one separation step.

With respect to elution electrodes of the cassettes, elution electrodes may be point or pin electrodes. Alternatively, or in addition, elution electrodes may be elongated forms, strips, or wires composed of electroconductive material (see, for example, FIGS. 34-52). In certain embodiments, elution electrodes may include platinum wires that may be introduced into at least one of an elution electrode channel Elution electrodes may be positioned within at least one negative elution reservoir or channel and at least one positive elution reservoir or channel. In certain embodiments of the disclosure, a negative elution electrode is positioned within or adjacent to a negative elution reservoir or channel. Alternatively, or in addition, a positive elution electrode is positioned within or adjacent to a positive elution reservoir or channel. Preferably, a negative elution electrode is positioned within or adjacent to a negative elution reservoir or channel and a positive elution electrode is positioned within or adjacent to a positive elution reservoir or channel. Negative and positive elution reservoirs or channels may be aligned with one another, yet located on opposite sides of a separation channel. For example, each negative elution reservoir or channel may align with each positive elution channel or channel along an axis perpendicular to a separation channel (see, for example, FIG. 7). Alternatively, or in addition, each negative elution reservoir or channel may align with each positive elution channel or channel along an axis parallel to a separation channel (see, for example, FIGS. 36 and 37).

Exemplary cassettes, instruments, systems, and methods of the disclosure may use field inversion gel electrophoresis (as referred to as FIGE). Field inversion gel electrophoresis is a pulsed field gel electrophoresis technique that is based upon the periodic inversion of a uniform electric field. Using field inversion gel electrophoresis, analyte migration occurs in a "forward" direction because the duration and amplitude of the "forward" pulse is, on average, larger than the duration and amplitude of the pulse in the reverse direction, or "backward" pulse. As applied to the cassettes, instruments, systems, and methods of the disclosure, the forward direction may be defined in the context of nucleic acid samples as movement away from a negative charge and/or movement towards a positive charge. As used to describe "positive" and "negative" electrodes of the cassettes, instruments, systems, and methods of the disclosure, the term "positive" describes an average net positive charge over any particular duration of time. Conversely, as used to describe "positive" and "negative" electrodes of the cassettes, instruments, systems, and methods of the disclosure, the term "negative" describes an average net negative charge over any particular duration of time.

Sample wells may have multiple geometries. The geometry of the sample well reflects the geometry of the sample well insert used to define the negative space not occupied by the gel matrix composition. Preferably, the sample wells of the disclosure have the have a unique "chimney" shape. Generally, sample well insert, or sample comb has a simple rectangular shape, which forms a simple rectangular negative space within the gel. As such, in such a gel, the top of the sample well is level with the top of the gel and, if a cover were applied, the top of the well would be flush or level with the bottom of the cover. However, under certain circumstances this sample well geometry, particularly when a cover is attached to the electrophoresis cassette base, allows for leakage of the sample in the liquid-filled space between the top of the gel and the cover plate. This leakage leads to contamination of the desired fractions within the elution chamber.

The chimney geometry was developed in conjunction with an adaptation of the cover, i.e. the sample well port, to support the gel chimney and prevent leakage of the sample, and, therefore, contamination of desired fractions within the elution chamber. The sample well port of the cover is adapted to support the gel chimneys of the sample well.

The chimney well of a cassette of the disclosure provides superior electrophoresis because the purpose of preparative electrophoresis is the precise and exact separation of fractions from a sample that differs in a physical property. In certain circumstances, the differences between collected and discarded fractions are very subtle. Contamination of the collected fractions with random analyte from the sample pulled into the seam by capillary action between the gel and the bottom of the cover plate significantly distorts the results. Thus, chimney wells provide a superior and distinguishing feature of the disclosure.

Electrophoresis cassettes and systems of the disclosure fractionate, analyze, and collect polynucleic acid and polypeptide analytes or fractions within a sample.

The term "sample" describes a plurality of molecules that can be separated using gel electrophoresis. The term "fraction" describes a subset of the plurality of molecules within a sample. A fraction is defined or determined by size. Alternatively, a fraction is defined or determined by any physical property that causes it to migrate at a faster or slower rate than other components or fractions of a sample when driven to migrate through a buffer composition of the disclosure by the force of an electric field (i.e., electrophoretic mobility).

An exemplary sample includes, but is not limited to, a nucleic acid, an oligonucleotide, a DNA molecule, a RNA molecule, or any combination thereof. Alternatively, or in addition, a sample includes, but is not limited to, an amino acid, a peptide, a protein, or any combination thereof. For example, a sample is a whole cell lysate, or the DNA or protein fraction of a cell lysate.

Nucleic acids are derived from genomic DNA, double-stranded DNA (dsDNA), single-stranded DNA (ssDNA), coding DNA (or cDNA), messenger RNA (mRNA), short interfering RNA (siRNA), short-hairpin RNA (shRNA), microRNA (miRNA), single-stranded RNA, double-stranded RNA (dsRNA), a morpholino, RNA interference (RNAi) molecule, mitochondrial nucleic acid, chloroplast nucleic acid, viral DNA, viral RNA, and other organelles with separate genetic material. Furthermore, samples include nucleic acid analogs that contain modified, synthetic, or non-naturally occurring nucleotides or structural elements or other alternative/modified nucleic acid chemistries known in the art. Additional examples of nucleic acid modifications include the use of base analogs such as inosine, intercalators (U.S. Pat. No. 4,835,263) and minor groove binders (U.S. Pat. No. 5,801,115). Other examples of nucleic acid analogs and alternative/modified nucleic acid chemistries known in the art are described in Current Protocols in Nucleic Acid Chemistry, John Wiley & Sons, N.Y. (2002).

PNA oligomers are included in exemplary samples or fractions of the disclosure. PNA oligomers are analogs of DNA in which the phosphate backbone is replaced with a peptide-like backbone (Lagriffoul et al., Bioorganic & Medicinal Chemistry Letters, 4: 1081-1082 (1994), Petersen et al., Bioorganic & Medicinal Chemistry Letters, 6: 793-796 (1996), Kumar et al., Organic Letters 3(9): 1269-1272 (2001), WO96/04000).

Polypeptides or proteins are complex, three-dimensional structures containing one or more long, folded polypeptide chains. Polypeptide chains are composed of a plurality of small chemical units called amino acids. Naturally occurring amino acids have an L-configuration. Synthetic peptides can be prepared employing conventional synthetic methods, using L-amino acids, D-amino acids or various combinations of L- and D-amino acids. The term "peptide" describes a combination two or more amino acids. Naturally occurring amino acids have an L-configuration. Peptides having fewer than ten amino acids are "oligopeptides," whereas peptides containing a greater number of amino acid units are "polypeptides." Any reference to a "polypeptide" also includes an oligopeptide. Further, any reference to a "peptide" includes polypeptides and oligopeptides. Each different arrangement of amino acids forms a different polypeptide chain.

The term "nucleic acid molecule" describes the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. The term nucleic acid molecule, and in particular DNA or RNA molecule, refers only to the primary and secondary structure of the molecule, and does not limit it to any particular tertiary forms. Thus, this term includes double-stranded DNA found, in linear or circular DNA molecules (e.g., restriction fragments), plasmids, and chromosomes. A "recombinant DNA molecule" is a DNA molecule that has undergone a molecular biological manipulation. (Sambrook et al. Molecular Cloning, A Laboratory Manual, Cold Spring Harbor Laboratory Press).

Optionally, samples are combined with a reagent that imparts a net negative charge, denatures a peptide or protein, or digests a DNA or RNA molecule prior to application to an electrophoresis system. These reagents are known in the art. Furthermore, samples are combined with agents that impart fluorescent, magnetic, or radioactive properties to the sample or fractions thereof for the purpose of detection. In one embodiment of the system, a dsDNA sample is mixed with ethidium bromide, applied to the electrophoresis cassette, and fractions of the sample are detected using an ultrabright green LED.

All standard and specialty buffers known in the art are used with samples, and fractions thereof, as well as to make the buffer compositions the fill the electrophoresis cassettes of the disclosure.

Regarding polypeptides, the term "native" is meant to describe a non-denatured polypeptide. Polypeptide analytes of the disclosure are native or denatured.

Electrophoresis systems of the disclosure are compact and automated. These systems are designed and intended for desktop or bench-top use. Furthermore, electrophoresis cassettes of these systems are disposable.

Systems include at least one electrophoresis cassette with means to fractionate, detect, analyze, and collect a polynucleic acid or polypeptide analyte or fraction within a sample.

Systems include an illumination source that may be independent of the system or integral to the system. For example, the illumination source uses ultra-bright light emitting diode (LED) in combination with a filter set and one or more photodiodes.

Systems include a detection module with means to detect a signal from the sample, or analyte or fraction thereof. Exemplary signals include, but are not limited to, visible light, fluorescent light, magnetic fields, and radioactivity. Detection modules are positioned at a detection zone of a separation channel of an electrophoresis cassette.

The detection module of an electrophoresis system of the disclosure, which optionally includes an illumination source, is coupled to a microprocessor control system. The microprocessor control system includes a microprocessor, software, and a set of relays with means to control a voltage switching scheme that differentially activates at least one negative and at least one positive separation electrode during a separation step to move the sample, or analyte or fraction thereof through the separation channel. The voltage switching scheme also differentially activates at least one negative and at least one positive elution electrode during an elution step to move the sample, or analyte or fraction thereof along a direction orthogonal or perpendicular to the separation channel, therefore, moving the sample, or analyte or fraction thereof into an elution module of the cassette. When the system activates a separation electrode, the system deactivates or delays activation of all elution electrode of the cassette. When the system activates an elution electrode, the system may optionally deactivate one or more separation electrodes of the cassette.

An independent computer (e.g. a separate laptop, desktop, or bench top computer) may be substituted for the use of an incorporated microprocessor. Exemplary software for controlling the electrophoresis systems of the disclosure is developed for use with either an incorporated microprocessor or an independent computer.

Systems further include an integrated or separate power source.

In certain embodiments of the electrophoresis cassettes and systems of the disclosure, a separation channel of the cassette is positioned horizontally, or oriented in parallel, with respect to the surface (desktop or table) on which the system is located during use. Alternatively, the system is configured such that a separation channel of the cassette is positioned vertically, or oriented in perpendicular, with respect to the surface (desktop or table) on which the system is located during use.

EXAMPLES

Example 1

Simultaneous Size Fractionation of a Complex Protein Sample by Preparative Electrophoresis Protein Sample contained 45 µL of Mouse Brain Lysate (1 µg/µl protein in SDS-PAGE loading buffer, Rockland Catalog # W10-000-T004). The protein sample was mixed with 5 µL of loading solution (loading solution is 7.5% w/v Ficoll 400, 0.5% SDS, 12 mM DTT, 0.45×KBB buffer (1×KBB buffer is 102 mM Tris base, 57.6 mM TAPS acid, 0.96 mM EDTA acid, pH 8.7)), and heated to 85° C. for 5 minutes prior to loading. An electrophoresis tracking dye, bromophenol blue, was included in the lysate formulation provided by the supplier.

A gel matrix composition was prepared with 3% low melting agarose (Metaphor agarose, Lonza# 50184) in 0.5× KBB buffer. The molten 3% agarose mixture was equilibrated to 60° C. before gel casting. The elution module strip was prepared with an analyte-permeable barrier (a hydrophilic PVDF sterile filter membrane (Durapore, 0.45 μm pore size, EMD-Millipore)) on the side of the elution modules proximal to the separation channel and an analyte-impermeable barrier (a PES ultrafiltration membrane (Biomax, 10,000 kD cutoff, Millipore)) on the side of the elution modules distal to the separation channel (e.g., the opposite side of the elution module). Both membranes were heat-staked onto the elution module strip. An insert was positioned within each of the negative and positive elution reservoirs (FIG. 9) to prevent the molten agarose from entering these spaces during gel casting. The analyte-permeable membrane on the side of the elution module strip proximal to the separation channel prevents agarose from flowing into any of the elution modules.

Figure 1:
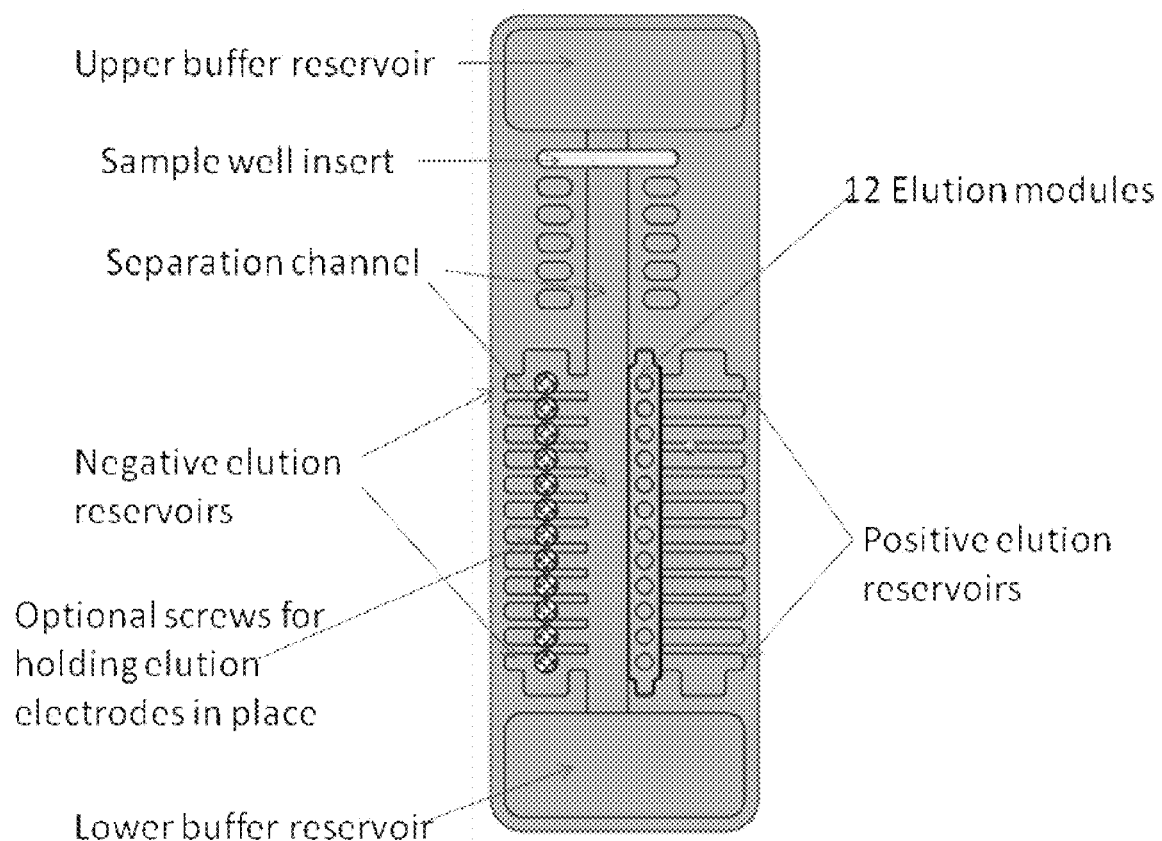
FIG. 1 is a schematic diagram depicting an exemplary cassette. As shown, this cassette includes, from top to bottom, at least one of a first buffer reservoir (labeled "upper buffer reservoir" for the purposes of the illustration), a separation channel in fluid and electrical communication with the first buffer reservoir, a "negative" elution reservoir corresponding to a "positive" elution reservoir (oriented, for example, in parallel), and a second buffer reservoir (labeled "lower buffer reservoir" for the purposes of the illustration). In certain embodiments of the cassette, the cassette further includes, at least one of a sample well cavity and an elution module cavity. In certain embodiments of the cassette, the cassette further includes, at least one of a sample well insert that may occupy a volume of a sample well cavity. In certain embodiments of the cassette, the cassette further includes, at least one of an elution module that may occupy a volume of an elution module cavity. A cassette of the disclosure includes at least negative elution reservoir and at least one positive elution reservoir. As shown in this figure, an exemplary cassette of the disclosure may include 12 negative elution reservoirs and 12 positive elution reservoirs. As shown, a cassette of the disclosure may include at least one elution module per positive elution reservoir, and, therefore, in embodiments including 12 positive elution reservoirs, the cassette may include 12 elution modules. In certain embodiments, two or more elution modules may be arranged in a strip, in which each module is connected to any adjacent module(s). In certain embodiments of a cassette of the disclosure, a cassette further includes at least one screw for holding at least one elution electrode in position (as shown in this figure). Moreover, the number of optional screws provided may equal the number of elution electrodes provided.
Figure 2:
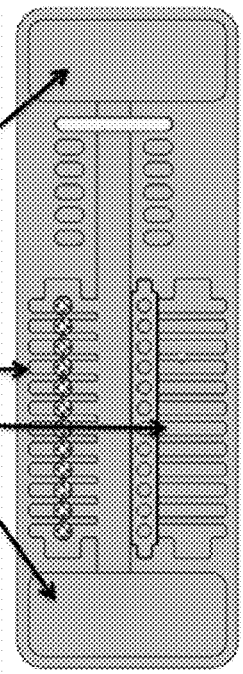
FIG. 2 is a schematic diagram and corresponding table depicting exemplary reservoir volumes of a cassette of the disclosure. As shown in this figure, representing an embodiment of a cassette of the disclosure, the volume of a first or upper buffer reservoir may be about 12,360 µL. As shown in this figure, representing an embodiment of a cassette of the disclosure, the volume of a second or lower buffer reservoir may be about 12,360 µL. As shown in this figure, representing an embodiment of a cassette of the disclosure, the volume of a negative elution reservoir may be about 289 µL. As shown in this figure, representing an embodiment of a cassette of the disclosure, the volume of a positive elution reservoir may be about 289 µL.
Figure 4:
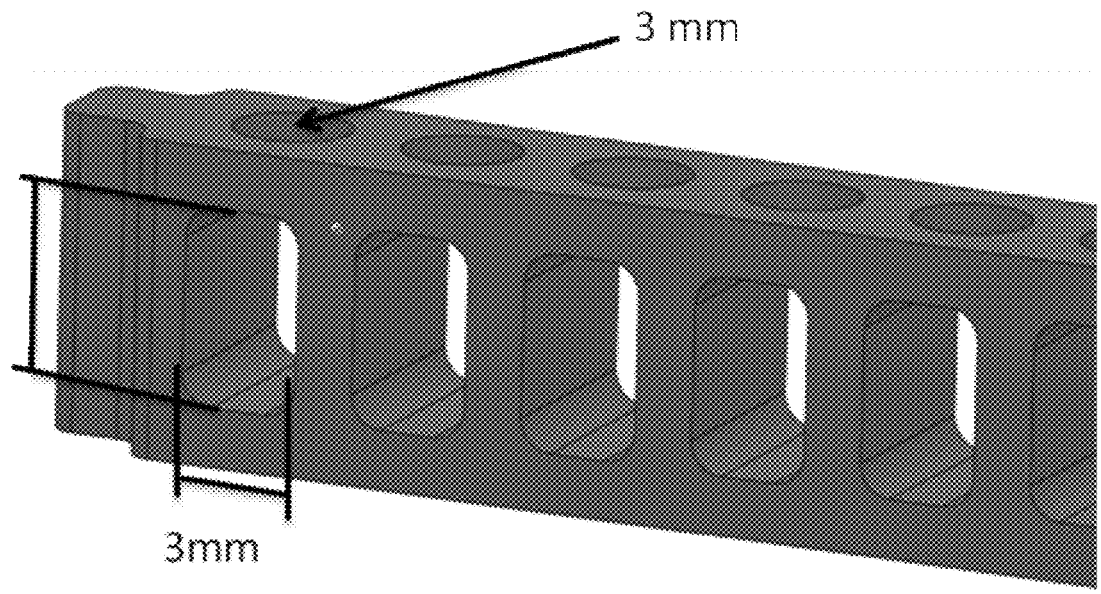
FIG. 4 is a schematic diagram depicting exemplary elution chamber dimensions of a cassette of the disclosure. As shown in this figure, representing an embodiment of a cassette of the disclosure, a height of an elution chamber may be about 5 mm. As shown in this figure, representing an embodiment of a cassette of the disclosure, a width of an elution chamber may be about 3 mm. As shown in this figure, representing an embodiment of a cassette of the disclosure, a cross-sectional area of an elution chamber may be about 15 $mm^2$. As shown in this figure, representing an embodiment of a cassette of the disclosure, an elution chamber may include a port to facilitate the injection and removal of buffer compositions and collected samples, analytes, or fractions. An exemplary port of an elution chamber may have a diameter of about 3 mm. As shown in this figure, representing an embodiment of a cassette of the disclosure, a volume or a total volume of an elution chamber may be about 92.20 µL (this volume includes the volume of a port). The exemplary elution chambers shown in this figure are arranged in a strip, however, alternatively, individual elution chambers may be provided in a separated configuration.
Figure 5A:
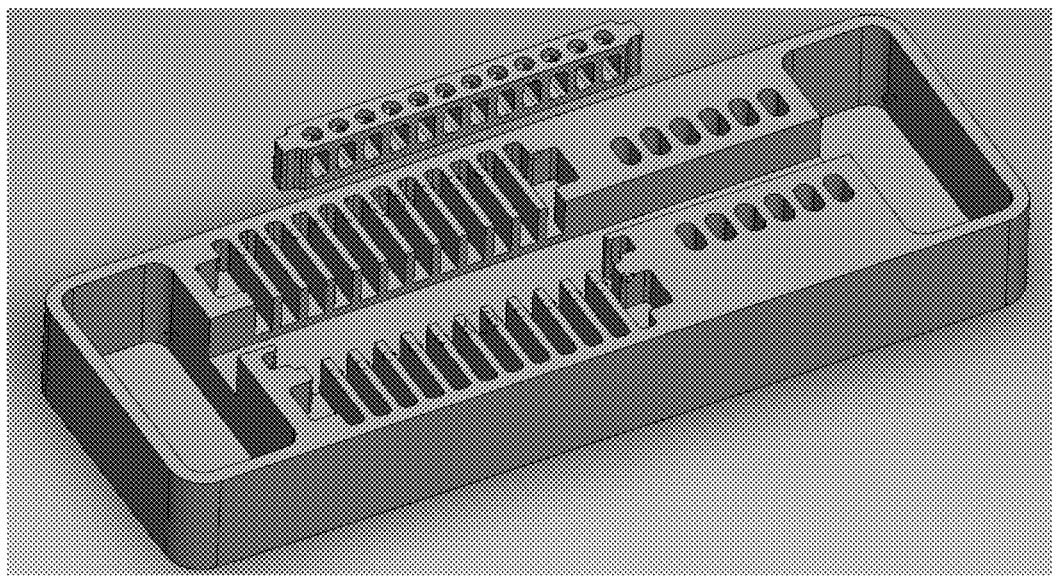
FIG. 5A is a schematic diagram depicting an embodiment of a cassette of the disclosure in which a strip of elution chambers is inserted into a cassette. In this view the strip of elution chambers is separate, but aligned with the cassette. In certain embodiments of the cassette, the cassette includes an elution module cavity into which one or more elution modules are inserted.
Figure 5B:
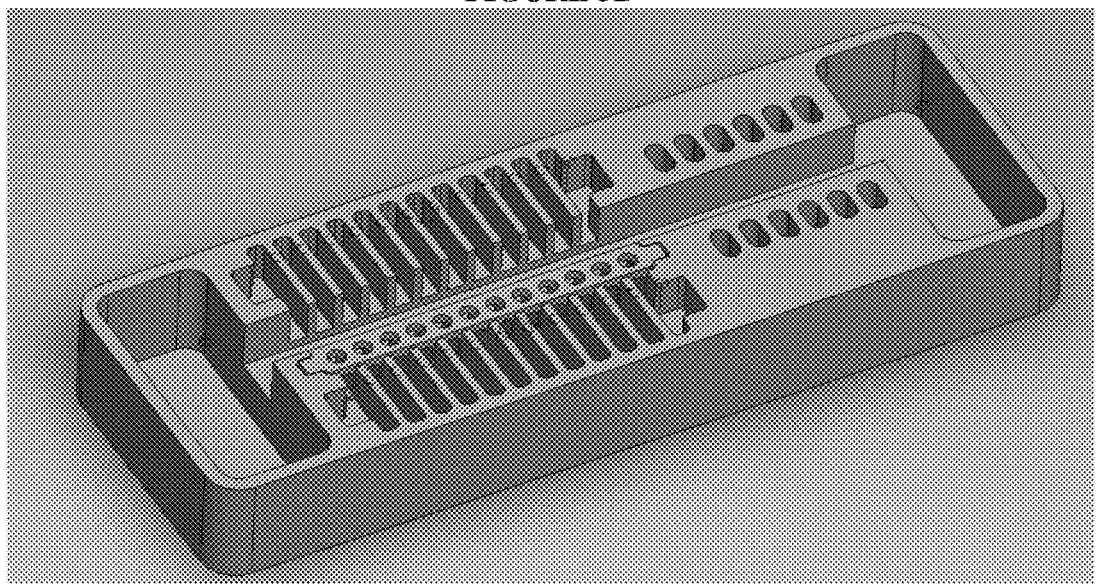
FIG. 5B is a schematic diagram depicting an embodiment of a cassette of the disclosure in which a strip of elution chambers is inserted into a cassette. In this view the strip of elution chambers is inserted into the cassette. In certain embodiments of the cassette, one or more elution modules are inserted into a cassette. Alternatively, or in addition, one or more elution modules may be inserted into one or more elution module cavities of a cassette.
Figure 6:
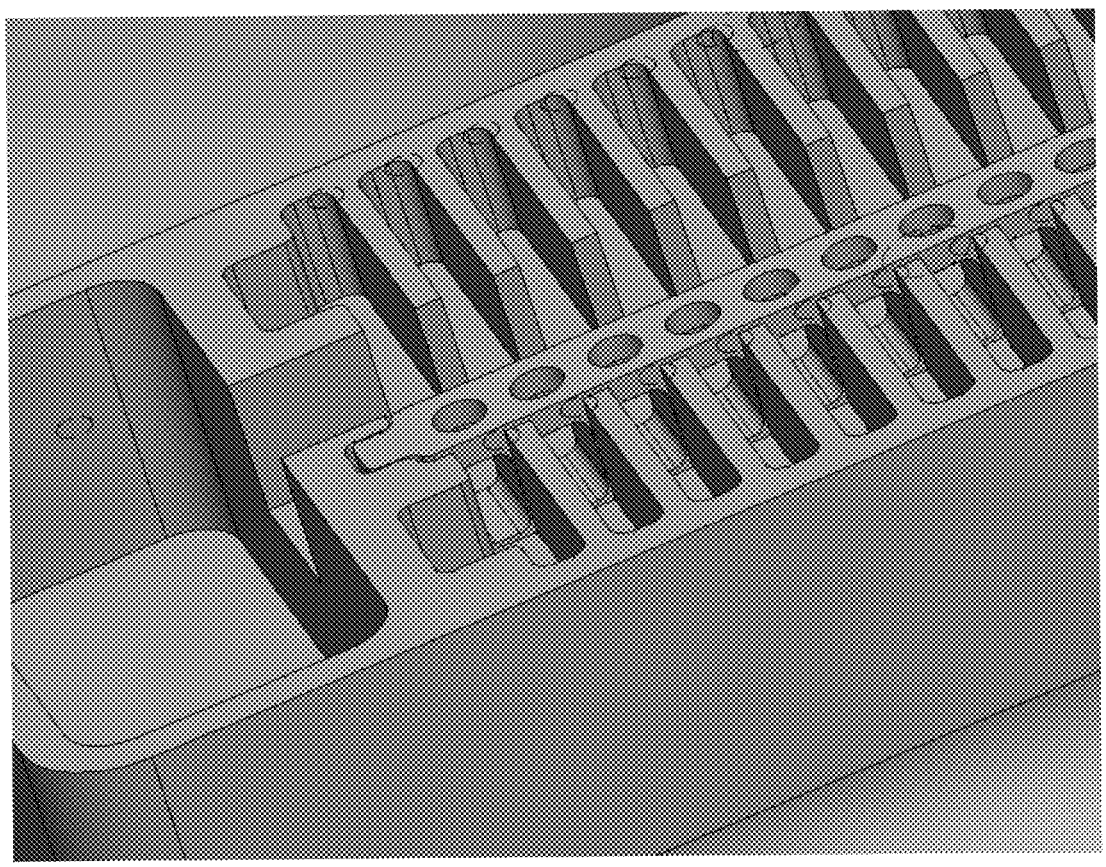
FIG. 6 is a schematic diagram depicting an embodiment of a cassette of the disclosure in which a strip of elution chambers is inserted into a cassette. From this perspective, the alignment of a strip of elution modules with one or more elution reservoirs
Figure 9:
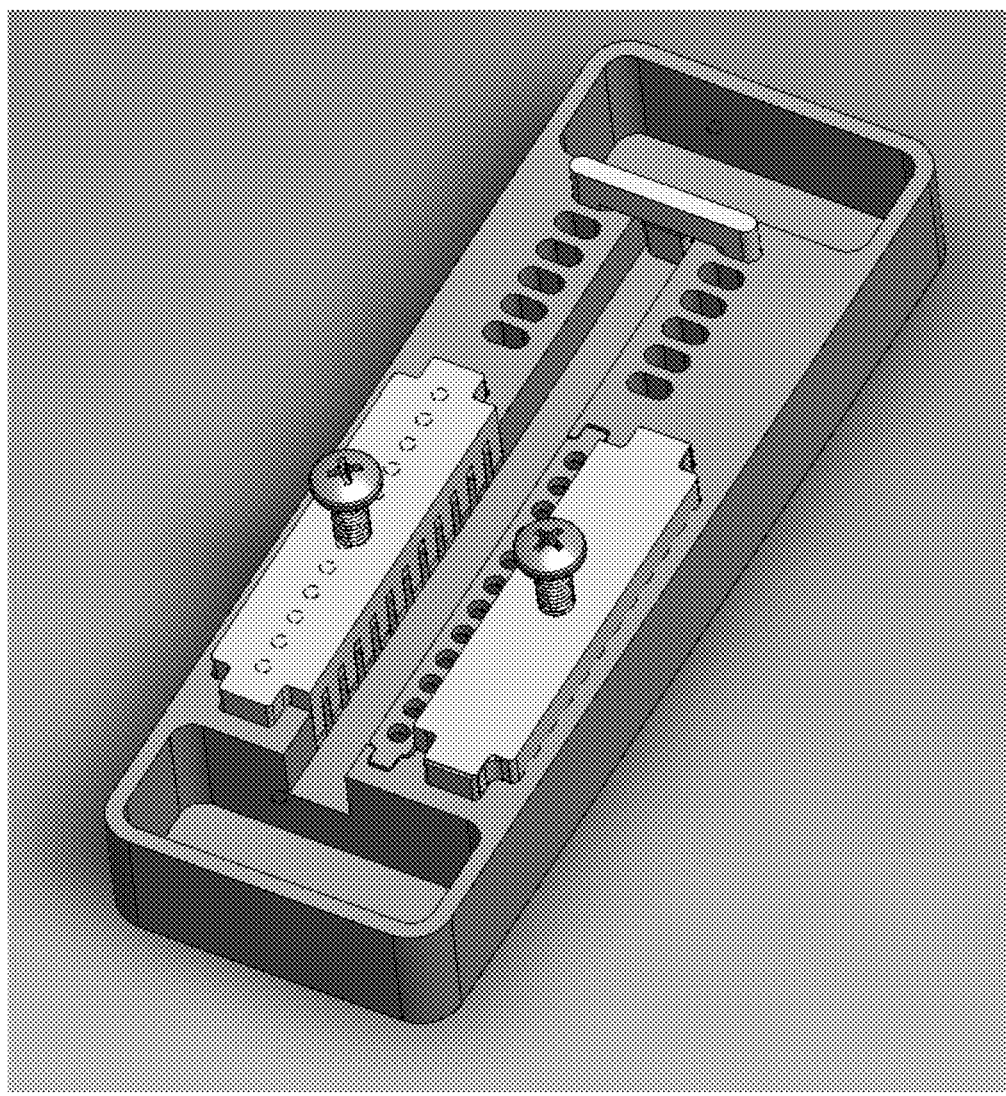
FIG. 9 is a schematic diagram depicting an assembled view an exemplary cassette in which a sample well insert occupies a volume of a separation channel, a negative elution reservoir insert occupies a volume of at least one negative elution reservoir, a positive elution reservoir insert occupies a volume of at least one positive elution reservoir, a strip of elution modules occupy a volume of at least one positive elution reservoir, and optionally, a screw is used to hold the negative elution reservoir insert and the positive elution reservoir insert in position. The sample well insert may occupy a volume of a sample well cavity and/or a volume of separation channel. The strip of elution modules may occupy a volume of at least one elution chamber cavity and/or at least one positive elution reservoir. As shown in this figure, the exemplary cassette with the inserts positioned in the cassette, is ready for casting. A gel matrix composition including, for example, agarose or acrylamide, may be applied to the cassette in a liquid formulation. Upon polymerization to a solid, the gel matrix composition fills a volume of a separation channel.
Figure 10:
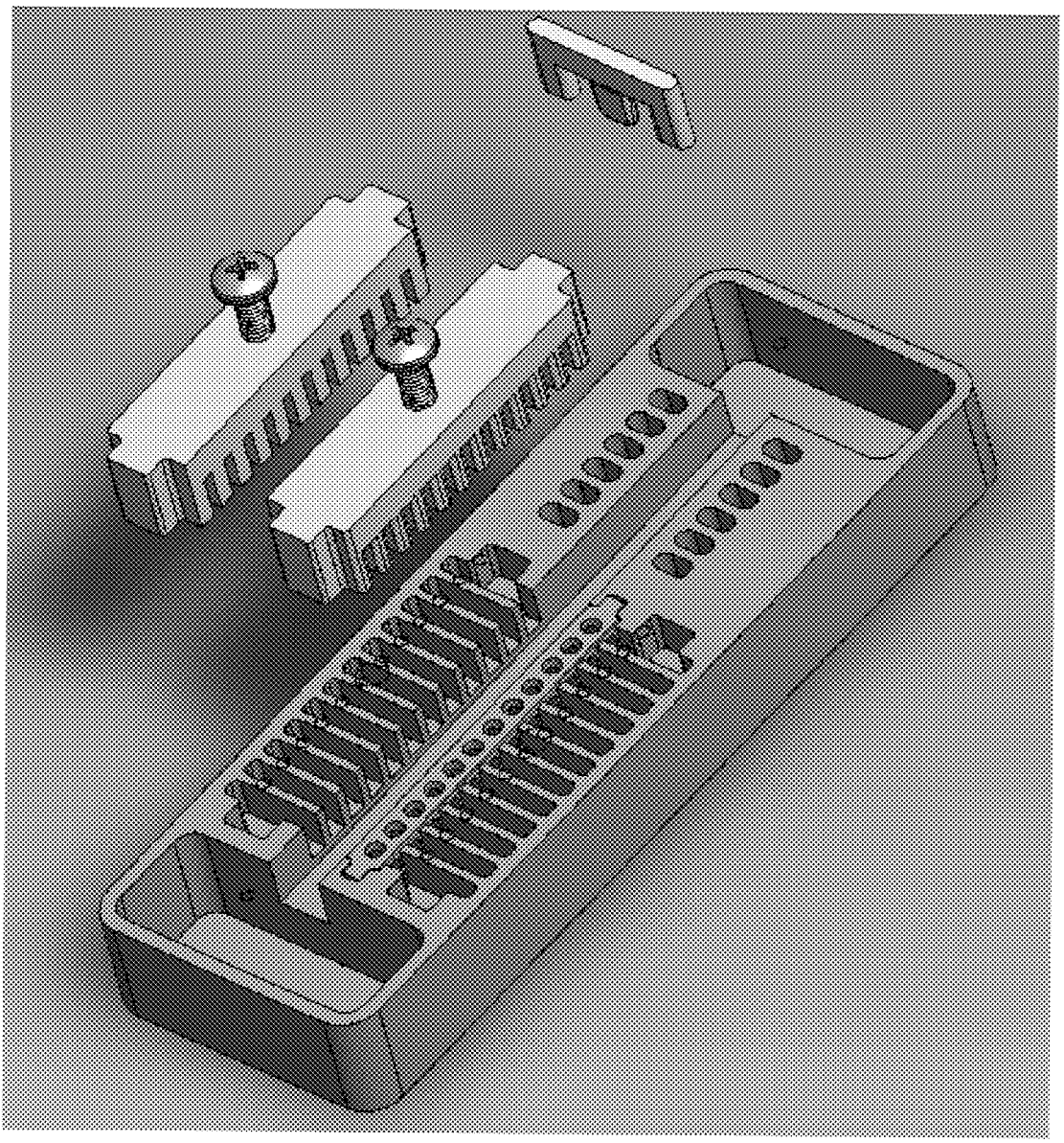
FIG. 10 is a schematic diagram depicting an exploded view the cassette shown in FIG. 9. In this view, only the strip of elution chamber modules remains inserted into the cassette.

A sample well insert was positioned within the separation channel Specifically, the sample well insert was positioned at the third "slot", wherein the first slot is located proximal to the first buffer reservoir and the 6$^{th}$ slot is located distal to the first buffer reservoir (FIG. 9). A slot for holding a sample well insert includes a cavity or recess on either side of the separation channel. When viewing the separation channel oriented such that the first buffer reservoir is "above" the second buffer reservoir (FIGS. 1-3, for example), the left and right cavities or recesses of each slot to hold the sample well insert are horizontally aligned.

An agarose gel matrix composition was poured into the cassette to completely fill a first buffer reservoir, a separation channel, and a second buffer reservoir. After the allowing the liquid mixture to form a gel at room temperature for 35 minutes, the sample well insert, negative elution reservoir insert, and positive elution reservoir insert were removed. The agarose plugs filling a volume of the first and the second buffer reservoirs were cut away from the gel filling a volume of the separation channel and removed from the cassette. The first buffer reservoir, negative elution reservoir, positive elution reservoir and second buffer reservoir were filled 0.5×KBB buffer containing 0.1% w/v SDS.

Platinum electrodes were placed within the first and second buffer reservoirs. More specifically, a negative separation electrode was placed within the first buffer reservoir and a positive separation electrode was placed within the second buffer reservoir. The cassette was "pre-electrophoresed", by activation of the negative and positive separation electrodes, at 90V DC without sample for 5 minutes to allow the SDS from the first buffer reservoir to traverse the sample well. The voltage was switched off and the sample was loaded into the sample well. A separation electrophoresis was carried out at 90V DC until the bromophenol blue dye reached the junction between the separation channel and the second buffer reservoir. The negative and positive separation electrodes were removed. A 12-pin platinum electrode array was inserted into each of the negative and positive elution reservoirs. Specifically, a 12-pin negative electrode array was inserted into the negative elution reservoir and a 12-pin positive electrode array was inserted into the positive elution reservoir. Using the elution electrode arrays for an elution electrophoresis, the samples were eluted from the separation channel into the elution modules of the elution module strip using an applied voltage of 90V for 12 min. The eluted samples were removed from the elution modules using a standard adjustable pipettor, and analyzed by SDS-PAGE gradient gels (4-12% NuPAGE Bis-Tris gels using MES buffer, Invitrogen/Life Technologies) followed by silver staining (BioRad Silver Stain Plus kit, Catalog # 161-0449).

Figure 11:
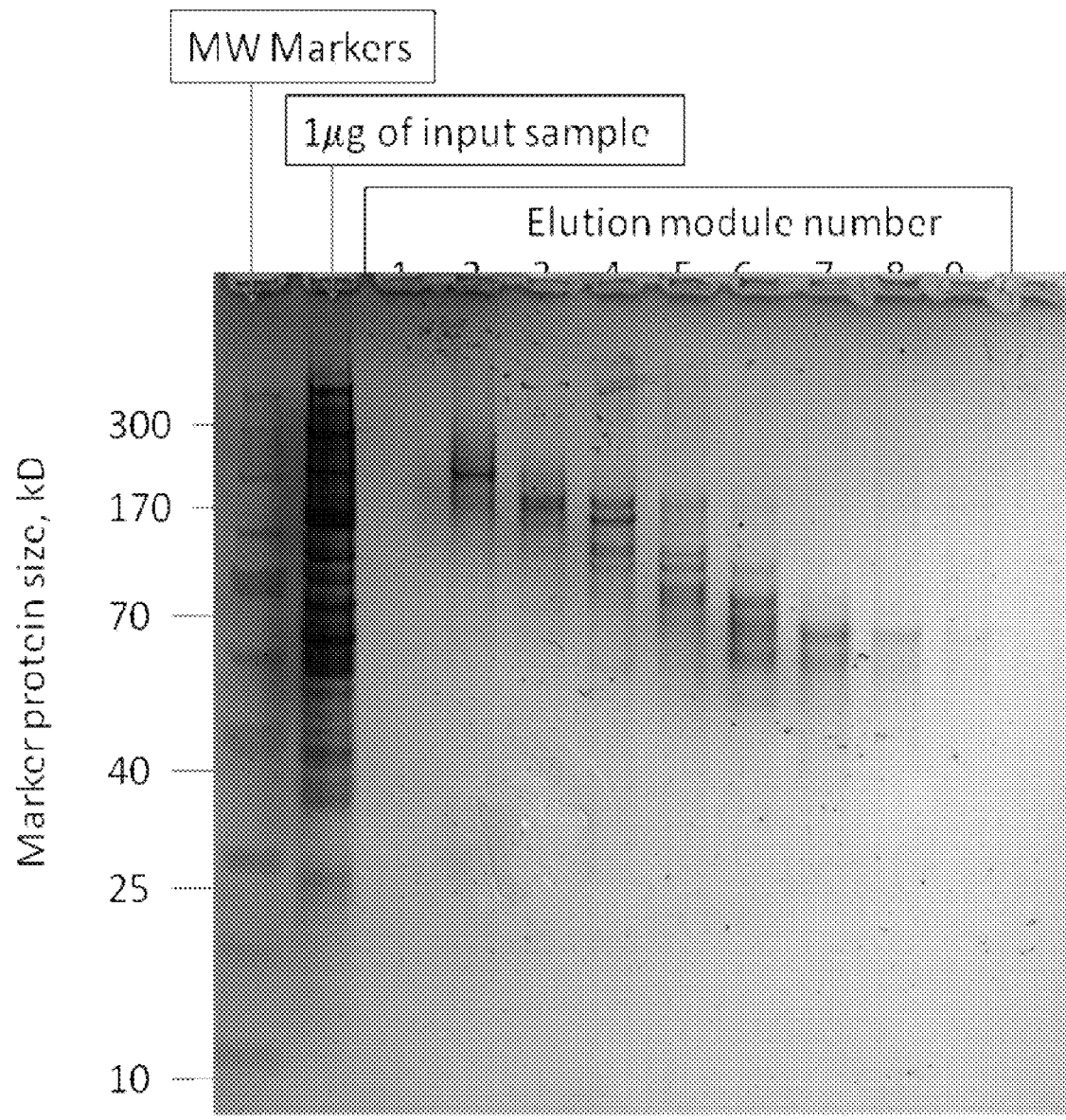
FIG. 11 is a photograph of various fractions of a complex protein sample following simultaneous collection using a cassette of the disclosure. Eluted fractions are numbered according to the elution module in which they were collected. As numbered in this figure, the first elution module is inserted into a position proximal to the sample well whereas the last elution module (9) is inserted into a position distal to the sample well.

As seen in FIG. 11, samples from elution wells 2 through 9 showed different and partially overlapping subsets of the protein analytes in the input lysate sample (lane 2). For each successive elution module position, the eluted fractions decreased in average size. This result was expected because smaller SDS-proteins have higher electrophoretic mobilities, and, therefore, the smaller SDS-proteins will migrate further away from the sample well than a larger SDS-protein during the electrophoresis, thereby reaching an elution module at a position more distal from the sample well than a larger SDS-protein would reach.

Example 2

Size Fractionation of a Complex DNA Sample

Figure 12:
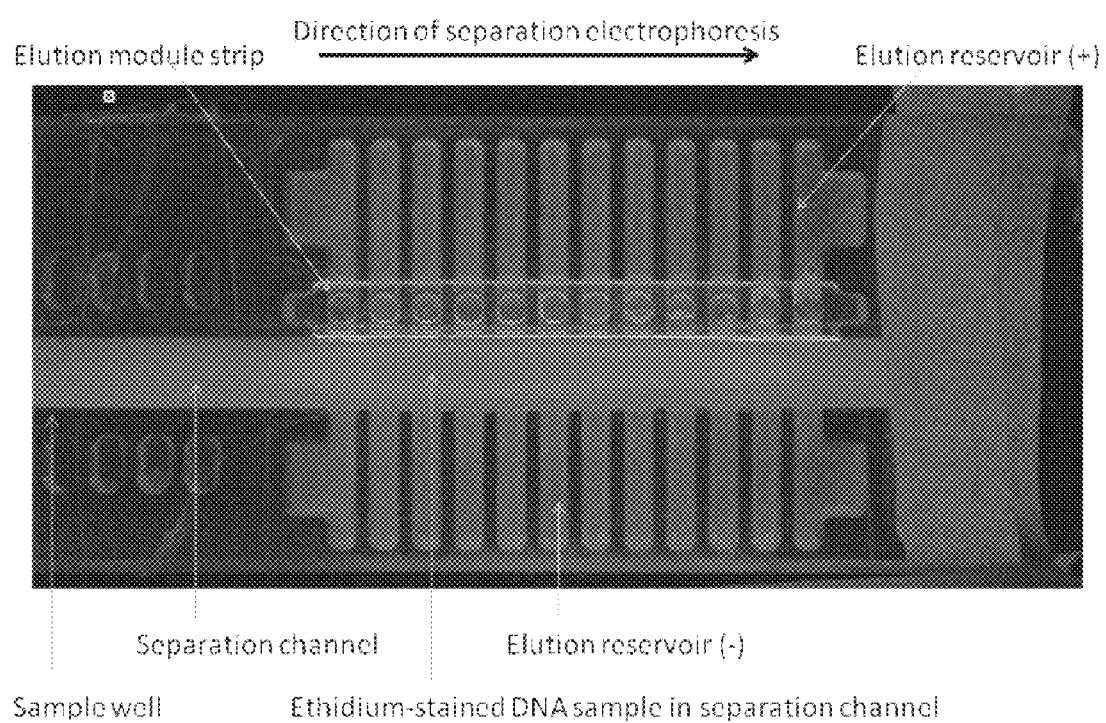
FIG. 12 is a photograph of an exemplary cassette of the disclosure in which an ethidium bromide-stained DNA sample resides in a portion of the separation channel that lies between at least one negative elution reservoir and at least one positive elution reservoir.
Figure 13:
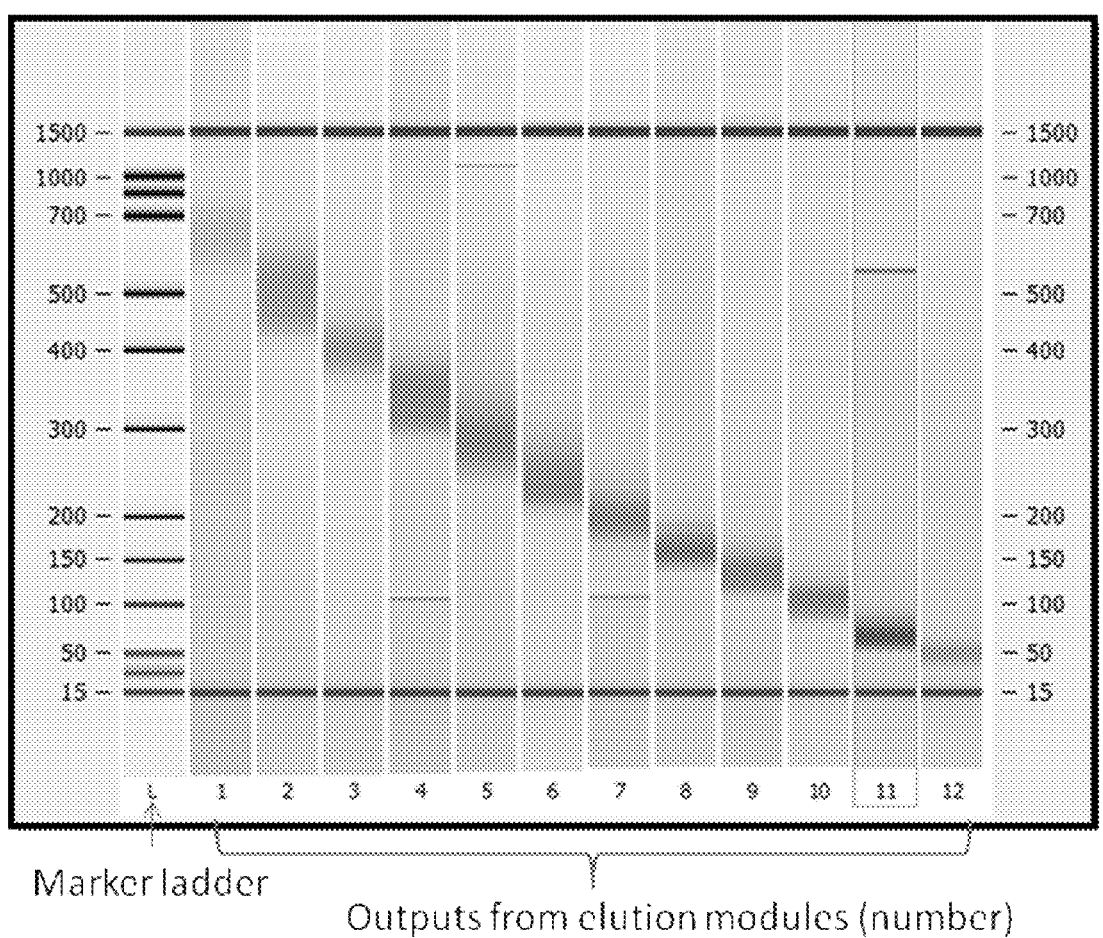
FIG. 13 is a photograph of the results of a capillary electrophoresis procedure performed using the Agilent Bioanalyzer 2100 on DNA fractions collected using a cassette of the disclosure. Collected DNA fractions range in size from 50 base pairs (bp) to approximately 600 bp.
Figure 14:
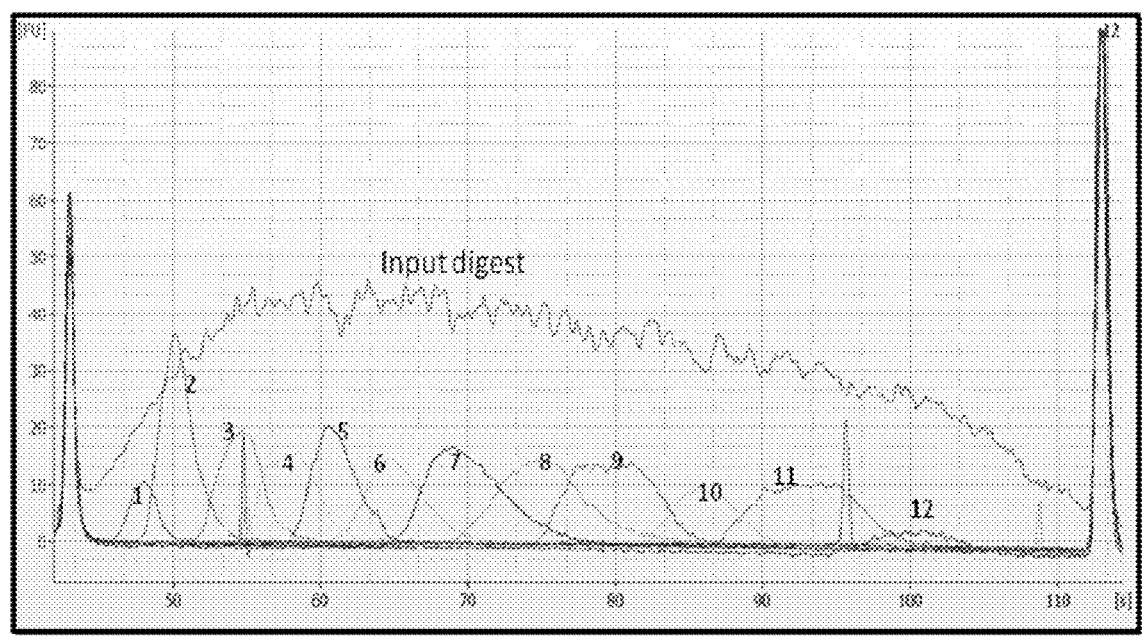
FIG. 14 is electropherogram data from the Agilent Bioanalyzer output samples from FIG. 13 and Example 2. Briefly, DNA from each elution module is labeled, along with input digest DNA. Equal portions of input and output samples were analyzed to allow comparison of output sample yield.
Figure 15:
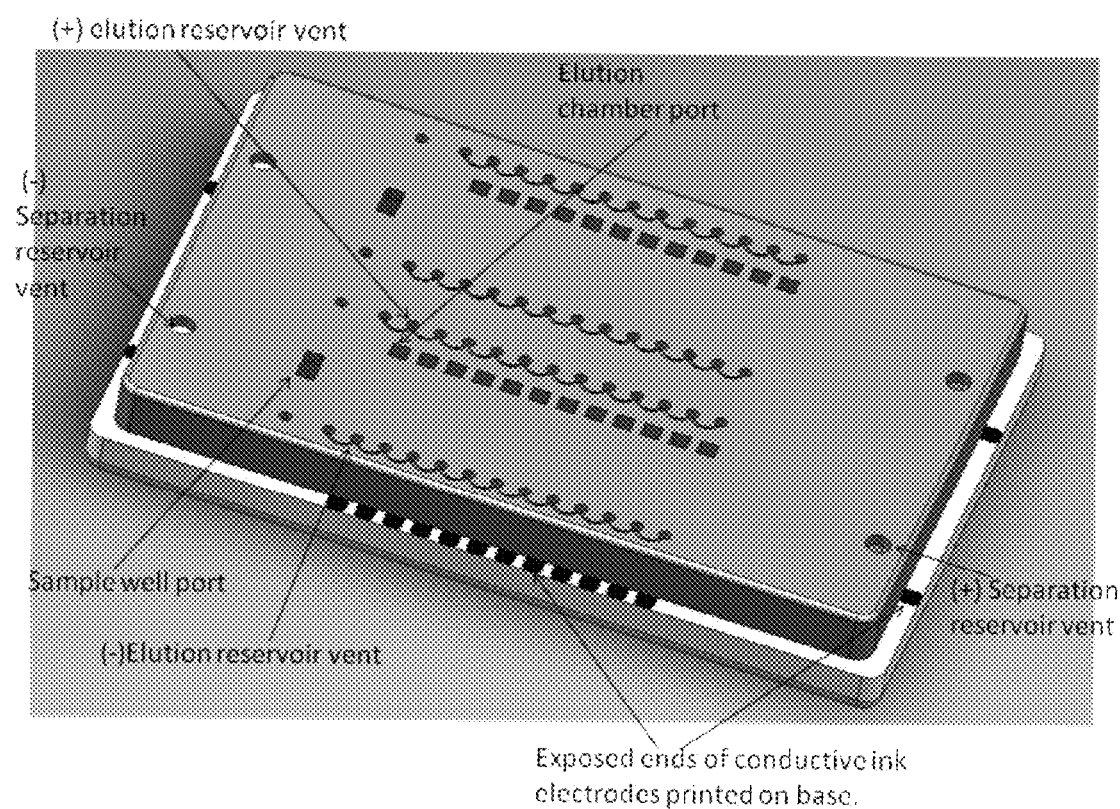
FIG. 15 is a schematic diagram depicting a closed conformation of the cassette described in FIG. 16.
Figure 16:
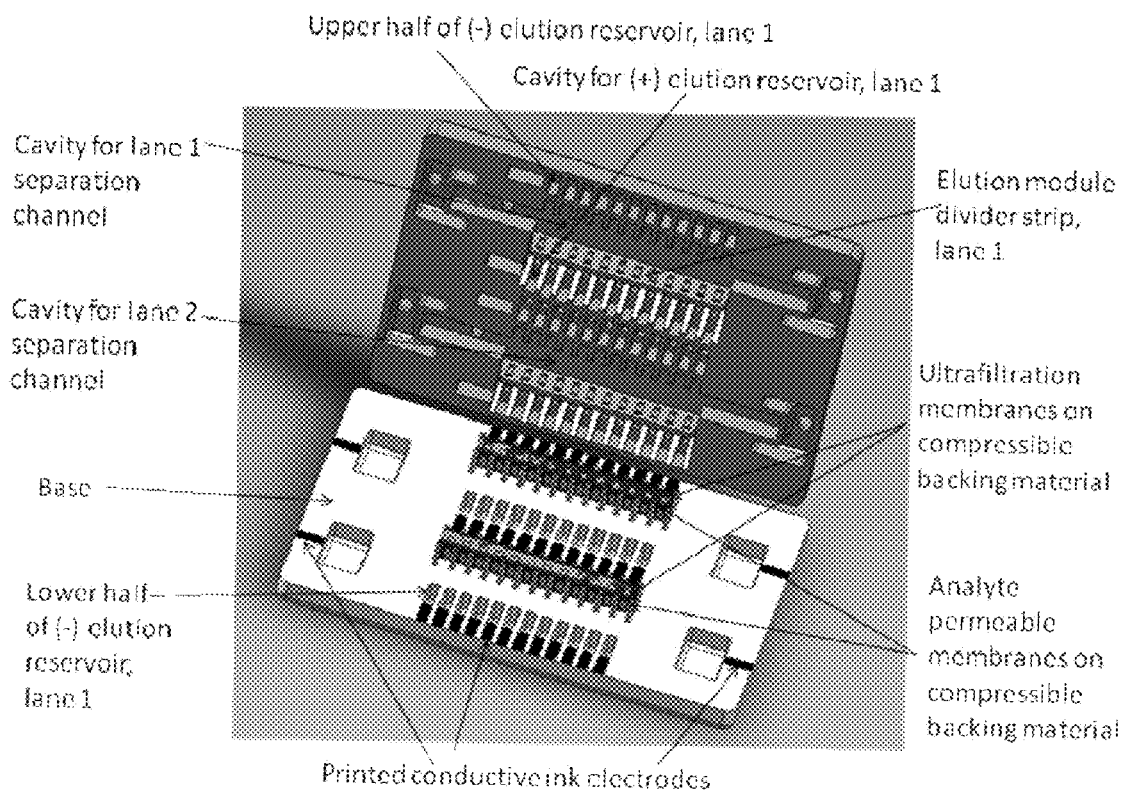
FIG. 16 is a schematic diagram depicting an exemplary two-lane cassette utilizing conductive ink electrodes (presented in an open-configuration in this figure). In this multiunit plate, the central unit is depicted as the "top" unit and the base unit is depicted as the "bottom" unit. The central unit has a closed-face top surface. The central unit, as depicted in this figure, contains two separation channels to be filled with an appropriate gel-matrix composition for separation electrophoresis. As depicted in this figure, the conductive ink electrodes are printed onto the base unit. Alternatively, the conductive ink electrodes may be printed on a base unit, a central unit, or any surface thereof. The central unit includes at least a volume of the negative elution reservoirs, positive elution reservoirs, first buffer reservoirs (for separation electrophoresis), second buffer reservoirs (for separation electrophoresis). The base unit includes at least a volume of the negative elution reservoirs, positive elution reservoirs, first buffer reservoirs (for separation electrophoresis), second buffer reservoirs (for separation electrophoresis). The channels and reservoirs in the base unit correspond or overlap with the channels and reservoirs in the central unit. As depicted in this figure, the base unit is larger than the central unit; however, the inner unit cover overlaps a portion of the printed electrode area on the base unit, thereby providing a conductive path between the exposed portion of the electrode on the top surface of the base and the buffer reservoirs. This conductive path would also be created if the central unit was larger than the base unit, and the printed electrodes were exposed on the bottom surface of the central unit. As depicted in this figure, the "front" and "back" surfaces of the elution modules are attached to a compressible carrier strip (configured to form a V-shape). The "front" surface of the elution modules shown in this figure include an analyte permeable barrier whereas the "back" surfaces of the elution modules shown in this figure include an analyte impermeable barrier. Individual elution modules are created by insertion of a V-shaped elution module divider into a V-shaped membrane holder. For example, the V-shaped membrane holder may be attached or integral to a base unit (as depicted here) or as part of a central unit. The V-shaped compressible carrier strip for the analyte permeable and impermeable membranes may be attached or integral to the V-shaped membrane holder or the V-shaped elution module divider. The V-shaped elution channel divider may be attached or integral to a central unit or a cover. As depicted in this figure, the elution module membranes are maintained in position or "sealed" from contact with more than one elution module by pressure of the divider strip against the compressible carrier.
Figure 19A:
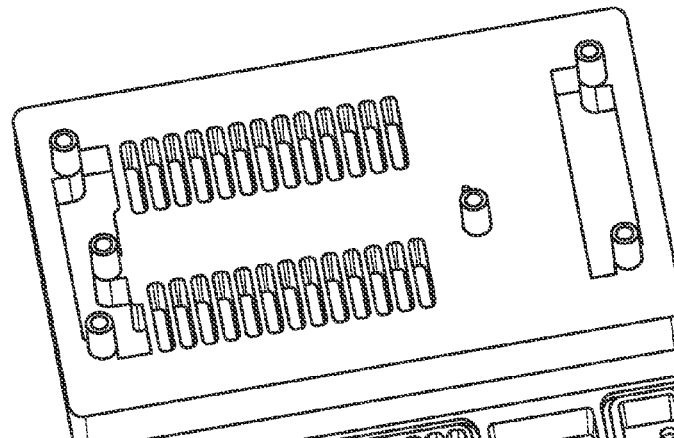
FIGS. 19A-B are a pair of schematic drawings depicting an exemplary injection-molded side-eluting cassette with upside-down filling capabilities.
Figure 19B:
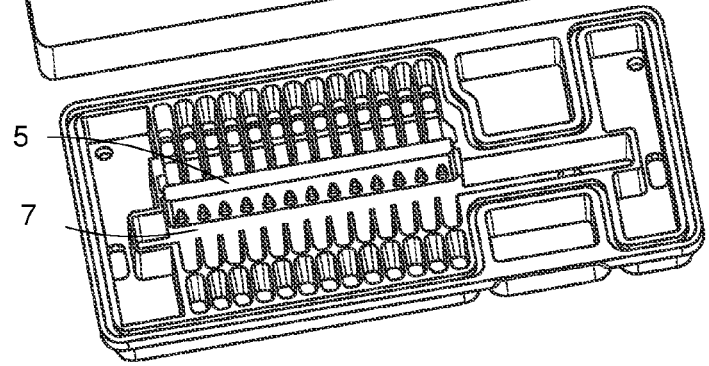
Figure 20:
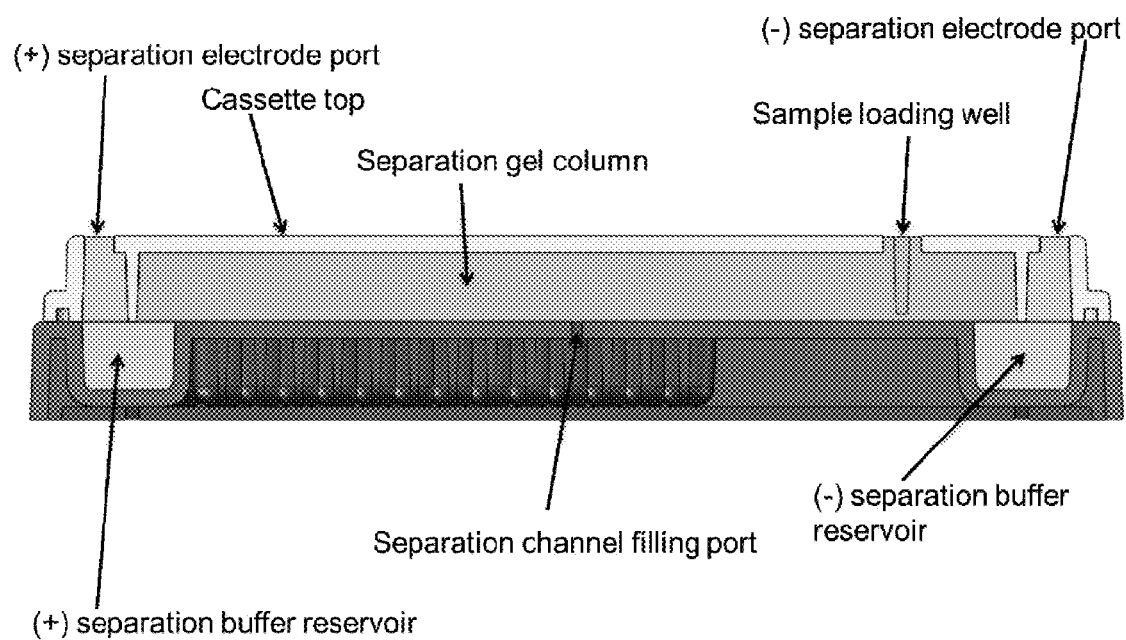
FIG. 20 is a schematic drawing depicting an exemplary injection-molded side-eluting cassette with upside-down filling capabilities. The schematic is presented as a cross-section through a separation channel (in this particular example, the exemplary cassette contains a singular separation channel) This figure depicts (from left to right): at least one positive separation electrode port, at least one positive buffer reservoir (positive separation buffer reservoir) corresponding to at least one separation channel; at least one cassette top (also referred to as a top unit that may comprise a cover unit and a central unit); at least one separation channel filled with a liquid or solid gel matrix composition (also known as a separation gel column); at least one port for inserting liquid gel matrix composition into at least one separation channel (also known as separation channel filling port) (in this particular example the arrow points to a singular port for inserting liquid gel matrix composition into a singular separation channel); at least one sample loading well generated by the insertion of at least one sample well insert into at least one separation channel prior to injection of a liquid gel matrix composition and subsequent removal of the at least one sample well insert once the liquid gel matrix composition becomes solid; at least one negative buffer reservoir (negative separation buffer reservoir) corresponding to at least one separation channel; and at least one negative separation electrode port.
Figure 21:
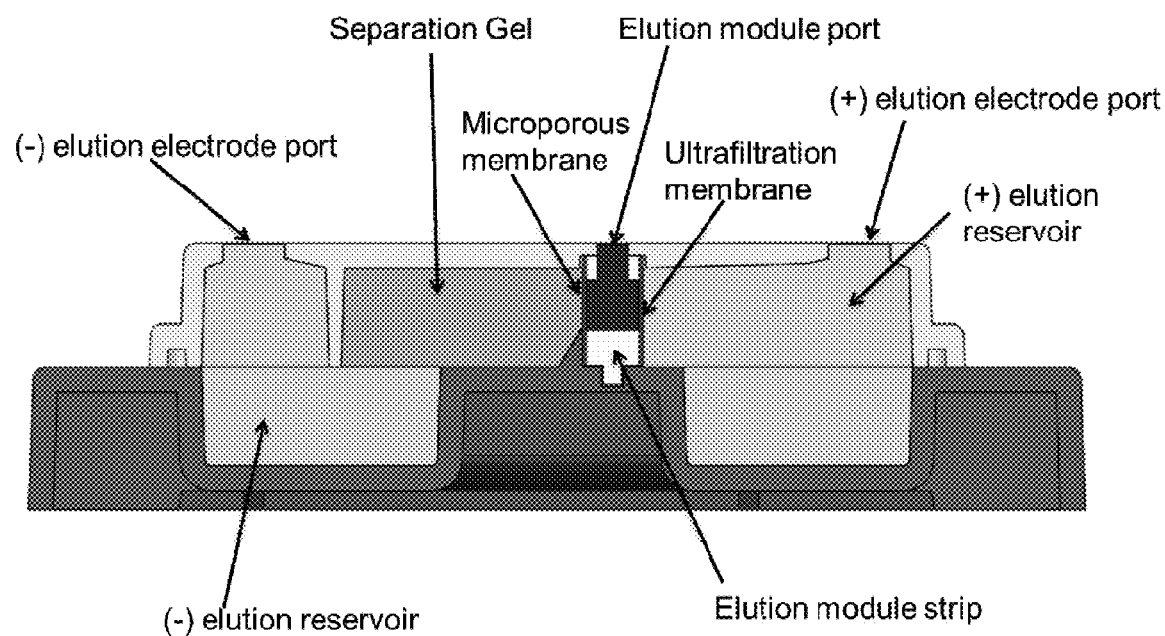
FIG. 21 is a schematic drawing depicting an exemplary injection-molded side-eluting cassette with upside-down filling capabilities. The schematic is presented as a cross-section through a positive elution channel (exemplary cassettes may contain one or more positive elution channels). Preferably, the number of negative elution channels and the number of positive elution channels in any given electrophoresis cassette are equal to one another. This figure depicts (from left to right): at least one negative elution electrode port (corresponding to at least one negative elution channel); at least one negative elution reservoir (corresponding to at least one negative elution channel); at least one separation channel filled with a solid gel matrix composition (also known as a separation gel); at least one elution module (preferably integral to at least one elution module strip), the at least one elution module comprising, consisting essentially of or consisting of at least one analyte-permeable barrier (e.g. a microporous membrane), at least one elution module port (sample collection port), at least one sample collection chamber, and at least one analyte-impermeable barrier (e.g. an ultrafiltration membrane); at least one positive elution electrode port (corresponding to at least one positive elution channel), and at least one positive elution reservoir (corresponding to at least one positive elution channel).
Figure 23A:
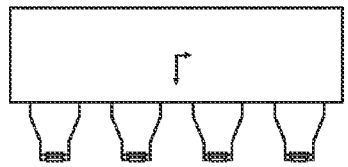
FIG. 23A-E is a series of schematic drawings depicting alternative views of an exemplary instrument electrode contact suitable for use with electrophoresis cassettes having printed electrodes.
Figure 23B:
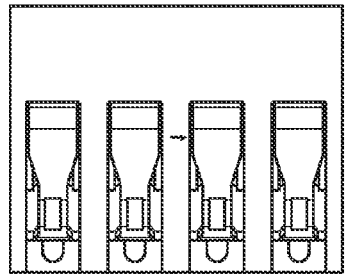
Figure 23C:
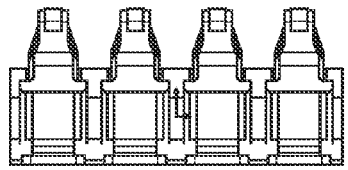
Figure 23D:
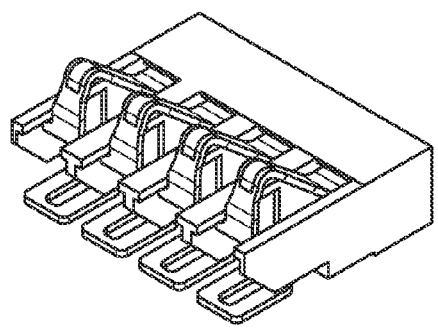
Figure 23E:
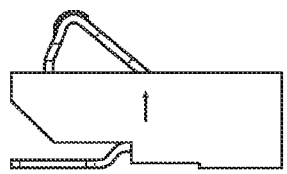
Figure 24:
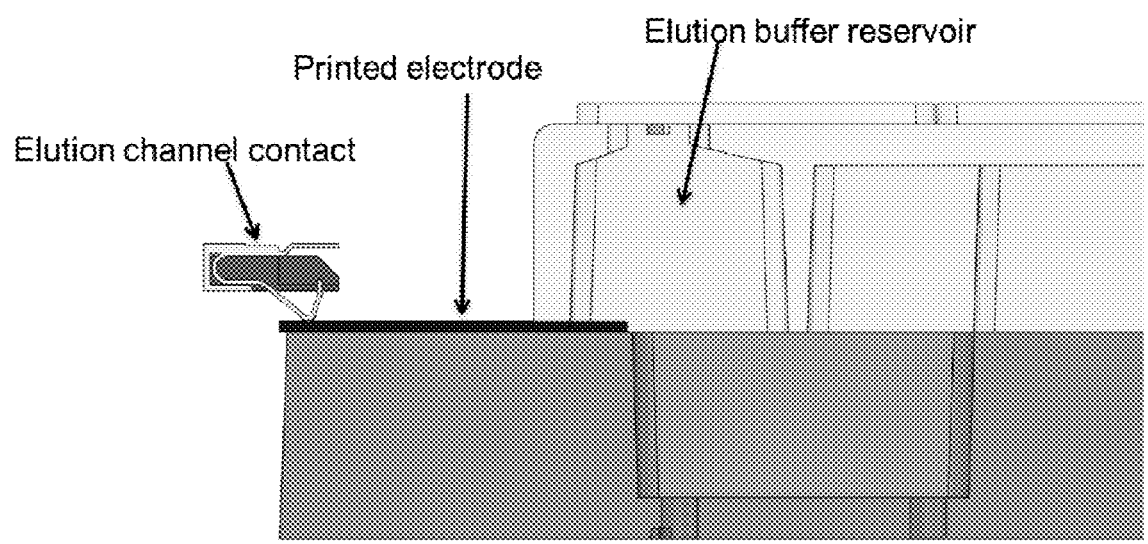
FIG. 24 is a schematic drawing depicting an exemplary side-eluting cassette with printed electrodes. Specifically, this schematic depicts a cross-section through an elution channel to demonstrate the positioning of an instrument contact with a printed elution electrode. The instrument contact interacts with a portion of the printed electrode that lies outside of the elution channel or elution channel buffer reservoir, however, the printed electrode extends from this external area to a position that contacts the elution channel buffer reservoir or the elution buffer contained therein. The relationship of the instrument contact to a printed separation electrode is identical to the relationship of the instrument contact to a printed elution electrode.
Figure 25A:
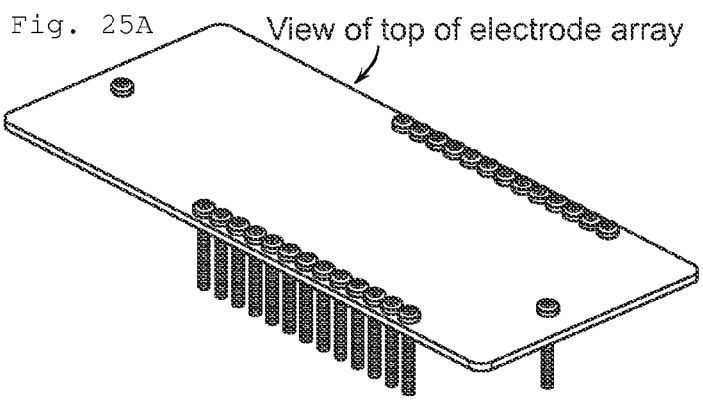
FIG. 25A-B is a pair of schematic drawings depicting an exemplary instrument-based electrode array for an exemplary side-eluting cassette. Each electrode is formed by winding or wrapping conductive wire around a central post or screw. In certain embodiments, the conductive wire may be platinum wire. Alternatively, or in addition, in certain embodiments, the central post or screw is comprised of a plastic material. The electrode may be inserted into one or more separation or elution electrode ports in exemplary side-eluting cassettes.
Figure 25B:
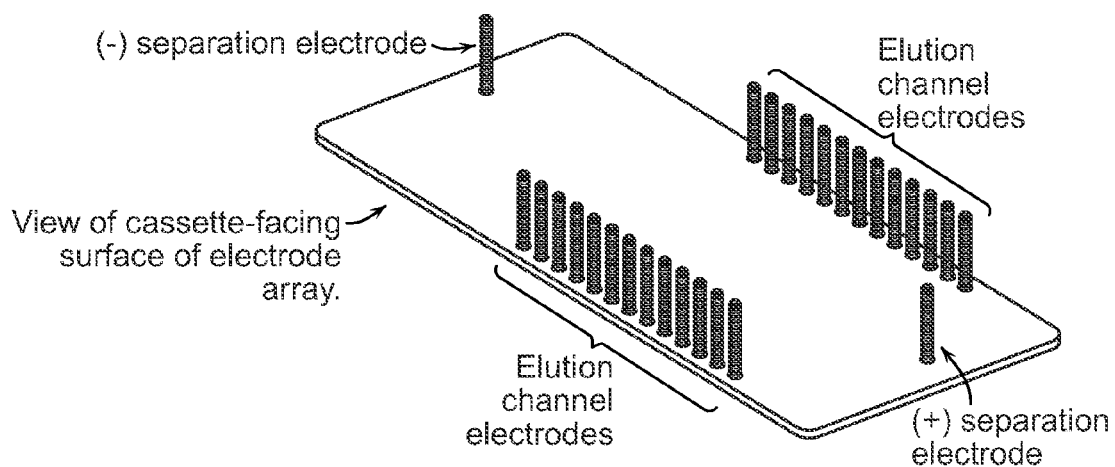
Figures 26A, 26B, 26C:
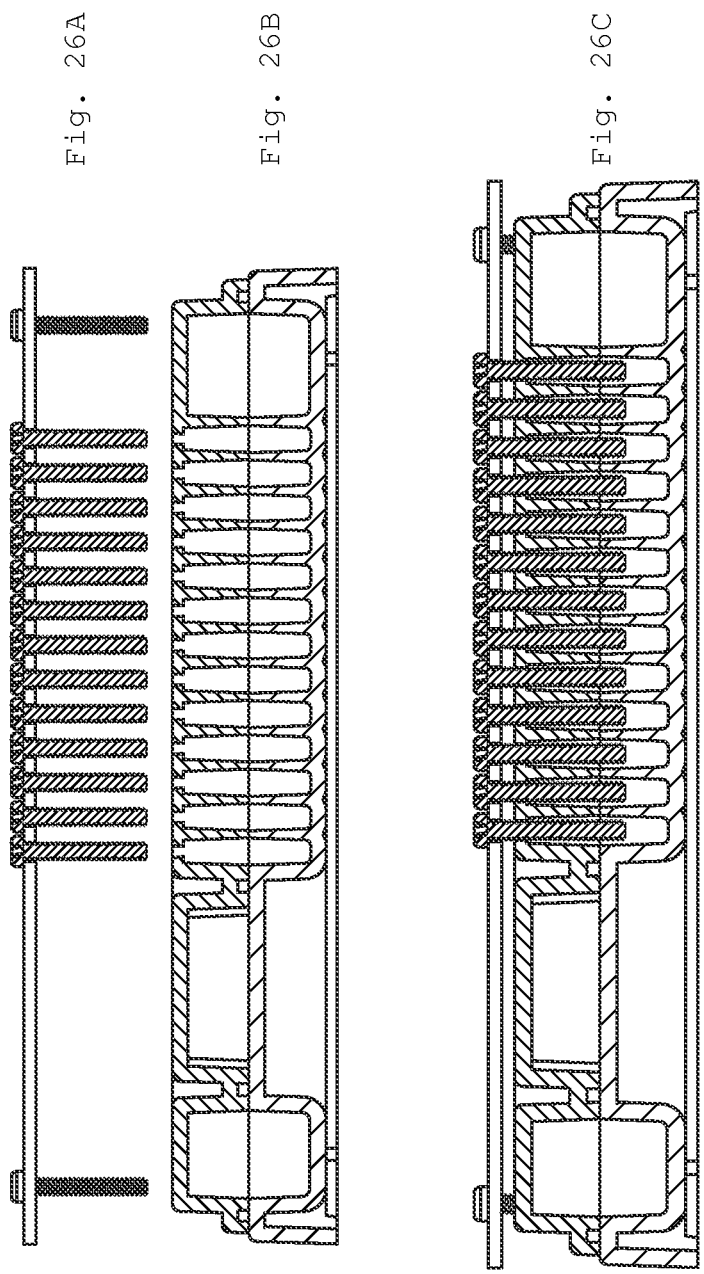
FIGS. 26A-C are schematic drawings illustrating an exemplary fit between the exemplary instrument electrode array of FIG. 25 and an exemplary cassette designed to accept or contact the array (i.e., the configuration of the surface of the cassette or a central or base unit thereof corresponds to the configuration of the electrode array or cover unit of the cassette).
Figure 28:
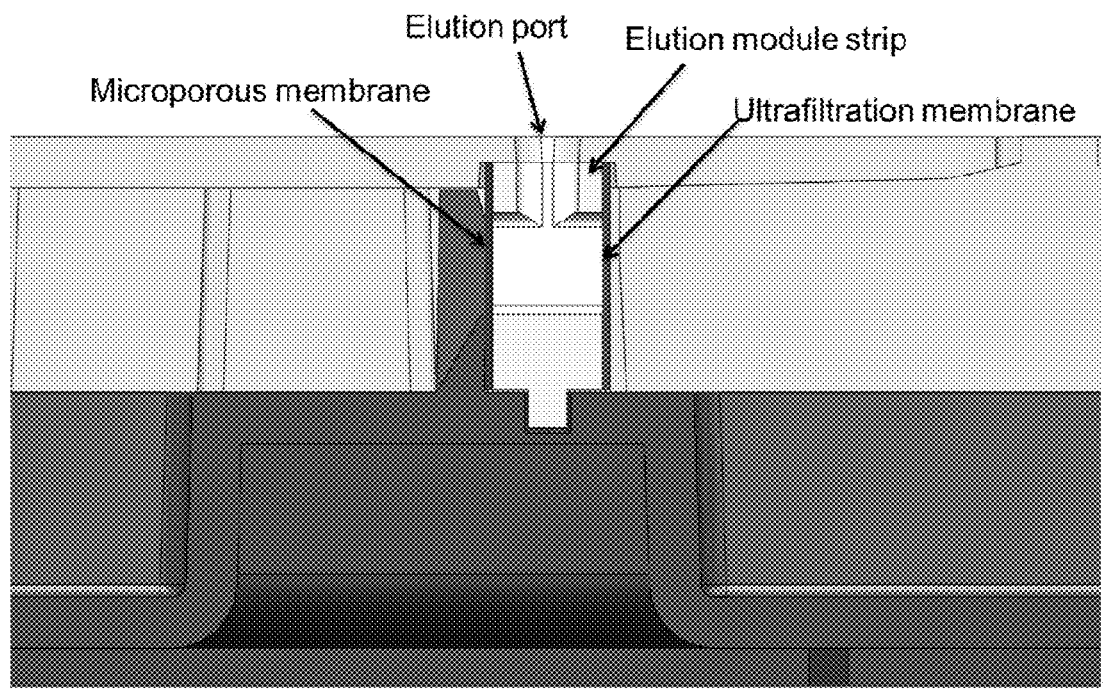
FIG. 28 is a schematic drawing depicting a cross-sectional view though an elution channel of an exemplary cassette containing the elution module strip of FIG. 27.
Figures 29A, 29B:
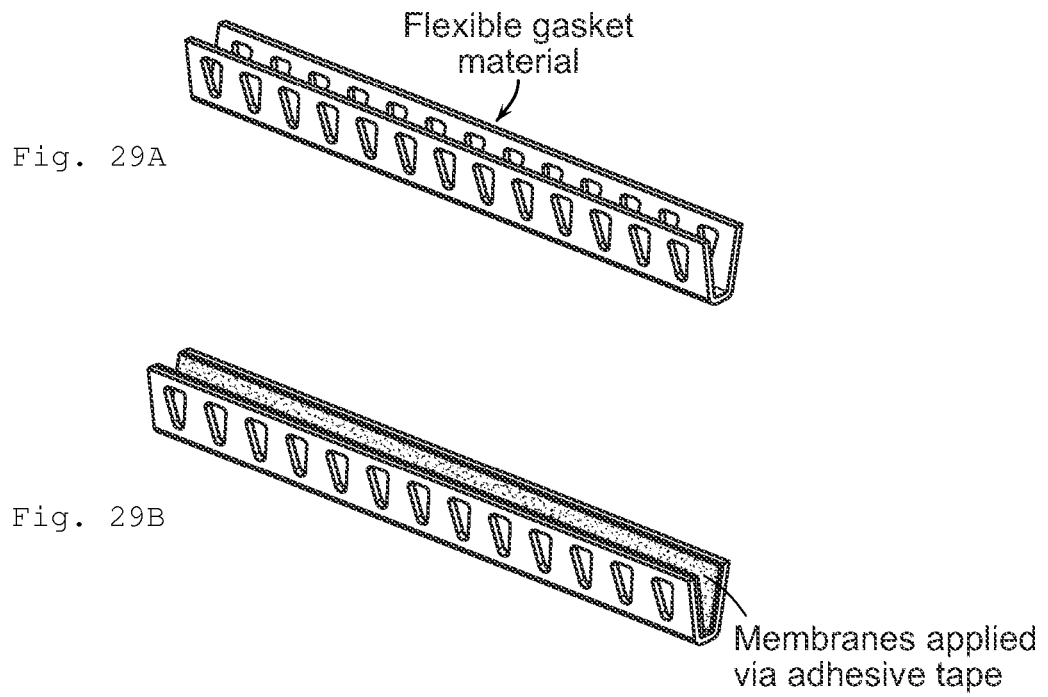
FIGS. 29A-B are schematic drawings depicting an exemplary flexible gasket-style elution module. The top panel.
Figure 30:
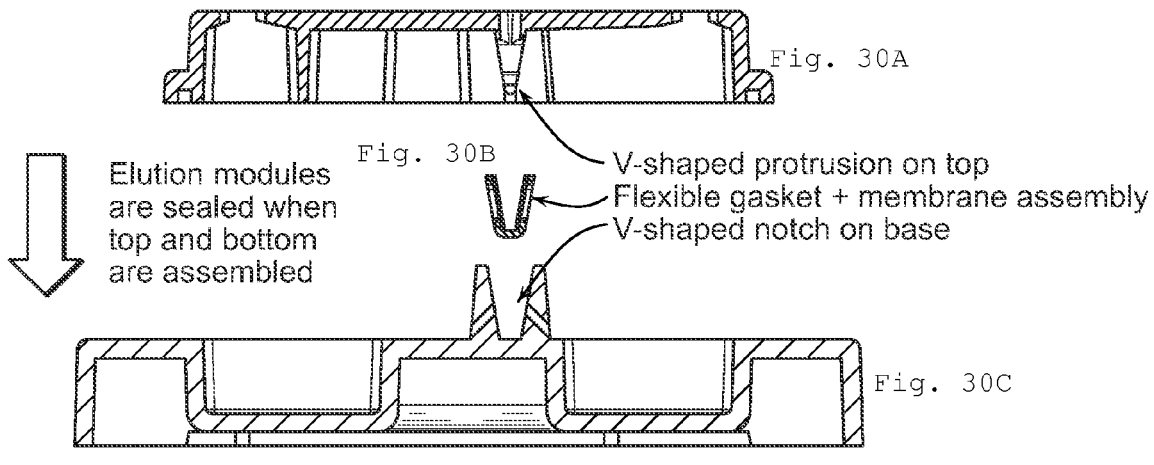
FIGS. 30A-C show schematic drawings depicting the assembly of an exemplary flexible gasket-style elution module strip, FIG. 30B, and insertion of the resultant elution module strip into an exemplary cassette having a base unit, FIG. 30C, and a top unit, FIG. 30A. As an initial step, one or more barriers or membranes are contacted to the interior front and rear faces of a flexible gasket-style elution module. For example, the flexible gasket-style elution module is positioned inside of a V-shaped notch in the base unit, and, subsequently a V-shaped protrusion of the top unit contacts the gasket-style elution module within the base. As a result, the elution module is sealed as a sandwich between the V-shaped protrusion of the cassette top unit and the V-shaped notch of the cassette bottom unit.
Figure 31:
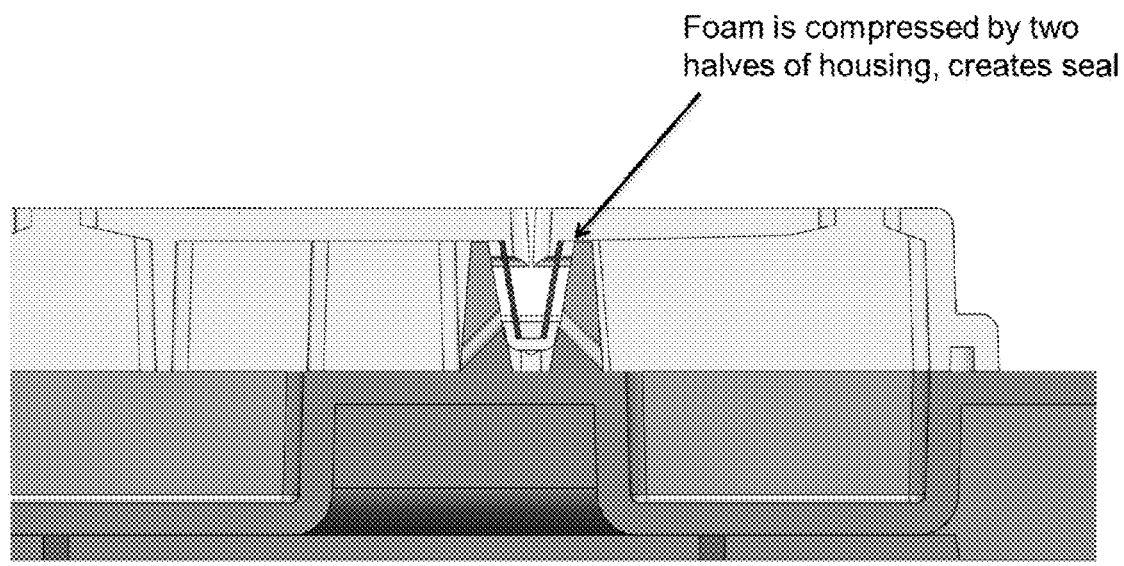
FIG. 31 is a schematic drawing depicting a cross-section through an elution channel of an exemplary assembled flexible gasket-style elution module strip. As described in FIG. 30, the union of a top and base unit of the cassette compresses at least one membrane or foam within the elution module, thereby generating a seal between the at least one membrane and the flexible gasket-style elution module.
Figure 32:
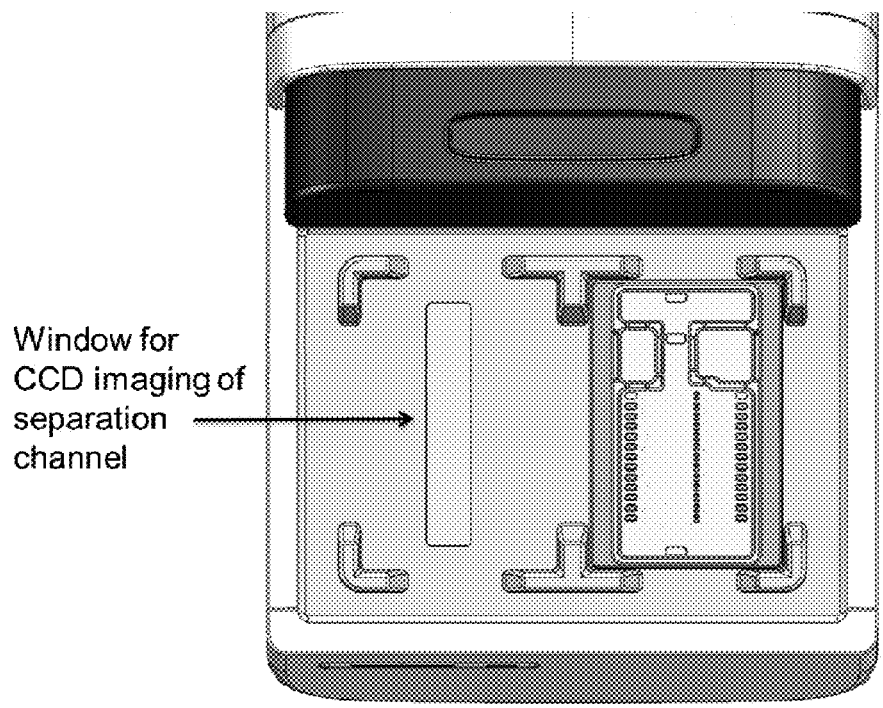
FIG. 32 is a schematic drawing depicting an exemplary instrument for performing electrophoresis. This instrument has the capacity to contain or hold two side-eluting cassettes. For illustration, this figure illustrates the insertion of one of the two cassettes. The empty nest or holder illustrates a window for charge-coupled device (CCD) imaging of at least one separation channel within each cassette.
Figure 33:
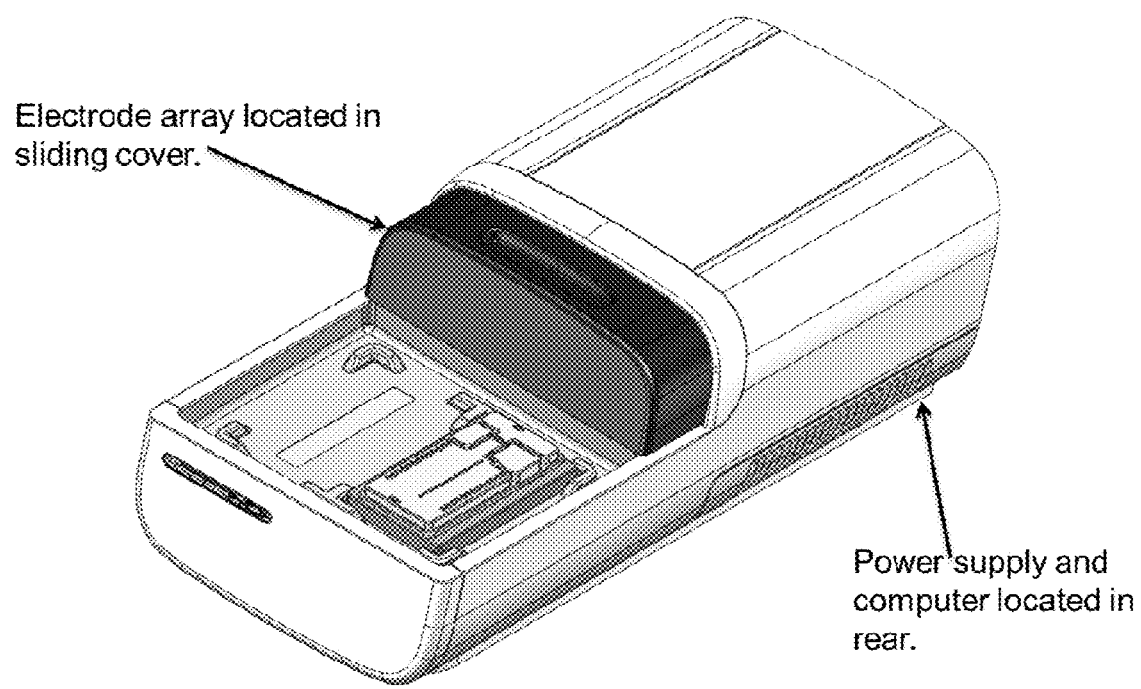
FIG. 33 is a schematic drawing depicting an exemplary instrument for performing electrophoresis. In this exemplary instrument, an electrode array is positioned within a sliding cover. Alternatively, or in addition, a power supply is located in the rear of the instrument. In another embodiment, a power supply and a processor are located in the rear of the instrument. The processor may be integral to the instrument and/or contained within a computer. A computer may be integral or separate from the electrophoresis instrument.

A gel cassette of the design shown in FIG. 9 was prepared as described in Example 1, with the following exceptions: the gel matrix composition included 2% low melting agarose (SeaPlaque agarose, Lonza), the gel matrix composition, the first and second buffer reservoirs and the negative and positive elution reservoirs, included a buffer composition containing 0.5×KBB with 2 μg/ml ethidium bromide. SDS was not used in either the gel matrix composition or the buffer composition. The input DNA sample included restriction enzyme digested E. coli genomic DNA (5 μg of DNA completely digested with HinfI and MspI, New England Biolabs). The separation electrophoresis was carried out for 90 minutes at 87V DC. Following the separation electrophoresis, the cassette was photographed under UV light as shown in FIG. 12. FIG. 12 shows that the genomic DNA sample remains centered in the separation channel during the separation phase electrophoresis. After photography, the separation electrodes were removed from the cassette and two 12-pin platinum elution electrode arrays were positioned within the negative and positive elution reservoirs. Specifically, a 12-pin negative electrode array was inserted into the negative elution reservoir and a 12-pin positive electrode array was inserted into the positive elution reservoir. An elution electrophoresis was carried out at 87V DV for 7 minutes. The eluted DNA was removed from each elution module of the elution module strip using a standard manual pipettor. Aliquots of the input restriction digest and the eluted fractions were analyzed by capillary electrophoresis (Agilent Bioanalyzer 2100). The results of the capillary electrophoresis are shown in FIGS. 13 and 14. Outputs ranged in size from 50 base pairs (bp) (elution module number 12) to approximately 600 bp (elution module number 1) (FIG. 13). Yields were estimated from the electropherogram in FIG. 14 to be in the range of 25-40% for most fractions.

Other Embodiments

While the invention has been described in conjunction with the detailed description thereof, the foregoing description is intended to illustrate and not limit the scope of the disclosure. Other aspects, advantages, and modifications are within the scope of the disclosure.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this disclosure has been particularly shown and described with references to preferred embodiments thereof, it will be understood by those skilled in the art that various changes in form and details may be made therein without departing from the scope of the disclosure.

What is claimed is:

1. An electrophoresis cassette comprising:
a top plate comprising at least one macrofluidic separation channel, at least one of an opening, a cavity, or a recess corresponding to a portion of a positive elution channel, at least one of an opening, a cavity, or a recess corresponding to a portion of a negative elution channel, and at least one elution module, and
a bottom plate,
wherein the top plate and bottom plate are contacted or adhered to one another, and wherein said at least one elution module is arranged between said separation channel and said portion of the positive elution channel.

2. The cassette of claim 1, wherein the bottom plate comprises at least one of an opening, a cavity, or a recess corresponding to a portion of a positive elution channel, at least one of an opening, cavity, or a recess corresponding to a portion of a negative elution channel, and at least one of an opening, cavity, or a recess corresponding to said at least one elution module.

3. The cassette of claim 2, wherein the contacting or adhesion of the top plate and the bottom plate forms at least one positive elution channel and at least one negative elution channel.

4. The cassette of claim 1, wherein the elution module comprises
a four-sided structure having a solid bottom surface, a top surface comprising an elution port, and two side surfaces each having at least one of an opening, cavity, or a recess corresponding to a positive elution channel or a negative elution channel, and
an analyte-impermeable membrane in contact with at least one side of the structure.

5. The cassette of claim 4, wherein the two side surfaces taper from a wider configuration near the top surface to a narrower configuration near the bottom surface.

6. The cassette of claim 4, wherein analyte-impermeable membrane contacts or adheres to the side of the structure adjacent to at least one positive elution channel.

7. The cassette of claim 4, wherein the elution module further comprises an analyte-permeable membrane.

8. The cassette of claim 7, wherein the analyte-permeable membrane contacts or adheres to the side of the structure adjacent to at least one negative elution channel.

9. The cassette of claim 1, wherein the elution module contacts or adheres to the top plate in a reversible manner.

10. The cassette of claim 1, wherein the bottom plate further comprises at least one notch corresponding to the at least one elution module.

11. The cassette of claim 10, wherein the notch comprises a three-sided structure having one bottom surface and two side surfaces.

12. The cassette of claim 11, wherein two side surfaces do not cover any opening, cavity, or recess of the elution module channel.

13. The cassette of claim 10, wherein the contacting or adhesion of the top plate and the bottom plate inserts at least one elution module of the top plate into at least one corresponding notch of the bottom plate.

14. The cassette of claim 1, wherein the bottom plate further comprises at least one divider comprising a series of windows corresponding to at least one of an opening, cavity, or recess of the elution module channel, wherein each window aligns with at least one positive elution channel and at least one of a negative elution channel.

15. The cassette of claim 1, wherein the elution module comprises at least one elution chamber and at least one elution port.

16. The cassette of claim 1, wherein the top plate further comprises at least one positive elution electrode channel and at least one negative elution electrode channel.

17. The cassette of claim 16, wherein the at least one positive elution electrode channel occupies a volume of at least one position elution channel and the at least one negative elution electrode channel occupies a volume of at least one negative elution channel.

18. An electrophoresis system comprising:
an electrophoresis cassette, said electrophoresis cassette comprising
a top plate comprising at least one macrofluidic separation channel, at least one of an opening, a cavity, or a recess corresponding to a portion of a positive elution channel, at least one of an opening, a cavity, or a recess corresponding to a portion of a negative elution channel, and at least one elution module, and
a bottom plate,
wherein the top plate and bottom plate are contacted or adhered to one another, and wherein said at least one elution module is arranged between said separation channel and said portion of the positive elution channel;
an electrode array comprising
at least one of a negative separation electrode and a positive separation electrode, wherein the negative separation electrode aligns with a port in the outer surface of the top plate corresponding to a first buffer reservoir at a first end of the separation channel, wherein the positive separation electrode aligns with a port in the outer surface of the top plate corresponding to a second buffer reservoir at a second end of the separation channel, and wherein the first end of the separation channel is proximal to at least one sample well; and
at least one of a negative elution electrode and a positive elution electrode, wherein the negative elution electrode aligns with an elution electrode channel in the outer surface of the top plate occupying a volume of at least one negative elution channel, wherein the positive elution electrode aligns with an elution electrode channel in the outer surface of the top plate occupying a volume of at least one positive elution channel; and
a processor configured to
activate power to at least one pair of positive and negative separation electrodes during a separation electrophoresis,
deactivate power to the at least one pair of positive and negative separation electrodes and activate power to at least one pair of positive and negative elution electrodes during an elution electrophoresis; and a power module comprising at least one of a power supply and a relay to provide power to at least one of the processor and at least one pair of positive and negative separation electrodes or at least one pair of positive and negative elution electrodes.

19. A method of fractionating analytes within a sample, comprising:

providing the system of claim 18, wherein the cassette further comprises at least one of:
- a buffer reservoir insert that occupies a volume of at least one buffer reservoir,
- a sample well insert that occupies a volume of the separation channel aligned with at least one of a sample port, and
- an injection port, wherein the injection port comprises an opening in an outer surface of the bottom plate, and wherein the system further comprises an instrument for receiving the cassette;

inserting a gel matrix composition through the injection port;

solidifying the gel matrix composition, wherein the gel matrix composition transforms from a liquid to a solid;

removing the buffer reservoir insert and sample well insert, wherein a sample well is generated;

filling at least one buffer reservoir and at least one pair of positive and negative elution channels with a buffer composition; and inserting the electrophoresis cassette into the instrument;

programming the processor of the system to selectively activate the at least one pair of positive and negative separation electrodes during a separation electrophoresis;

programming the processor of the system to selectively deactivate the at least one pair of positive and negative separation electrodes and to selectively activate the at least one pair of positive and negative elution electrodes during an elution electrophoresis;

applying the sample to the sample well;

applying a voltage across the electrophoresis cassette during a separation electrophoresis;

applying a voltage across the electrophoresis cassette during an elution electrophoresis; and collecting analytes of the sample having a desired electrophoretic mobility in the at least one elution module, thereby fractionating analytes within a sample.

* * * * *